US012708783B2

(12) United States Patent
Mishra et al.

(10) Patent No.: US 12,708,783 B2
(45) Date of Patent: Aug. 18, 2026

(54) APPARATUS FOR DELIVERING ENHANCED STIMULATION WAVEFORMS

(71) Applicant: Nalu Medical, Inc., Carlsbad, CA (US)

(72) Inventors: Lakshmi Narayan Mishra, Carlsbad, CA (US); Gaurav Kulkarni, Pune (IN); Mandar Hemant Gadgil, Pune (IN); Casey James O'Connell, San Marcos, CA (US); Cyanna Moody, Carlsbad, CA (US)

(73) Assignee: Nalu Medical, Inc., Carlsbad, CA (US)

(*) Notice: Subject to any disclaimer, the term of this patent is extended or adjusted under 35 U.S.C. 154(b) by 194 days.

(21) Appl. No.: 18/463,225

(22) Filed: Sep. 7, 2023

(65) Prior Publication Data

US 2024/0278022 A1 Aug. 22, 2024

Related U.S. Application Data

(63) Continuation of application No. PCT/US2022/020452, filed on Mar. 15, 2022.

(60) Provisional application No. 63/273,068, filed on Oct. 28, 2021, provisional application No. 63/161,757, filed on Mar. 16, 2021.

(51) Int. Cl.
*A61N 1/372* (2006.01)
*A61N 1/36* (2006.01)

(52) U.S. Cl.
CPC ..... *A61N 1/37264* (2013.01); *A61N 1/36071* (2013.01); *A61N 1/36157* (2013.01); *A61N 1/37247* (2013.01)

(58) Field of Classification Search
CPC ........................ A61N 1/37264; A61N 1/36071
USPC ............................................................ 607/46
See application file for complete search history.

(56) References Cited

U.S. PATENT DOCUMENTS 3,835,833 A 9/1974 Limoge
3,902,501 A 9/1975 Citron et al.
3,939,843 A 2/1976 Smyth et al.
(Continued)

FOREIGN PATENT DOCUMENTS

AU 2014233252 A1 11/2015
EP 1342454 A1 9/2003
(Continued)

OTHER PUBLICATIONS

Buhlmann, J. et al., "Modeling of a segmented electrode for desynchronizing deep brain stimulation" Frontiers in Neuroengineering (2011) vol. 4, Article 15, pp. 1-8.
(Continued)

*Primary Examiner* — Nadia A Mahmood
(74) *Attorney, Agent, or Firm* — Nelson Mullins Riley & Scarborough LLP

(57) ABSTRACT

An apparatus for delivering stimulation to a patient is provided. The apparatus includes an external system for transmitting one or more transmission signals and having at least one antenna, a transmitter, a power supply, and a controller. The apparatus further includes an implantable system for receiving the one or more transmission signals and having at least one antenna, a receiver, at least one stimulation element, a controller, and an energy storage assembly. The at least one stimulation element delivers stimulation energy to tissue of the patient. Methods of delivering stimulation energy are also provided.

16 Claims, 30 Drawing Sheets

(56) References Cited

U.S. PATENT DOCUMENTS 4,033,357 A 7/1977 Helland et al.
4,071,033 A 1/1978 Nawracaj et al.
4,140,133 A 2/1979 Kastrubin et al.
4,236,529 A 12/1980 Little
4,262,678 A 4/1981 Stokes
4,269,198 A 5/1981 Stokes
4,301,815 A 11/1981 Doring
4,324,251 A 4/1982 Mann
4,407,303 A 10/1983 Akerstroem
4,409,994 A 10/1983 Doring
4,469,104 A 9/1984 Peers-Trevarton
4,506,679 A 3/1985 Mann
4,578,598 A 3/1986 Faulhaber
4,582,069 A 4/1986 McArthur
4,592,356 A 6/1986 Gutierrez
4,627,438 A 12/1986 Liss et al.
4,658,835 A 4/1987 Pohndorf
4,716,888 A 1/1988 Wesner
4,721,118 A 1/1988 Harris
4,735,204 A 4/1988 Sussman et al.
4,796,643 A 1/1989 Nakazawa et al.
4,841,971 A 6/1989 Hess
4,883,070 A 11/1989 Hanson
4,898,173 A 2/1990 Daglow et al.
4,922,908 A 5/1990 Morawetz et al.
4,945,922 A 8/1990 Van
4,957,118 A 9/1990 Erlebacher
5,031,618 A 7/1991 Mullett
5,107,856 A 4/1992 Kristiansen et al.
5,131,389 A 7/1992 Giordani
5,143,067 A 9/1992 Rise et al.
5,193,539 A 3/1993 Schulman et al.
5,201,312 A 4/1993 Schenck et al.
5,257,634 A 11/1993 Kroll
5,273,053 A 12/1993 Pohndorf
5,282,845 A 2/1994 Bush et al.
5,300,107 A 4/1994 Stokes et al.
5,395,328 A 3/1995 Ockuly et al.
5,540,736 A 7/1996 Haimovich et al.
5,545,206 A 8/1996 Carson
5,662,697 A 9/1997 Li et al.
5,735,887 A 4/1998 Barreras, Sr. et al.
5,814,089 A 9/1998 Stokes et al.
5,827,311 A 10/1998 Berelsman et al.
5,833,603 A 11/1998 Kovacs et al.
5,868,741 A 2/1999 Chia et al.
5,908,433 A 6/1999 Eager et al.
5,957,965 A 9/1999 Moumane et al.
6,021,354 A 2/2000 Warman et al.
6,058,331 A 5/2000 King
6,169,925 B1 1/2001 Villaseca et al.
6,181,973 B1 1/2001 Ceron et al.
6,188,932 B1 2/2001 Lindegren
6,240,322 B1 5/2001 Peterfeso et al.
6,275,737 B1 8/2001 Mann
6,304,786 B1 10/2001 Heil, Jr. et al.
6,324,430 B1 11/2001 Zarinetchi et al.
6,324,434 B2 11/2001 Coe et al.
6,405,091 B1 6/2002 Vachon et al.
6,482,152 B2 11/2002 Kim
6,510,347 B2 1/2003 Borkan
6,522,926 B1 2/2003 Kieval et al.
6,561,975 B1 5/2003 Pool et al.
6,850,803 B1 2/2005 Jimenez et al.
6,884,122 B2 4/2005 Robinson et al.
6,895,280 B2 5/2005 Meadows et al.
6,904,322 B2 6/2005 Katsnelson
6,909,917 B2 6/2005 Woods et al.
6,950,706 B2 9/2005 Rodriguez et al.
6,999,819 B2 2/2006 Swoyer et al.
7,092,763 B1 8/2006 Griffith et al.
7,096,070 B1 8/2006 Jenkins et al.
7,239,921 B2 7/2007 Canfield et al.
7,346,391 B1 3/2008 Osorio et al.
7,616,990 B2 11/2009 Chavan et al.
7,711,419 B2 5/2010 Armstrong et al.
7,717,848 B2 5/2010 Heruth et al.
7,734,340 B2 6/2010 De
7,734,354 B1 6/2010 Cox
7,737,905 B1 6/2010 Meloling et al.
7,742,818 B2 6/2010 Dinsmoor et al.
7,801,615 B2 9/2010 Meadows et al.
7,899,550 B1 3/2011 Doan et al.
7,912,555 B2 3/2011 Swoyer et al.
7,925,357 B2 4/2011 Phillips et al.
7,991,479 B2 8/2011 Phillips et al.
8,000,805 B2 8/2011 Swoyer et al.
8,036,756 B2 10/2011 Swoyer et al.
8,086,317 B2 12/2011 Finch et al.
8,224,453 B2 7/2012 De
8,252,011 B1 8/2012 Forrester et al.
8,280,517 B2 10/2012 Skelton et al.
8,301,268 B1 10/2012 Jones et al.
8,314,594 B2 11/2012 Scott et al.
8,334,677 B2 12/2012 Single
8,364,273 B2 1/2013 De
8,388,555 B2 3/2013 Panken et al.
8,401,655 B2 3/2013 De
8,401,666 B2 3/2013 Skelton et al.
8,423,147 B2 4/2013 Alataris et al.
8,433,415 B2 4/2013 Leiter et al.
8,437,853 B2 5/2013 Inman et al.
8,452,421 B2 5/2013 Thenuwara et al.
8,469,971 B2 6/2013 Barker
8,504,138 B1 8/2013 Pivonka et al.
8,504,150 B2 8/2013 Skelton
8,538,541 B2 9/2013 Milojevic et al.
8,564,472 B2 10/2013 Okamura et al.
8,579,834 B2 11/2013 Davis et al.
8,612,015 B2 12/2013 Knifong, Sr.
8,620,435 B2 12/2013 Rooney et al.
8,626,297 B2 1/2014 Jaax et al.
8,626,314 B2 1/2014 Swoyer et al.
8,634,928 B1 1/2014 O'Driscoll et al.
8,655,451 B2 2/2014 Klosterman et al.
8,706,240 B2 4/2014 Bradley et al.
8,718,781 B2 5/2014 Alataris et al.
8,758,274 B2 6/2014 Sahasrabudhe et al.
8,774,927 B2 7/2014 Deridder
8,798,773 B2 8/2014 Mashiach
8,834,392 B2 9/2014 Panken et al.
8,874,217 B2 10/2014 Alataris et al.
8,880,177 B2 11/2014 Alataris et al.
8,880,191 B2 11/2014 Pyles et al.
8,886,327 B2 11/2014 Alataris et al.
8,886,328 B2 11/2014 Alataris et al.
8,897,870 B2 11/2014 De
8,903,502 B2 12/2014 Perryman et al.
8,934,981 B2 1/2015 De
8,954,165 B2 2/2015 Sharma et al.
8,972,502 B2 3/2015 Beslic et al.
9,020,590 B1 4/2015 Honeycutt et al.
9,031,664 B2 5/2015 Trier
9,044,612 B2 6/2015 Mashiach et al.
9,061,151 B2 6/2015 Mashiach et al.
9,106,203 B2 8/2015 Kesler et al.
9,138,582 B2 9/2015 Doan et al.
9,144,681 B2 9/2015 Decre et al.
9,149,210 B2 10/2015 Sahasrabudhe et al.
9,173,811 B2 11/2015 Greiner et al.
9,220,897 B2 12/2015 Perryman et al.
9,254,393 B2 2/2016 Perryman et al.
9,272,081 B2 3/2016 Cameron et al.
9,339,655 B2 5/2016 Carbunaru
9,393,420 B2 7/2016 Almendinger et al.
9,403,020 B2 8/2016 Wingeier
9,433,750 B2 9/2016 Pivonka et al.
9,440,084 B2 9/2016 Davis et al.
9,452,288 B2 9/2016 Whitehurst et al.
9,462,398 B2 10/2016 DeRidder
9,463,318 B2 10/2016 Mashiach et al.
9,533,155 B2 1/2017 Jiang et al.
9,555,248 B2 1/2017 De
9,555,257 B2 1/2017 Mashiach et al.

(56) References Cited

U.S. PATENT DOCUMENTS 9,585,642 B2 3/2017 Dinsmoor et al.
9,622,700 B2 4/2017 Sahasrabudhe et al.
9,623,245 B2 4/2017 King et al.
9,623,253 B2 4/2017 Perryman et al.
9,643,010 B2 5/2017 Ranu
9,656,077 B2 5/2017 De
9,656,085 B2 5/2017 Moffitt et al.
9,656,089 B2 5/2017 Yip et al.
9,707,406 B1 7/2017 Dellamano et al.
9,717,921 B2 8/2017 Perryman et al.
9,731,140 B1 8/2017 Perryman et al.
9,764,135 B2 9/2017 De
9,770,592 B2 9/2017 Lin et al.
9,789,314 B2 10/2017 Perryman et al.
9,789,321 B2 10/2017 Dixit et al.
9,826,963 B2 11/2017 Scott et al.
9,833,629 B2 12/2017 Dellamano et al.
9,893,423 B2 2/2018 Debray
9,913,975 B2 3/2018 Carbunaru et al.
9,919,159 B2 3/2018 Skelton et al.
9,993,646 B2 6/2018 Parramon et al.
10,004,635 B2 6/2018 Kahook
10,016,603 B2 7/2018 Sachs et al.
10,016,608 B2 7/2018 Peterson et al.
10,016,615 B2 7/2018 Simon et al.
10,016,627 B2 7/2018 Viitala et al.
10,022,549 B2 7/2018 Dellamano et al.
10,022,552 B2 7/2018 Stahler et al.
10,035,017 B2 7/2018 Thakkar et al.
10,035,020 B2 7/2018 Wang et al.
10,052,481 B2 8/2018 McClure et al.
10,076,668 B2 9/2018 De Ridder
10,086,201 B2 10/2018 Chang et al.
10,092,758 B2 10/2018 De Ridder
10,143,788 B2 12/2018 Rudser et al.
10,149,976 B1 12/2018 Andresen et al.
10,207,118 B2 2/2019 Skelton
10,238,872 B2 3/2019 Pivonka et al.
10,238,874 B2 3/2019 Perryman et al.
10,245,436 B2 4/2019 Perryman et al.
10,272,239 B1 4/2019 Andresen et al.
10,315,039 B2 6/2019 Perryman et al.
10,320,232 B2 6/2019 Pivonka et al.
10,328,265 B2 6/2019 Moffitt et al.
10,335,596 B2 7/2019 Yakovlev et al.
10,335,599 B2 7/2019 Zottola
10,411,760 B2 9/2019 Yakovlev et al.
10,420,947 B2 9/2019 Perryman et al.
10,471,262 B2 11/2019 Perryman et al.
10,471,268 B2 11/2019 Crosby et al.
10,644,539 B2 5/2020 Pivonka et al.
10,682,521 B2 6/2020 Jiang et al.
10,849,643 B2 12/2020 Castillo et al.
10,898,719 B2 1/2021 Pivonka et al.
10,967,183 B2 4/2021 Yakovlev et al.
11,018,721 B2 5/2021 Yakovlev et al.
11,090,491 B2 8/2021 Mishra et al.
11,097,096 B2 8/2021 Linden et al.
11,133,709 B2 9/2021 Pivonka et al.
11,160,980 B2 11/2021 Mishra et al.
11,260,236 B2 3/2022 Mathur et al.
11,318,315 B2 5/2022 Hartley et al.
11,331,493 B2 5/2022 Pivonka et al.
11,451,265 B2 9/2022 Yakovlev et al.
11,511,121 B2 11/2022 Sit et al.
11,633,151 B2 4/2023 Pivonka et al.
11,766,561 B2 9/2023 Mishra et al.
11,826,569 B2 11/2023 Mishra et al.
11,938,327 B2 3/2024 Hartley et al.
12,186,563 B2 1/2025 Yakovlev et al.
12,201,829 B2 1/2025 Linden et al.
12,390,650 B2 8/2025 Sit et al.
12,502,543 B2 12/2025 Pivonka et al.
12,533,517 B2 1/2026 Mishra et al.
12,551,710 B2 2/2026 Buddha et al.
2002/0014039 A1 2/2002 Merlet
2002/0111659 A1 8/2002 Davis et al.
2002/0140399 A1 10/2002 Echarri et al.
2003/0055406 A1 3/2003 Lebel et al.
2003/0135253 A1 7/2003 Kokones et al.
2004/0059392 A1 3/2004 Parramon et al.
2004/0093039 A1 5/2004 Schumert
2004/0119552 A1 6/2004 Wray
2004/0215287 A1 10/2004 Swoyer et al.
2004/0215306 A1 10/2004 Heil et al.
2005/0043765 A1 2/2005 Williams et al.
2005/0075696 A1 4/2005 Forsberg et al.
2005/0075699 A1 4/2005 Olson et al.
2005/0151696 A1 7/2005 Govari et al.
2005/0222656 A1 10/2005 Wahlstrand et al.
2005/0245989 A1 11/2005 Davis
2005/0278000 A1 12/2005 Strother et al.
2005/0288596 A1 12/2005 Eigler et al.
2006/0036273 A1 2/2006 Siegal
2006/0074450 A1 4/2006 Boveja et al.
2006/0095078 A1 5/2006 Tronnes
2006/0122653 A1 6/2006 Bradley et al.
2006/0149330 A1 7/2006 Mann et al.
2006/0190021 A1 8/2006 Hausman et al.
2006/0217782 A1 9/2006 Boveja et al.
2006/0224225 A1 10/2006 Ransbury et al.
2006/0247738 A1 11/2006 Schmeling et al.
2006/0265057 A1 11/2006 Greenberg et al.
2007/0021802 A1 1/2007 Heruth et al.
2007/0032734 A1 2/2007 Najafi et al.
2007/0038250 A1 2/2007 He et al.
2007/0100411 A1 5/2007 Bonde
2007/0123952 A1 5/2007 Strother et al.
2007/0142874 A1 6/2007 John
2007/0156205 A1 7/2007 Larson et al.
2007/0255368 A1 11/2007 Bonde et al.
2007/0270928 A1 11/2007 Erlebacher
2007/0288076 A1 12/2007 Bulkes et al.
2008/0045989 A1 2/2008 Welborn
2008/0055178 A1 3/2008 Kim
2008/0082147 A1 4/2008 Dai et al.
2008/0103569 A1 5/2008 Gerber
2008/0103570 A1 5/2008 Gerber
2008/0103578 A1 5/2008 Gerber
2008/0132981 A1 6/2008 Gerber
2008/0143619 A1 6/2008 Wotherspoon
2008/0146871 A1 6/2008 Arneson et al.
2008/0161803 A1 7/2008 Oral et al.
2008/0195128 A1 8/2008 Orbay et al.
2008/0214992 A1 9/2008 Haarala et al.
2008/0269591 A1 10/2008 Halperin et al.
2008/0300654 A1 12/2008 Lambert et al.
2008/0300656 A1 12/2008 Donders et al.
2008/0300660 A1 12/2008 John
2008/0319492 A1 12/2008 Katsnelson
2009/0045964 A1 2/2009 Takeda et al.
2009/0082829 A1 3/2009 Panken et al.
2009/0082835 A1 3/2009 Jaax et al.
2009/0171408 A1 7/2009 Solem
2009/0171420 A1 7/2009 Brown et al.
2009/0204170 A1 8/2009 Hastings et al.
2009/0224361 A1 9/2009 Liu et al.
2009/0248112 A1 10/2009 Mumbru et al.
2009/0275956 A1 11/2009 Burnes et al.
2009/0276015 A1 11/2009 Rondoni et al.
2009/0281597 A1 11/2009 Parramon et al.
2010/0010383 A1 1/2010 Skelton et al.
2010/0010392 A1 1/2010 Skelton et al.
2010/0069996 A1 3/2010 Strahl
2010/0076525 A1 3/2010 Skelton et al.
2010/0082087 A1 4/2010 Silipo et al.
2010/0125312 A1 5/2010 Stevenson et al.
2010/0161002 A1 6/2010 Aghassian et al.
2010/0168817 A1 7/2010 Yamamoto et al.
2010/0201368 A1 8/2010 Doerr et al.
2010/0204756 A1 8/2010 Aghassian
2010/0249888 A1 9/2010 Glenn et al.
2010/0274314 A1 10/2010 Alataris et al.
2010/0305663 A1 12/2010 Aghassian

(56) References Cited

U.S. PATENT DOCUMENTS

2010/0331925 A1* 12/2010 Peterson ............ A61N 1/36071 607/117
2011/0034886 A1 2/2011 Elbe et al.
2011/0046697 A1* 2/2011 Gerber ............... A61N 1/36071 703/2
2011/0054583 A1 3/2011 Litt et al.
2011/0060395 A1 3/2011 Cantlon
2011/0112610 A1 5/2011 Rahman et al.
2011/0172562 A1 7/2011 Sahasrabudhe et al.
2011/0172743 A1 7/2011 Davis et al.
2011/0184337 A1 7/2011 Evans et al.
2011/0224665 A1 9/2011 Crosby et al.
2011/0234155 A1 9/2011 Chen et al.
2011/0301670 A1 12/2011 Gross et al.
2011/0301687 A1 12/2011 Van
2012/0004708 A1 1/2012 Chen et al.
2012/0004709 A1 1/2012 Chen et al.
2012/0012630 A1 1/2012 Lui et al.
2012/0016439 A1 1/2012 Alataris et al.
2012/0029597 A1 2/2012 Keacher
2012/0035692 A1 2/2012 Cantlon et al.
2012/0179071 A1 7/2012 Skelton
2012/0185027 A1 7/2012 Pianca et al.
2012/0197352 A1 8/2012 Carbunaru et al.
2012/0228954 A1 9/2012 Kesler et al.
2012/0283800 A1 11/2012 Perryman et al.
2012/0296271 A1 11/2012 Yomtov et al.
2012/0296329 A1 11/2012 Ng
2012/0296444 A1 11/2012 Greenberg et al.
2013/0012866 A1 1/2013 Deem et al.
2013/0053767 A1 2/2013 Pivonka et al.
2013/0096642 A1 4/2013 Wingeier
2013/0096650 A1 4/2013 Aghassian
2013/0110194 A1 5/2013 Wei
2013/0150925 A1 6/2013 Vamos et al.
2013/0197609 A1 8/2013 Moore et al.
2013/0204321 A1 8/2013 Alataris et al.
2013/0215979 A1 8/2013 Yakovlev et al.
2013/0289637 A1 10/2013 Amely-Velez et al.
2013/0310706 A1 11/2013 Stone et al.
2013/0317564 A1 11/2013 Lin et al.
2013/0331638 A1 12/2013 Cameron et al.
2013/0345202 A1 12/2013 Amselem
2014/0018788 A1 1/2014 Engelman et al.
2014/0025140 A1 1/2014 Lui et al.
2014/0046413 A1 2/2014 Kane et al.
2014/0058467 A1 2/2014 Hamann et al.
2014/0094876 A1 4/2014 Wingeier et al.
2014/0100636 A1 4/2014 Mashiach et al.
2014/0107709 A1 4/2014 Schmitz et al.
2014/0107752 A1 4/2014 Parramon et al.
2014/0119552 A1 5/2014 Beaucoup
2014/0155973 A1 6/2014 Grigsby et al.
2014/0163338 A1 6/2014 Roesicke
2014/0163580 A1 6/2014 Tischendorf et al.
2014/0163638 A1 6/2014 Marnfeldt et al.
2014/0163645 A1 6/2014 Dinsmoor et al.
2014/0163646 A1 6/2014 Tischendorf et al.
2014/0172047 A1 6/2014 Spitaels et al.
2014/0180365 A1 6/2014 Perryman et al.
2014/0194771 A1 7/2014 Parker et al.
2014/0257428 A1 9/2014 Zhu et al.
2014/0275847 A1 9/2014 Perryman et al.
2014/0277281 A1 9/2014 Grandhe
2014/0277282 A1 9/2014 Jaax
2014/0288393 A1 9/2014 Grevious et al.
2014/0304773 A1 10/2014 Woods et al.
2014/0336727 A1 11/2014 Perryman et al.
2014/0346078 A1 11/2014 Chang
2014/0358197 A1 12/2014 Mashiach et al.
2014/0364919 A1 12/2014 Doan
2014/0371515 A1 12/2014 John
2015/0012057 A1 1/2015 Carlson et al.
2015/0018699 A1 1/2015 Zeng et al.
2015/0018728 A1 1/2015 Gross et al.
2015/0035378 A1 2/2015 Calhoun et al.
2015/0080982 A1 3/2015 Van Funderburk
2015/0100109 A1 4/2015 Feldman et al.
2015/0100110 A1 4/2015 Towe et al.
2015/0119673 A1 4/2015 Pellinen et al.
2015/0164401 A1 6/2015 Toth et al.
2015/0224326 A1 8/2015 Toth et al.
2015/0265842 A1 9/2015 Ridler et al.
2015/0290379 A1 10/2015 Rudser et al.
2015/0321000 A1 11/2015 Rosenbluth et al.
2015/0321002 A1 11/2015 Khalil et al.
2015/0335285 A1 11/2015 Poon et al.
2015/0380972 A1 12/2015 Fort
2016/0015411 A1 1/2016 Keller et al.
2016/0015980 A1 1/2016 Biele et al.
2016/0023006 A1 1/2016 Ridler et al.
2016/0023022 A1 1/2016 Zarins et al.
2016/0030666 A1 2/2016 Lozano et al.
2016/0036261 A1 2/2016 Lenive
2016/0045746 A1 2/2016 Jiang et al.
2016/0087687 A1 3/2016 Kesler et al.
2016/0106994 A1 4/2016 Crosby et al.
2016/0113671 A1 4/2016 Berger
2016/0121102 A1 5/2016 Tockman et al.
2016/0121124 A1 5/2016 Johanek et al.
2016/0135917 A1 5/2016 Mickle et al.
2016/0136438 A1 5/2016 Perryman et al.
2016/0136443 A1 5/2016 Grandhe et al.
2016/0144184 A1 5/2016 Marnfeldt
2016/0157769 A1 6/2016 Min et al.
2016/0199657 A1 7/2016 Jiang et al.
2016/0199658 A1 7/2016 Nassif et al.
2016/0218433 A1 7/2016 Nghiem et al.
2016/0331956 A1 11/2016 Yakovlev et al.
2016/0361545 A1 12/2016 Kaula et al.
2016/0375237 A1 12/2016 Hahn et al.
2017/0001003 A1 1/2017 Pivonka et al.
2017/0050021 A1 2/2017 Cosman, Sr.
2017/0054324 A1 2/2017 Pivonka et al.
2017/0054332 A1 2/2017 Pivonka et al.
2017/0087353 A1 3/2017 Thota et al.
2017/0095667 A1 4/2017 Yakovlev et al.
2017/0113046 A1 4/2017 Fried et al.
2017/0165491 A9 6/2017 De
2017/0189683 A1 7/2017 Perryman et al.
2017/0197082 A1 7/2017 Pang et al.
2017/0230084 A1 8/2017 Zhu et al.
2017/0239483 A1 8/2017 Mathur et al.
2017/0319855 A1 11/2017 Kramer et al.
2018/0028824 A1 2/2018 Pivonka et al.
2018/0064944 A1 3/2018 Grill et al.
2018/0070841 A1 3/2018 Honore et al.
2018/0071512 A1 3/2018 Feldman et al.
2018/0071536 A1 3/2018 Skelton et al.
2018/0083668 A1 3/2018 Yakovlev et al.
2018/0085593 A1 3/2018 Fayram et al.
2018/0090971 A1 3/2018 Graham et al.
2018/0140843 A1 5/2018 Kent et al.
2018/0169423 A1 6/2018 Perryman et al.
2018/0193651 A1 7/2018 Annoni et al.
2018/0200520 A1 7/2018 Tranchina et al.
2018/0214699 A1 8/2018 Kothandaraman et al.
2018/0214700 A1 8/2018 Vansickle et al.
2018/0236237 A1 8/2018 Kent et al.
2018/0243563 A1 8/2018 Vallejo et al.
2018/0256906 A1 9/2018 Pivonka et al.
2018/0289965 A1 10/2018 Nelson et al.
2018/0326220 A1 11/2018 Kaula et al.
2018/0333578 A1 11/2018 Mock et al.
2018/0345019 A1 12/2018 Greenberg et al.
2018/0368875 A1 12/2018 Castillo et al.
2018/0369573 A1 12/2018 Cholette et al.
2019/0001139 A1 1/2019 Mishra et al.
2019/0008556 A1 1/2019 Perryman et al.
2019/0009097 A1 1/2019 Hartley et al.
2019/0030339 A1 1/2019 Baru et al.
2019/0143124 A1 5/2019 Perryman et al.
2019/0151659 A1 5/2019 Mishra et al.
2019/0209844 A1 7/2019 Esteller et al.

(56) References Cited

U.S. PATENT DOCUMENTS

| | | | |
|---|---|---|---|
| 2019/0247198 | A1 | 8/2019 | Zellmer et al. |
| 2019/0262610 | A1 | 8/2019 | Kent et al. |
| 2019/0269913 | A1 | 9/2019 | Pivonka et al. |
| 2019/0366094 | A1 | 12/2019 | Esteller et al. |
| 2019/0374776 | A1 | 12/2019 | Mishra et al. |
| 2019/0388692 | A1 | 12/2019 | Dinsmoor et al. |
| 2020/0038660 | A1 | 2/2020 | Torgerson |
| 2020/0101291 | A1 | 4/2020 | Yakovlev et al. |
| 2020/0132434 | A1 | 4/2020 | Riahi et al. |
| 2020/0139138 | A1 | 5/2020 | Sit et al. |
| 2020/0147388 | A1 | 5/2020 | Huertas Fernandez et al. |
| 2020/0204209 | A1 | 6/2020 | Yakovlev et al. |
| 2020/0206511 | A1 | 7/2020 | Goedeke et al. |
| 2020/0222000 | A1 | 7/2020 | Poon et al. |
| 2020/0305745 | A1 | 10/2020 | Wagenbach et al. |
| 2020/0306528 | A1 | 10/2020 | Linden et al. |
| 2020/0398058 | A1 | 12/2020 | Pivonka et al. |
| 2021/0099015 | A1 | 4/2021 | Pivonka et al. |
| 2021/0187300 | A1 | 6/2021 | Dinsmoor et al. |
| 2021/0196957 | A1 | 7/2021 | Yakovlev et al. |
| 2021/0330981 | A1 | 10/2021 | Mishra et al. |
| 2021/0399765 | A1 | 12/2021 | Yakovlev et al. |
| 2022/0016103 | A1 | 1/2022 | Baltcheva et al. |
| 2022/0016430 | A1 | 1/2022 | Hartley et al. |
| 2022/0072300 | A1 | 3/2022 | Yakovlev et al. |
| 2022/0080189 | A1 | 3/2022 | Mishra et al. |
| 2022/0118251 | A1 | 4/2022 | Buddha et al. |
| 2022/0126103 | A1 | 4/2022 | Pivonka et al. |
| 2022/0134108 | A1 | 5/2022 | Dinsmoor et al. |
| 2022/0176108 | A1 | 6/2022 | Linden et al. |
| 2022/0176120 | A1 | 6/2022 | Kulkarni et al. |
| 2022/0176133 | A1 | 6/2022 | Buddha et al. |
| 2022/0218994 | A1 | 7/2022 | Mishra et al. |
| 2022/0263346 | A1 | 8/2022 | Pivonka et al. |
| 2023/0029600 | A1 | 2/2023 | Pivonka et al. |
| 2023/0129373 | A1 | 4/2023 | Sit et al. |
| 2023/0146724 | A1 | 5/2023 | Debock et al. |
| 2024/0041399 | A1 | 2/2024 | Pivonka |
| 2024/0050747 | A1 | 2/2024 | Mishra et al. |
| 2024/0050758 | A1 | 2/2024 | Castillo et al. |
| 2024/0139517 | A1 | 5/2024 | Mishra |
| 2024/0226548 | A1 | 7/2024 | Mishra et al. |
| 2024/0307687 | A1 | 9/2024 | Mishra et al. |
| 2025/0158657 | A1 | 5/2025 | Yakovlev et al. |
| 2025/0213872 | A1 | 7/2025 | Pivonka et al. |
| 2025/0325812 | A1 | 10/2025 | Yakovlev et al. |
| 2025/0332408 | A1 | 10/2025 | Linden et al. |

FOREIGN PATENT DOCUMENTS

| | | | |
|---|---|---|---|
| EP | 1609501 | A1 | 12/2005 |
| EP | 2155330 | B1 | 10/2014 |
| WO | WO-9500203 | A1 | 1/1995 |
| WO | WO-2005105201 | A2 | 11/2005 |
| WO | WO-2007051146 | A1 | 5/2007 |
| WO | WO-2007068284 | A1 | 6/2007 |
| WO | WO-2008066556 | A1 | 6/2008 |
| WO | WO-2010051062 | A1 | 5/2010 |
| WO | WO-2010062517 | A1 | 6/2010 |
| WO | WO-2013035092 | A2 | 3/2013 |
| WO | WO-2014071079 | A1 | 5/2014 |
| WO | WO-2014089299 | A2 | 6/2014 |
| WO | WO-2014153124 | A1 | 9/2014 |
| WO | WO-2014153219 | A1 | 9/2014 |
| WO | WO-2014153228 | A1 | 9/2014 |
| WO | WO-2014205129 | A1 | 12/2014 |
| WO | WO-2015081231 | A1 | 6/2015 |
| WO | WO-2015139053 | A1 | 9/2015 |
| WO | WO-2015196164 | A2 | 12/2015 |
| WO | WO-2015196164 | A3 | 2/2016 |
| WO | WO-2016028608 | A1 | 2/2016 |
| WO | WO-2016113832 | A1 | 7/2016 |
| WO | WO-2016127130 | A1 | 8/2016 |
| WO | WO-2016205373 | A1 | 12/2016 |
| WO | WO-2017044904 | A1 | 3/2017 |
| WO | WO-2017142948 | A1 | 8/2017 |
| WO | WO-2017165410 | A1 | 9/2017 |
| WO | WO-2017205675 | A1 | 11/2017 |
| WO | WO-2018017463 | A1 | 1/2018 |
| WO | WO-2018023057 | A1 | 2/2018 |
| WO | WO-2018126062 | A1 | 7/2018 |
| WO | WO-2018144631 | A1 | 8/2018 |
| WO | WO-2018156953 | A1 | 8/2018 |
| WO | WO-2018170141 | A1 | 9/2018 |
| WO | WO-2018208992 | A1 | 11/2018 |
| WO | WO-2019226557 | A1 | 11/2019 |
| WO | WO-2019226568 | A1 | 11/2019 |
| WO | WO-2020070492 | A1 | 4/2020 |
| WO | WO-2021003439 | A1 | 1/2021 |
| WO | WO-2021067873 | A1 | 4/2021 |
| WO | WO-2021133947 | A1 | 7/2021 |
| WO | WO-2021262762 | A1 | 12/2021 |
| WO | WO-2022047077 | A1 | 3/2022 |
| WO | WO-2022103774 | A1 | 5/2022 |
| WO | WO-2022197748 | A1 | 9/2022 |
| WO | WO-2023283568 | A1 | 1/2023 |
| WO | WO-2025158408 | A1 | 7/2025 |

OTHER PUBLICATIONS

Butson, C. et al., "Current steering to Control the Volume of Tissue Activated During Deep Brain Stimulation" Brain Stimul. (2008) (1): 7-15.

Cardador, L., "Review of Existing, Mounted Targeting Devices for Distal Locking of Intramedullary Nails," Practice of Intramedullary Locked Nails, Jan. 1, 2006, pp. 265-270.

Crosby D N, et al., "Burst and Tonic Spinal Cord Stimulation Differentially Activate GABAergic Mechanisms to Attenuate Pain in a Rat Model of Cervical Radiculopathy", IEEE Transactions on Biomedical Engineering, Jun. 2015, vol. 62 No. 6, pp. 1604-1613.

EP14813206 Examination Report dated Apr. 23, 2020. 2 pages.

EP15809379.9 European Search Report dated Mar. 9, 2018. 7 pages.

European Search Report and Written Opinion in EP Application No. 16845235.7, mailed Apr. 24, 2019, 8 pages.

European Search Report and Written Opinion in EP Application No. 13852295.8, mailed May 12, 2016, 10 pages.

European Search Report and Written Opinion in EP Application No. 16747389.1, mailed Jul. 5, 2018, 8 pages.

European Search Report and Written Opinion in EP Application No. 17770982.1, mailed Sep. 26, 2019, 7 pages.

European Search Report and Written Opinion in EP Application No. 17803620.8, mailed Oct. 30, 2019, 8 pages.

European Search Report and Written Opinion in EP Application No. 17831624.6, mailed Feb. 20, 2020, 9 pages.

European Search Report and Written Opinion in EP Application No. 17887576.1, mailed Oct. 9, 2020, 8 pages.

European Search Report and Written Opinion in EP Application No. 18797777.2, mailed Jan. 14, 2021, 7 pages.

European Search Report and Written Opinion in EP Application No. 20212248.7, mailed Apr. 12, 2021, 9 pages.

Extended European Search Report for European Application No. EP23186171.7 dated Jan. 5, 2024, 7 pages.

Extended European Search Report mailed on Jan. 3, 2024, for EP Application No. 20871125.9, 15 pages.

Final Office Action for U.S. Appl. No. 16/111,868 mailed on Mar. 11, 2021, 24 pages.

Final Office Action for U.S. Appl. No. 17/379,928 dated Jul. 17, 2023, 13 pages.

Final Office Action for U.S. Appl. No. 16/222,959 mailed on Nov. 21, 2022, 21 pages.

Final Office Action mailed on Aug. 18, 2023, for U.S. Appl. No. 17/240,629, filed Apr. 26, 2021, 11 pages.

Final Office Action mailed on Nov. 1, 2023, for U.S. Appl. No. 17/726,378, filed Apr. 21, 2022, 15 pages.

Final Office Action for U.S. Appl. No. 18/046,042 dated Apr. 15, 2024, 14 pages.

(56) References Cited

OTHER PUBLICATIONS

He S, et al., The Electrically Evoked Compound Action Potential: From Laboratory to Clinic, Frontiers in Neuroscience, vol. 11, Jun. 2017, pp. 1-20.
International Search Report and Written Opinion for PCT/US2014/043023; Oct. 6, 2014, 13 pages.
International Search Report and Written Opinion for PCT/US2016/016888, Apr. 14, 2016, 8 pages.
International Search Report and Written Opinion for PCT/US2016/051177, Nov. 10, 2016, 18 pages.
International Search Report and Written Opinion for PCT/US2017/023400, May 23, 2017, 8 pages.
International Search Report and Written Opinion for PCT/US2017/042351, Sep. 26, 2017, 9 pages.
International Search Report and Written Opinion for PCT/US2017/068803, Mar. 6, 2018, 9 pages.
International Search Report and Written Opinion for PCT/US2018/031904, Jul. 26, 2018, 10 pages.
International Search Report and Written Opinion for PCT/US2020/054150, Jan. 6, 2021, 11 pages.
International Search Report and Written Opinion for PCT/US2020/066901, Mar. 15, 2021, 7 pages.
International Search Report and Written Opinion for PCT/US2021/038545, Mar. 15, 2021, 7 pages.
International Search Report and Written Opinion mailed on Jan. 31, 2022 for PCT/US2021/058673, 8 pages.
International Search Report and Written Opinion mailed on May 18, 2022, for PCT Application No. PCT/US2022/020452, filed Mar. 15, 2022, 8 pages.
Non-Final Office Action for U.S. Appl. No. 14/975,358 dated Aug. 8, 2019. 12 pages.
Non-Final Office Action for U.S. Appl. No. 16/111,868 mailed on Jul. 8, 2021, 30 pages.
Non-Final Office Action for U.S. Appl. No. 17/379,928 dated Jan. 29, 2024, 16 pages.
Non-Final Office Action for U.S. Appl. No. 17/384,020 dated Jan. 23, 2024, 28 pages.
Non-Final Office Action for U.S. Appl. No. 17/412,044 dated Feb. 2, 2024, 12 pages.
Non-Final Office Action for U.S. Appl. No. 17/726,378 dated Apr. 14, 2023, 15 pages.
Non-Final Office Action for U.S. Appl. No. 18/046,042 dated Aug. 23, 2023, 13 pages.
Non-Final Office Action mailed on Feb. 1, 2024, for U.S. Appl. No. 17/081,351, filed Oct. 27, 2020, 13 pages.
Non-Final Office Action mailed on Feb. 24, 2023, for U.S. Appl. No. 17/240,629, filed Apr. 26, 2021, 12 pages.
Non-Final Office Action mailed on Mar. 22, 2023, for U.S. Appl. No. 17/489,580, filed Sep. 29, 2021, 16 pages.
Notice of Allowance for U.S. Appl. No. 16/222,959 dated May 22, 2023, 11 pages.
Notice of Allowance for U.S. Appl. No. 17/489,580 dated Nov. 22, 2023, 9 pages.
Office Action dated Oct. 20, 2017 for U.S. Appl. No. 15/264,864, 14 pages.
Partial Supplementary European Search Report mailed on Sep. 18, 2023, for EP Application No. 20871125.9, 14 pages.
PCT/US2017/034553 International Search Report and Written Opinion dated Oct. 10, 2017, 9 pages.
U.S. Appl. No. 63/082,856, inventors Lakshmi; Narayan Mishra et al., filed Sep. 24, 2020. 131 pages.
U.S. Appl. No. 14/975,358 Office Action dated Dec. 5, 2019, 9 pages.
U.S. Appl. No. 14/975,358 Office Action dated Jul. 27, 2020, 12 pages.
U.S. Appl. No. 14/975,358 Office Action dated May 15, 2018, 9 pages.
U.S. Appl. No. 14/975,358 Office Action dated Nov. 2, 2020, 18 pages.
U.S. Appl. No. 14/975,358 Office Action dated Nov. 20, 2018, 9 pages.
U.S. Appl. No. 15/664,231 Office Action dated Aug. 6, 2020, 14 pages.
U.S. Appl. No. 15/664,231 Office Action dated Jan. 24, 2020, 15 pages.
U.S. Appl. No. 15/664,231 Office Action dated Jul. 10, 2020, 14 pages.
U.S. Appl. No. 15/664,231 Office Action dated Mar. 8, 2021, 25 pages.
U.S. Appl. No. 16/672,921 Notice of Allowance dated Apr. 23, 2021, 7 pages.
U.S. Appl. No. 16/672,921 Office Action dated Feb. 16, 2021, 10 pages.
U.S. Appl. No. 16/672,921 Office Action dated Mar. 22, 2021, 11 pages.
Wheatley D, et al., "Electrically Evoked Compound Action Potential (ECAP) Stimulus-Artefact (SA) Blanking Low-Power Low-Noise CMOS Amplifier", 50th Midwest Symposium on Circuits and Systems, 2007, pp. 41-44.
Yakovlev, Anatoly et al., "Implantable Biomedical Devices: Wireless powering and communication," IEEE Communications Magazine, IEEE Service Center, vol. 50, No. 4, Apr. 1, 2012, pp. 152-159.
EP Application No. 21827905.7, Extended European Search Report mailed Jun. 18, 2024; Applicant Nalu Medical, Inc.; 5 pages.
EP Application No. 21862769.3, Extended European Search Report mailed Jul. 25, 2024; Applicant Nalu Medical, Inc.; 6 pages.
EP Application No. 21892687.1, Extended European Search Report mailed Sep. 18, 2024; Applicant Nalu Medical, Inc., 6 pages.
EP Application No. 22772095.0, Extended European Search Report mailed Dec. 23, 2024; Applicant Nalu Medical, Inc.; 9 pages.
EP Application No. 24157465.6, Extended European Search Report mailed Jun. 27, 2024; Applicant Nalu Medical, Inc.; 7 pages.
EP Application No. 24188096.2, Extended European Search Report mailed Nov. 29, 2024; Applicant Nalu Medical, Inc.; 10 pages.
EP Application No. 25170468.0, Extended European Search Report mailed Aug. 21, 2025; Applicant Nalu Medical, Inc.; 7 pages.
PCT Application No. PCT/IB2025/050854, International Search Report and Written Opinion mailed May 16, 2025; Applicant Nalu Medical, Inc.; 24 pages.
PCT Application No. PCT/IB2025/050854, Invitation to Pay Additional Fees mailed Mar. 28, 2025; Applicant Nalu Medical, Inc.; 2 pages.
Stack Exchange, "Can the saturation of an OPA influence its input?" (Jun. 6, 2015); [retrieved from Internet on Jul. 15, 2025 at https://electronics.stackexchange.com/questions/174179/can-the-saturation-of-an-opa-influence-its-input] ; 2 pages.
U.S. Appl. No. 16/120,139, Non-Final Office Action mailed Mar. 26, 2020; Inventor Castillo, Andre et al.; 27 pages.
U.S. Appl. No. 16/120,139, Notice of Allowance mailed Jul. 28, 2020; Inventor Castillo, Andre et al.; 10 pages.
U.S. Appl. No. 17/081,351, Final Office Action mailed Dec. 5, 2025; Inventor Castillo, Andre et al.; 14 pages.
U.S. Appl. No. 17/081,351, Final Office Action mailed Oct. 24, 2024; Inventor Castillo, Andre et al.; 9 pages.
U.S. Appl. No. 17/081,351, Non-Final Office Action mailed May 8, 2025; Inventor Castillo, Andre et al.; 6 pages.
U.S. Appl. No. 17/379,928, Notice of Allowance mailed Sep. 18, 2024; Inventor Linden, Christopher et al.; 7 pages.
U.S. Appl. No. 17/383,972, Non-Final Office Action mailed Dec. 3, 2024; Inventor Kulkarni, Gaurav Gajanan et al.; 23 pages.
U.S. Appl. No. 17/383,985, Non-Final Office Action mailed Dec. 27, 2024; Inventor Mishra, Lakshmi Narayan et al.; 14 pages.
U.S. Appl. No. 17/384,020, Final Office Action mailed Oct. 11, 2024; Inventor Buddha, Rushidev et al.; 36 pages.
U.S. Appl. No. 17/726,378, Ex Parte Quayle Action mailed May 29, 2025; Inventor Pivonka, Daniel et al; 5 pages.
U.S. Appl. No. 17/726,378, Final Office Action mailed Dec. 16, 2024; Inventor Pivonka, Daniel et al.; 15 pages.
U.S. Appl. No. 17/726,378, Non-Final Office Action mailed May 20, 2024; Inventor Pivonka, Daniel et al.;11 pages.
U.S. Appl. No. 17/726,378, Notice of Allowance mailed Aug. 26, 2025; Inventor Pivonka, Daniel et al.; 7 pages.

(56) References Cited

OTHER PUBLICATIONS

U.S. Appl. No. 18/046,042, Non-Final Office Action mailed Nov. 18, 2024; Inventor Sit, Ji-Jon et al.; 15 pages.
U.S. Appl. No. 18/046,042, Notice of Allowance mailed Apr. 30, 2025; Inventor Sit, Ji-Jon et al.; 5 pages.
U.S. Appl. No. 18/174,557, Non-Final Office Action mailed Sep. 10, 2025; Inventor Mishra, Lakshmi Narayan et al.; 9 pages.
U.S. Appl. No. 18/314,624, Non-Final Office Action mailed Jul. 1, 2025, Inventor Mishra, Lakshmi Narayan et al.; 9 pages.
U.S. Appl. No. 18/453,154, Non-Final Office Action mailed Oct. 16, 2025; Inventor Mishra, Lakshmi Narayan et al.; 9 pages.
U.S. Appl. No. 18/583,698, Notice of Allowance mailed Feb. 11, 2026; Inventor Hartley, Lee Fason et al.; 10 pages.
U.S. Appl. No. 19/399,426, filed Nov. 24, 2025; Inventor Pivonka, Daniel et al.
Wikipedia, "Negative-feedback amplifier" (publication date unknown); [Retrieved from Internet on Jul. 24, 2025 at https://en.wikipedia.org/wiki/Negative-feedback_amplifier]; 8 pages.

* cited by examiner

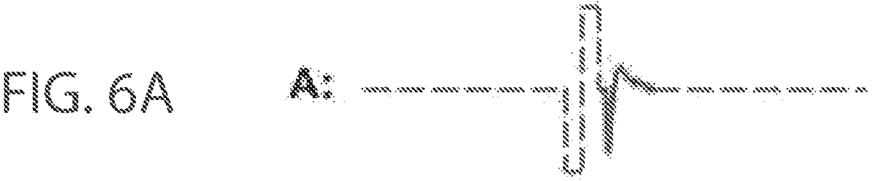
FIG. 6A
FIG. 6B
B:
FIG. 6C
(A +B )/2:
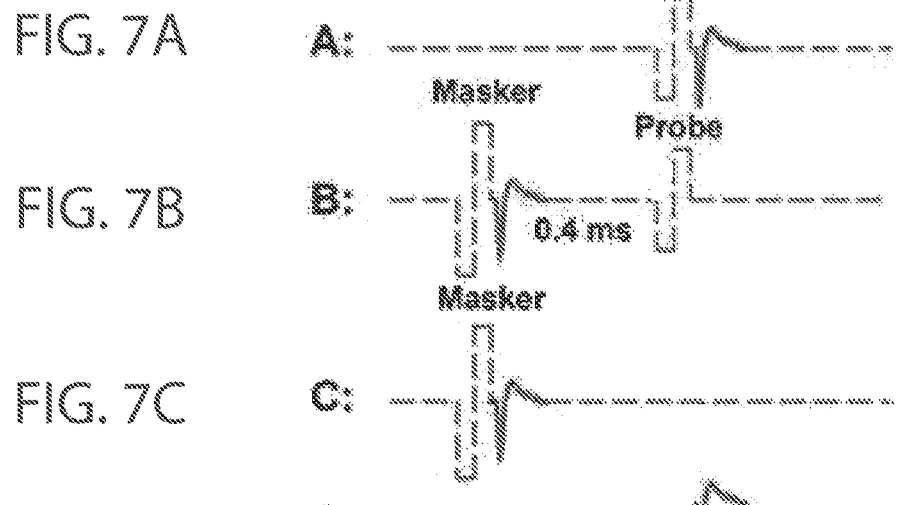
FIG. 7A
FIG. 7B
FIG. 7C
FIG. 7D
A-(B-C):

A:
a

B:
b

B - (b/a)*A

Area 1
Area 2

Area 1
Area 2

Area 1
Area 2

Area 1
Area 2

A schematic showing geometry of fascicles and nerve fibers within a nerve bundle Never fibers in a fascicle treated as parallel conductors A square cross-section of Aα nerve fibers considered for computing effective radial conductivity. Packing fraction is 70%.

Axial conductivity as a function of packing fraction

Radial conductivity as a function of packing fraction for group A nerve fibers

Simulation geometry for electrodes at 1mm from nerve bundle

Stimulation geometry for source electrode at 15mm from nerve bundle

Potential field (V) along cross-section passing through axis of fasicle 1 of geometry in Figure 11F Q(x) along center line of fascicles for source and ground electrodes placed at 1mm from nerve bundle Comparison of Q(x) at center line of fascicles for source electrodes at 15mm from nerve bundle Simulation model geometry with four fasicles in a nerve bundle Top view of a simulation model geometry with four fascicle in a nerve bundle Top view of a simulation model geometry with one fascicle in a nerve bundle Q(X) values at center line of 4th fascicle in fascicle distribution experiments Simulation model geometry for analysing current through nerve bundle Ratio of current increment versus distance of electrode from nerve budle Spatial Distribution Density along Nerve Bundle Circumference

APPARATUS FOR DELIVERING ENHANCED STIMULATION WAVEFORMS

RELATED APPLICATIONS

The present application is a continuation of International PCT Application No. PCT/US2022/020452 titled "Apparatus for Delivering Enhanced Stimulation Waveforms", filed Mar. 15, 2022, which claims priority to United States Provisional Patent Application No. 63/161,757, titled "Apparatus for Delivering Enhanced Stimulation Waveforms", filed Mar. 16, 2021, and United States Provisional Patent Application No. 63/273,068, titled "Apparatus for Delivering Enhanced Stimulation Waveforms", filed Oct. 28, 2021, the contents of each of which is incorporated herein by reference in its entirety for all purposes.

The subject matter of this application is related to that in: U.S. patent application Ser. No. 16/222,959, titled "Methods and Systems for Treating Pelvic Disorders and Pain Conditions", filed Dec. 17, 2018; U.S. patent application Ser. No. 16/266,822, titled "Method and Apparatus for Versatile Minimally Invasive Neuromodulators", filed Feb. 4, 2019; U.S. patent application Ser. No. 16/453,917, titled "Stimulation Apparatus", filed Jun. 26, 2019; U.S. patent application Ser. No. 16/505,425, titled "Wireless Implantable Sensing Devices", filed Jul. 8, 2019; U.S. patent application Ser. No. 16/993,999, titled "Apparatus for Peripheral or Spinal Stimulation", filed Aug. 14, 2020; U.S. patent application Ser. No. 17/081,351, titled "Methods and Systems for Insertion and Fixation of Implantable Devices", filed Oct. 27, 2020; U.S. patent application Ser. No. 17/187,654, titled "Method and Apparatus for Neuromodulation Treatments of Pain and Other Conditions", filed Feb. 26, 2021; U.S. patent application Ser. No. 17/240,629, titled "Method and Apparatus for Minimally Invasive Implantable Modulators", filed Apr. 26, 2021; U.S. patent application Ser. No. 17/372,095, titled "Apparatus with Enhanced Stimulation Waveforms", filed Jul. 9, 2021; U.S. patent application Ser. No. 17/379,928, titled "Stimulation Apparatus", filed Jul. 19, 2021; U.S. patent application Ser. No. 17/383,915, titled "Stimulation Apparatus", filed Jul. 23, 2021; U.S. patent application Ser. No. 17/383,972, titled "Systems with Implanted Conduit Tracking", filed Jul. 23, 2021; U.S. patent application Ser. No. 17/383,985, titled "Stimulation Energy Systems with Current Steering", filed Jul. 23, 2021; U.S. patent application Ser. No. 17/384,020, titled "Stimulation Apparatus", filed Jul. 23, 2021; U.S. patent application Ser. No. 17/412,044, titled "Medical Apparatus Including an Implantable System and an External System", filed Aug. 25, 2021; International PCT Patent Application Serial Number PCT/US2021/047815, titled "Apparatus for Delivering Customized Stimulation Waveforms", filed Aug. 26, 2021; U.S. patent application Ser. No. 17/487,535, titled "Apparatus with Sequentially Implanted Stimulators", filed Sep. 28, 2021; U.S. patent application Ser. No. 17/489,580, titled "Devices and Methods for Positioning External Devices in Relation to Implanted Devices", filed Sep. 29, 2021; and International PCT Patent Application Serial Number PCT/US2021/058673, titled "Apparatus for Delivering Enhanced Stimulation Waveforms", filed Nov. 9, 2021; the contents of each of which is incorporated herein by reference in its entirety for all purposes.

BACKGROUND OF THE INVENTION

Field of the Invention

The present invention relates generally to medical apparatus for a patient, and in particular, apparatus that deliver enhanced stimulation to effectively deliver a therapy while avoiding undesired effects.

Background

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g., to treat pain). Most implants are relatively large devices with batteries and long conduits, such as implantable leads configured to deliver electrical energy or implantable tubes (i.e., catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices, and methods that provide one or more implantable devices and are designed to provide enhanced treatment of pain and other enhanced benefits.

SUMMARY

According to an aspect of the present inventive concepts, a medical apparatus for a patient comprises: an external system configured to transmit one or more transmission signals, each transmission signal comprising at least power or data; and an implantable system configured to receive the one or more transmission signals from the external system. The external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable stimulation element configured to deliver stimulation energy to the patient; an implantable controller configured to control the stimulation energy delivered to the at least one implantable stimulation element; an implantable energy storage assembly configured to provide power to an element selected from the group consisting of the at least one implantable stimulation element; the implantable controller; the implantable receiver; and combinations thereof; and an implantable housing surrounding at least the implantable controller and the implantable receiver.

In some embodiments, the first external device comprises an external surface that is void of movement-activated controls. The first external device can comprise a sensor configured to detect a tap of an operator.

In some embodiments, the at least one stimulation element comprises multiple stimulation elements, and the first implantable device comprises one or more leads that each comprise one or more of the stimulation elements, and the apparatus is configured to measure one or more eCAPs and produce eCAP data, and the apparatus is configured to use the eCAP data to identify an implant location for the one or more leads within the patient.

In some embodiments, the apparatus further comprises an imaging device comprising a fluoroscope and/or other X-ray imaging device that produces image data, and the at least one stimulation element comprises multiple stimulation elements, and the first implantable device comprises one or more leads that each comprise one or more of the stimulation elements, and the apparatus is configured to measure one or more eCAPs and produce eCAP data based on the measurements, and the apparatus is configured to identify an implant location for the one or more leads within the patient based on the eCAP data and the image data.

In some embodiments, the apparatus is configured to perform eCAP measurements, and the apparatus further comprises a controller and a memory coupled to the controller, wherein the memory stores instructions for the controller to perform an algorithm, and wherein the algorithm is configured to optimize the placement of the at least one implantable stimulation element in a stimulation area of interest. The algorithm can be configured to identify a low amplitude stimulation that achieves a high eCAP response. The at least one implantable stimulation element can comprise multiple stimulation elements positioned on one or more implantable leads, and the algorithm can be configured to identify an implant location for the one or more implantable leads based on the best average eCAP response over two or more of the stimulation elements. The algorithm can be configured to select an implant location based on multiple potential implant locations entered by an operator of the apparatus.

In some embodiments, the apparatus comprises a controller and a memory coupled to the controller, wherein the memory stores instructions for the controller to perform an algorithm, and wherein the algorithm is configured to automatically set one or more stimulation settings (also referred to as "stimulation parameter settings" or "stimulation parameters") that are based on a measurement performed by an operator of the apparatus. The algorithm can automatically set the one or more stimulation parameter settings based on one or more measured stimulation thresholds. The algorithm can automatically set the one or more stimulation parameter settings based on a paresthesia threshold and/or other maximum level of stimulation.

In some embodiments, the apparatus comprises a user interface configured to allow an operator to cause the apparatus to transition between an automatic stimulation parameter settings mode and a manual stimulation parameter settings mode.

In some embodiments, the apparatus comprises a controller and a memory coupled to the controller, wherein the memory stores instructions for the controller to perform an algorithm, and wherein the algorithm is configured to determine the stimulation parameter settings automatically when operating in the automatic stimulation parameter settings mode.

In some embodiments, the apparatus is configured to measure one or more eCAPs, and the apparatus comprises a user interface configured to provide a real-time display of the measured one or more eCAPs. The apparatus can be configured to perform a masker pulse artefact cancellation including delivery of a masker pulse, and the user interface can be configured to provide information related to generation of an eCAP due to the delivery of the masker pulse. The apparatus can be configured to perform a scaled template artefact cancellation including delivery of a template pulse, and the user interface can be configured to provide information related to generation of an eCAP due to the delivery of the template pulse.

In some embodiments, the apparatus is configured to measure multiple eCAPs, and the apparatus comprises a user interface configured to provide updates of the measured multiple eCAPs. The apparatus can be configured to allow an operator to set the number of eCAP measurements to be performed prior to providing an update. The apparatus can be configured to allow an operator to set the number of updates per second. The apparatus can be configured to operate in an automatic mode of eCAP detection. The apparatus can be further configured to allow an operator to manually identify the presence of an eCAP.

In some embodiments, the apparatus is configured to record eCAPs using one or more recording options selected from the group consisting of: all raw traces; eCAP response raw traces; individual traces averaged; averaged eCAPs; features such as N1-P2 magnitude; N1 latency; late response; one-shot mode; circular mode; event mode; and combinations thereof. The apparatus can be configured to record eCAPs using event mode, and event mode can comprise a capture that is triggered by: patient posture; patient activity; and/or another patient parameter.

In some embodiments, the apparatus is configured to perform a live playback method of making eCAP measurements, and the apparatus is further configured to make eCAP measurements using alternating polarity methods and/or masker pulse methods.

In some embodiments, the apparatus is configured to perform live playback and alternating polarity methods to make eCAP measurements. The apparatus can be configured to perform the eCAP measurements during standalone use. The apparatus can be configured to deliver tonic stimulation to multiple target areas, and the target area to be measured is: fixed; round-robin; and/or round robin with a dwell time.

In some embodiments, the apparatus is configured to deliver one or more stimulation paradigms that are based on one, two, three, and/or all of the following four factors: conductivity of fascicles based on packing fraction and/or nerve fiber type; impact of effective conductivity values on linear activation function values; impact of fascicle distribution on an activation function; total current passing through a nerve; and combinations of these.

In some embodiments, the apparatus is configured to steer current to a first set of one or more fibers of a nerve bundle while avoiding delivery of current to other fibers of the nerve bundle.

In some embodiments, the apparatus further comprises a user interface configured to provide a graphical representation of the patient's anatomy, and the apparatus is configured to allow a user to select a focus location within the graphical representation into which stimulation current delivered by the apparatus can be steered.

In some embodiments, the at least one stimulation element comprises multiple stimulation elements, and the implantable system comprises two leads, each lead comprising at least one of the multiple stimulation elements, and the apparatus further comprises a user interface configured to allow a user to specify a stagger and a separation of the two leads, and to specify a focus point into which current can be steered.

In some embodiments, the at least one stimulation element comprises multiple electrodes, each electrode capable of being configured as an anode or a cathode, and the apparatus further comprises a user interface that provides graphical representations of the multiple electrodes, and the apparatus is configured to operate in a manual current steering mode in which a user selects via the user interface anodes, cathodes, and/or a percentage of stimulation current allocation for each selected anode and/or cathode. The user interface can be configured to allow a user to draw a geometric shape between the graphical representations of the multiple electrodes. The geometric shape can determine which of the multiple electrodes are configured as anodes. A user-selected point within the geometric shape can be used to adjust the proportion of current assigned to each of the electrodes. The user-selected point within the geometric shape can be used to adjust the proportion of current assigned to each anode and/or cathode.

In some embodiments, the apparatus is configured to operate in a manual current steering mode and an automatic current steering mode, and the apparatus is configured to set a stimulation amplitude for the automatic current steering mode based on a stimulation amplitude, rate, and/or pulse width that was used in a previous manual current steering mode.

In some embodiments, the apparatus further comprises a user interface, and the user interface is configured to differentiate anatomical locations that have received stimulation energy from anatomical locations that have not received stimulation energy. The apparatus can be configured to store stimulation parameters associated with anatomical locations that have received stimulation energy.

In some embodiments, the system is configured to modify a stimulation amplitude of a stimulation energy delivered to a target location if pulse width and/or rate have changed for energy delivered to the target location. The stimulation amplitude modification can be configured to maintain charge based on stimulation energy delivered to a neighboring target location. The apparatus can further comprise a user interface, and the neighboring target location can be defined via the user interface. Horizontal spacing and/or vertical stagger resolution can be used to determine a distance to the neighboring target location.

In some embodiments, the apparatus is configured to allow a user to set a stimulation amplitude upon selection of a new target location to receive stimulation energy. The apparatus can further suggest a value for the stimulation amplitude selection, and the suggested value can comprise a threshold amplitude that was recorded for a neighboring target location and/or an amplitude that is equal to half of the most recent working amplitude.

In some embodiments, the apparatus is configured to dynamically update the current target location.

In some embodiments, the apparatus is configured to dynamically update stored working stimulation amplitude and stimulation element configurations upon user selection of a previously stimulated target location where the pulse width and/or rate match the most recently stimulated target location.

In some embodiments, the apparatus is configured to dynamically update stored working stimulation amplitude and stimulation element configurations upon user selection of a previously stimulated target location where the pulse width and/or rate do not match the most recently stimulated target location. The apparatus can be configured to require the user to set a stimulation amplitude, and the apparatus can be configured to suggest a value of the stimulation amplitude based on the previous and current target locations.

In some embodiments, the apparatus is configured to clear stored target locations and reset the stimulation amplitude if a lead configuration stagger or horizontal spacing is modified. The apparatus can be configured to notify the user of the clearing and resetting.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 6A-6C illustrate waveforms associated with an alternating polarity method of artefact cancellation, consistent with the present inventive concepts.

FIGS. 7A-7D illustrate waveforms associated with a masker-probe method of artefact cancellation, consistent with the present inventive concepts.

DETAILED DESCRIPTION OF THE DRAWINGS

Figure 1:
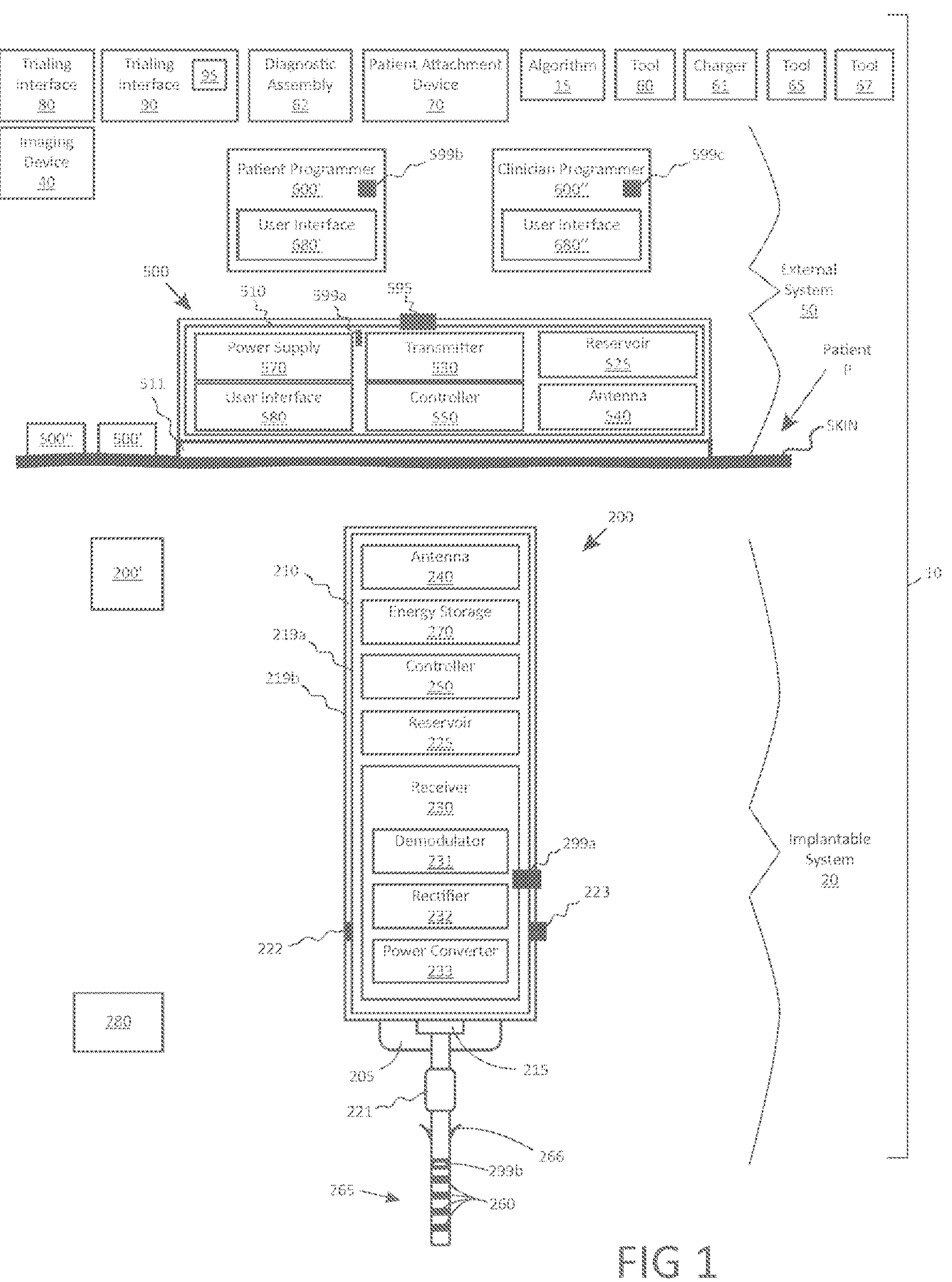
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer, or section. Thus, a first limitation, element, component, region, layer, or section discussed below could be termed a second limitation, element, component, region, layer, or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.). A first component (e.g., a device, assembly, housing, or other component) can be "attached", "connected" or "coupled" to another component via a connecting filament (as defined below). In some embodiments, an assembly comprising multiple components connected by one or more connecting filaments is created during a manufacturing process (e.g., pre-connected at the time of an implantation procedure of the apparatus of the present inventive concepts). Alternatively or additionally, a connecting filament can comprise one or more connectors (e.g., a connectorized filament comprising a connector on one or both ends), and a similar assembly can be created by a user (e.g., a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g., within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

As used herein, the term "proximate" shall include locations relatively close to, on, in, and/or within a referenced component or other location.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

The term "functional element" where used herein, is the be taken to include a component comprising one, two or more of: a sensor; a transducer; an electrode; an energy delivery element; an agent delivery element; a magnetic field generating transducer; and combinations of one or more of these. In some embodiments, a functional element comprises a transducer selected from the group consisting of: light delivery element; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, a functional element comprises a needle, a catheter (e.g., a distal portion of a catheter), an iontophoretic element or a porous membrane, such as an agent delivery element configured to deliver one or more agents. In some embodiments, a functional element comprises one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

The term “transducer” where used herein is to be taken to include any component or combination of components that receives energy or any input and produces an output. For example, a transducer can include an electrode that receives electrical energy and distributes the electrical energy to tissue (e.g., based on the size of the electrode). In some configurations, a transducer converts an electrical signal into any output, such as light (e.g., a transducer comprising a light emitting diode or light bulb), sound (e.g., a transducer comprising a piezo crystal configured to deliver ultrasound energy), pressure, heat energy, cryogenic energy, chemical energy, mechanical energy (e.g., a transducer comprising a motor or a solenoid), magnetic energy, and/or a different electrical signal (e.g., a Bluetooth or other wireless communication element). Alternatively or additionally, a transducer can convert a physical quantity (e.g., variations in a physical quantity) into an electrical signal. A transducer can include any component that delivers energy and/or an agent to tissue, such as a transducer configured to deliver one or more of: electrical energy to tissue (e.g., a transducer comprising one or more electrodes); light energy to tissue (e.g., a transducer comprising a laser, light emitting diode and/or optical component such as a lens or prism); mechanical energy to tissue (e.g., a transducer comprising a tissue manipulating element); sound energy to tissue (e.g., a transducer comprising a piezo crystal); thermal energy to tissue (e.g., heat energy and/or cryogenic energy); chemical energy; electromagnetic energy; magnetic energy; and combinations of one or more of these.

The term “transmission signal” where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term “data signal” where used herein is to be taken to include a transmission signal including at least data. For example, a data signal can comprise a transmission signal including data and sent between a component external to the patient and one or more components implanted in the patient. Alternatively, a data signal can comprise a transmission signal including data sent from an implanted component to one or more components external to the patient. A data signal can comprise a radiofrequency signal including data (e.g., a radiofrequency signal including both power and data) and/or a data signal sent using body conduction.

The term “implantable” where used herein is to be taken to define a component which is constructed and arranged to be fully or partially implanted in a patient’s body and/or a component that has been fully or partially implanted in a patient. The term “external” where used herein is to be taken to define a component which is constructed and arranged to be positioned outside of the patient’s body.

The terms “attachment”, “attached”, “attaching”, “connection”, “connected”, “connecting” and the like, where used herein, are to be taken to include any type of connection between two or more components. The connection can include an “operable connection” or “operable attachment” which allows multiple connected components to operate together such as to transfer information, power, and/or material (e.g., an agent to be delivered) between the components. An operable connection can include a physical connection, such as a physical connection including a connection between two or more: wires or other conductors (e.g., an “electrical connection”), optical fibers, wave guides, tubes such as fluid transport tubes, and/or linkages such as translatable rods or other mechanical linkages. Alternatively or additionally, an operable connection can include a non-physical or “wireless” connection, such as a wireless connection in which information and/or power is transmitted between components using electromagnetic energy. A connection can include a connection selected from the group consisting of a wired connection; a wireless connection; an electrical connection; a mechanical connection; an optical connection; a sound propagating connection; a fluid connection; and combinations of one or more of these.

The term “connecting filament” where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term “connectorized” where used herein is to be taken to refer to a filament, housing or other component that includes one or more connectors (e.g., clinician or other user-attachable connectors) for operably connecting that component to a mating connector (e.g., of the same or different component).

The terms “stimulation parameter”, “stimulation setting”, “stimulation signal parameter”, “stimulation signal setting”, “stimulation waveform parameter”, or “stimulation waveform setting" where used herein can be taken to refer to one or more parameters of a stimulation waveform (also referred to as a stimulation signal). A "stimulation paradigm SP" can represent one or more sets of stimulation parameters to be used in delivering stimulation energy. Applicable stimulation parameters of the present inventive concepts shall include but are not limited to: amplitude (e.g., amplitude of voltage and/or current); average amplitude; peak amplitude; frequency; average frequency; pulse width (also referred to as "pulse pattern on time"); period; phase; polarity; pulse shape; a duty cycle parameter (e.g., frequency, pulse width, and/or off time); inter-pulse gap (also referred to as "pulse pattern off time", or "inter-pulse interval"); polarity; burst-on (also referred to as "dosage on") period; burst-off (also referred to as "dosage off") period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g., the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an "inter-phase gap" can be present within a single pulse. The term inter-phase gap where used herein can refer to a period of time between two portions of a pulse comprising a phase change during which zero energy or minimal energy is delivered. The term "quiescent period" where used herein can refer to a period of time during which zero energy or minimal energy is delivered (e.g., insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. Each implantable device comprises a housing surrounding one or more stimulation producing components. A lead comprising one or more stimulation elements can be pre-attached to the housing, or attachable to the housing (e.g., attached in a clinical procedure in which the implantable device is implanted in a patient).

The apparatus can include a trialing interface which provides energy to the stimulation elements during the implantation procedure (e.g. during a "trialing session" performed during the implantation procedure), such as to confirm proper placement of the stimulation elements and/or to titrate the stimulation delivered. In embodiments in which the lead is pre-attached to the housing of the implantable device, the trialing interface can be configured to provide power (e.g., wireless power) to the implantable device, the implantable device providing stimulation energy to the stimulation elements derived from the power provided by the trialing interface. In embodiments in which the lead is attachable to the housing of the implantable device, the trialing interface can attach to the lead (prior to its attachment to the housing of the implantable device), and the trialing interface can then provide the stimulation energy directly to the stimulation elements.

In some embodiments, the implantable system comprises a first implantable device that delivers stimulation energy via energy received wirelessly from one or more external devices, and a second implantable device that delivers stimulation energy via an integral (e.g., implanted) battery. In these embodiments, the first implantable device can be configured to deliver stimulation energy during a limited period of time (e.g., a trial period in which stimulation parameter settings are determined and/or acceptability of the apparatus is determined), and the second implantable device can be configured to deliver stimulation energy for a prolonged period of time in which long-term stimulation therapy is provided to a patient. In these embodiments, a single implantable lead comprising one or more stimulation energy delivery elements (e.g., electrodes) can be connected to the first implantable device and then the second implantable device. In some embodiments, a first implantable device can be configured to remain implanted in the patient for a limited period of time, such as to reduce cost of manufacture, and a second implantable device is configured for a longer implant life. The first implantable device can be used in a trialing procedure (also referred to as a "trialing session" herein) in which the stimulation apparatus is assessed for acceptable use (e.g., by the patient and/or clinician) and/or one or more stimulation parameter settings are optimized or otherwise determined.

Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements (e.g., an implantable stimulation element). An implantable functional element can be configured to interface with the patient (e.g., interface with tissue of the patient or interface with any patient location). Alternatively or additionally, an implantable functional element can interface with a portion of an implantable device (e.g., to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g., patient physiologic or patient environment information).

Each implantable device can comprise an implantable controller configured to control (e.g., modulate power to, send a signal to, and/or receive a signal from) the one or more implantable functional elements. In some embodiments, an implantable controller of a first implantable device is configured to control one or more other implantable devices. Each implantable device can comprise an implantable energy storage assembly (e.g., a battery and/or a capacitor) configured to provide power to the implantable controller (e.g., a controller comprising a stimulation waveform generator), the implantable receiver and/or the one or more implantable functional elements. In some embodiments, an implantable energy storage assembly is further configured to provide power to an assembly that transmits signals via the implantable antenna (e.g., when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be positioned outside the implantable housing, and tethered (e.g., electrically tethered) to one or more electrical components of the implantable device positioned within the implantable housing. In some embodiments, one or more implantable functional elements are positioned on an implantable lead, such as a flexible lead mechanically fixed or attachable to the implantable housing and operably connected (e.g., electrically, fluidly, optically and/or mechanically) to one or more components internal to the implantable housing. The implantable lead can be inserted (e.g., tunneled) through tissue of the patient, such that its one or more functional elements are positioned proximate tissue to be treated and/or positioned at an area in which data is to be recorded. In some embodiments, the implantable lead is configured to operably attach to and/or detach from, multiple implantable devices.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g., when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set, adjust, and/or otherwise modify one or more treatment and/or data recording settings of the medical apparatus of the present inventive concepts. In some embodiments, the external programmer is configured to collect and/or diagnose recorded patient information, such as to provide the information and/or diagnosis to a clinician of the patient, to a patient family member and/or to the patient themselves. The collected information and/or diagnosis can be used to modify treatment or other operating parameters of the medical apparatus. In some embodiments, at least two external programmers are included, such as a first external programmer configured for use by the patient, and a second external programmer configured for use by a clinician of the patient.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy" herein) delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a medical apparatus for providing a therapy to a patient is illustrated, consistent with the present inventive concepts. Apparatus 10 comprises implantable system 20 and external system 50. External system 50 transmits transmission signals to one or more components of implantable system 20. These transmission signals can comprise power and/or data. Implantable system 20 comprises implantable device 200 shown implanted beneath the skin of patient P.

In some embodiments, implantable system 20 comprises multiple similar or dissimilar implantable devices 200 (singly or collectively implantable device 200), such as is described in applicant's co-pending U.S. patent application Ser. No. 17/372,095, titled "Apparatus with Enhanced Stimulation Waveforms", filed Jul. 9, 2021. Each implantable device 200 can be configured to receive power and data from a transmission signal transmitted by external system 50, such as when stimulation energy delivered to the patient (e.g., to nerve or other tissue of the patient) by implantable device 200 is provided via wireless transmissions signals from external system 50. In some embodiments, implantable system 20 comprises at least two implantable devices, such as implantable device 200 and implantable device 200' shown in FIG. 1. Implantable device 200' can be of similar construction and arrangement to implantable device 200, and it can include components of a different configuration. Each implantable device 200 comprises one or more housings, housing 210 shown, which surrounds various other components of device 200. Each implantable device 200 comprises one or more stimulation and/or other functional elements, such as stimulation element 260 shown, where stimulation elements 260 are configured to deliver stimulation energy, a stimulating drug or other agent, and/or another form of stimulation (e.g., another form of tissue stimulation) to the patient. In some embodiments, one or more stimulation elements 260 are further configured as a sensor (e.g., when comprising an electrode configured to both deliver electrical energy and record electrical signals). Each implantable device 200 can include one or more leads, lead 265 shown, and each lead 265 can include one or more stimulation elements 260. Alternatively or additionally, one or more stimulation elements 260 can be positioned on housing 210 or one or more other components of implantable device 200. Each lead can include one or more elements configured to anchor lead 265 to tissue, such as anchor element 221 shown. Anchor element 221 can be configured to slidingly receive the shaft of lead 265 (e.g., to position anchor element 221 about lead 265 in manufacturing and/or in an implantation procedure). Anchor element 221 can include one or more fixation points, such as one or more circumferential recesses. Surgical clips or sutures can be placed around a recess and into tissue, such as to fixate anchor element 221 and an inserted lead 265 to tissue.

Each implantable device 200 can comprise one or more other types of functional elements, such as functional element **299*a* shown positioned proximate housing 210 (e.g., within and/or on the external surface of housing 210) and/or functional element 299*b* shown positioned on lead 265. Functional element 299*a* and/or 299*b* (singly or collectively functional element 299) can comprise a transducer, a sensor, and/or other functional element as described herein. In some embodiments, a functional element 299** comprises a visualizable marker, such as a radiopaque marker, an ultrasonically visible marker, and/or a magnetic marker.

External system 50 can comprise an external device 500, which includes one or more housings, housing 510 shown, which surrounds various other components of device 500. In some embodiments, external system 50 comprises multiple external devices 500 (singly or collectively external device 500), such as an external device as is described in applicant's co-pending U.S. patent application Ser. No. 17/372,095, titled "Apparatus with Enhanced Stimulation Waveforms", filed Jul. 9, 2021. In some embodiments, external system 50 comprises at least two, or at least three external devices (e.g., at least two external devices configured to deliver power and/or data to one or more implantable devices 200), such as external device 500, external device 500', and external device 500" shown in FIG. 1. External device 500' and/or 500" can be of similar construction and arrangement to external device 500, and these devices can include components of a different configuration.

External system 50 can comprise one or more programming devices, programmer 600, such as patient programmer 600' and clinician programmer 600" shown. Patient programmer 600' and clinician programmer 600" (singly or collectively programmer 600) each comprise a user interface, such as user interfaces 680' and 680" shown (singly or collectively user interface 680). Programmer 600 can be configured to control one or more external devices 500. Alternatively or additionally, programmer 600 can be configured to control one or more implantable devices 200 (e.g., when no external device 500 is included in apparatus 10 or at least no external device 500 is available to communicate with an implantable device 200). Patient programmer 600' can be configured to be used by the patient, patient caregiver (e.g., clinician of the patient), and/or a family member of the patient.

Clinician programmer 600" can be of similar construction and arrangement to patient programmer 600'. In some embodiments, clinician programmer 600" provides additional functions not available using patient programmer 600'. In some embodiments, clinician programmer 600" can modify the programming of patient programmer 600' (e.g., modify the programming options available to the patient or family member of the patient).

Patient programmer 600' can be further configured as a smart phone and/or a music playing device (e.g., an mp3 player). For example, patient programmer 600' can comprise a smart phone or other commercial device onto which a software program of apparatus 10 is embedded to cause the commercial device to function as patient programmer 600'. Clinician programmer 600" can comprise a tablet-like device. For example, clinician programmer 600" can comprise a commercial tablet device onto which a software program of apparatus 10 is embedded to cause the commercial tablet to function as clinician programmer 600".

Clinician programmer 600" can configure multiple (e.g., all) external devices 500 used by a patient, as well as patient programmer 600', so that the set of devices are configured as a "trusted" network. After this configuration, patient programmer 600' can safely and effectively communicate with the one or more external devices 500 of the patient. The patient programmer 600' can upload (e.g., automatically upload) configuration information from an external device 500 (e.g., stimulation parameter settings and the like). In some embodiments, patient programmer 600' and/or clinician programmer 600" uploads configuration information from an external device 500 any time certain information (e.g., stimulation information) on that external device 500 has changed (e.g., a change is detected by the programmer 600 or otherwise).

External system 50 can comprise one, two, three, or more functional elements, such as functional elements 599*a*, 599*b*, and/or 599*c* (singly or collectively functional element 599), shown positioned in external device 500, patient programmer 600', and clinician programmer 600", respectively.

Apparatus 10 can be configured to stimulate tissue (e.g., stimulate nerve tissue such as tissue of the central nervous system or tissue of the peripheral nervous system, such as to neuromodulate nerve tissue), such as by having one or more implantable devices 200 deliver and/or otherwise provide energy (hereinafter "deliver energy") and/or deliver an agent (e.g., a pharmaceutical compound or other agent) to one or more tissue locations, such as via one or more stimulation elements 260. In some embodiments, one or more implantable devices 200 deliver energy and/or an agent while receiving power and/or data from one or more external devices 500. In some embodiments, one or more implantable devices 200 deliver energy and/or an agent (e.g., continuously or intermittently) using energy provided by an internal power source (e.g., a battery and/or capacitor) without receiving externally supplied power, such as for periods of at least 1 hour, at least 1 day, at least 1 month or at least 1 year. In some embodiments, one or more stimulation parameters are varied (e.g., systematically and/or randomly), during that period.

In some embodiments, apparatus 10 is further configured as a patient diagnostic apparatus, such as by having one or more implantable devices 200 record a patient parameter (e.g., a patient physiologic parameter) from one or more tissue locations, such as while receiving power and/or data from one or more external devices 500. In some embodiments, during its use, one or more implantable devices 200 at least receives power from one or more external devices 500 (e.g., with or without also receiving data). Alternatively or additionally, one or more patient parameters can be recorded by an external device of apparatus 10, such as via a programmer 600 and/or an external device 500.

Apparatus 10 can be configured as a patient information recording apparatus, such as by having one or more implantable devices 200 and/or one or more external devices 500 record patient information (e.g., patient physiologic information and/or patient environment information). In some embodiments, one or more implantable devices 200 and/or one or more external devices 500 further collect information (e.g., status information or configuration settings) of one or more of the components of apparatus 10.

In some embodiments, apparatus 10 is configured to deliver stimulation energy to tissue to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, dorsal root, dorsal root ganglia, spinal nerves, ganglia, and/or other nerve tissue. The delivered energy can comprise energy selected from the group consisting of: electrical energy; magnetic energy; electromagnetic energy; light energy such as infrared light energy, visible light energy and/or ultraviolet light energy; mechanical energy; thermal energy such as heat energy and/or cryogenic energy; sound energy such as ultrasonic sound energy (e.g., high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g., constant or otherwise controlled) electrical current and/or voltage to tissue; magnetic energy (e.g., magnetic field energy) such as by applying controlled current or voltage to a coil or other magnetic field generating element positioned proximate tissue; and/or electromagnetic energy such as by providing both current to tissue and a magnetic field to tissue. A coil or other magnetic field generating element can surround (e.g., at least partially surround) the target nerve. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to one or more implantable devices 200, and the one or more implantable devices 200 deliver stimulation energy to tissue with a stimulation signal (also referred to as a stimulation waveform), with the power signal and the stimulation signal having one or more different characteristics (e.g., as described herebelow). The power signal can be modulated with data (e.g., configuration or other data to be sent to one or more implantable devices 200). In these embodiments, the characteristics of the stimulation signal delivered (e.g., amplitude, frequency, duty cycle and/or pulse width) can be independent (e.g., partially or completely independent) of the characteristics of the power signal transmission (e.g., amplitude, frequency, phase, envelope, duty cycle and/or modulation). For example, the frequency and modulation of the power signal can change without affecting those or other parameters of the stimulation signal, and/or the parameters of the stimulation signal can be changed (e.g., via programmer 600), without requiring similar or any changes to the power signal. In some embodiments, implantable system 20 is configured to rectify the received power signal, and to produce a stimulation waveform with entirely different characteristics (e.g., amplitude, frequency and/or duty cycle) from the rectified power signal. Each implantable device 200 can comprise an oscillator and/or controller configured to produce the stimulation signal. In some embodiments, one or more implantable devices 200 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g., data and power) to implantable system 20, and implantable system 20 recovers (e.g., decodes, demodulates, or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL); phase locked loop (PLL); high frequency clock; and/or crystal oscillator needed to perform the synchronization. Avoiding these components can also be correlated to reduced package size of each implantable device 200 (e.g., avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013.

Apparatus 10 can be configured to treat pain, such as back pain and/or limb pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these.

In some embodiments, apparatus 10 is configured to treat a patient disease or disorder selected from the group consisting of chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; hypertension; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

In some embodiments, apparatus 10 is configured to treat one or more diseases or disorders by delivering stimulation to perform renal modulation. In some embodiments, apparatus 10 is configured to treat hypertension, such as when apparatus 10 is configured to deliver stimulation to perform renal neuromodulation.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more stimulation elements 260 of one or more implantable devices 200 can be implanted at one or more spinal cord locations, such as to deliver stimulation to tissue proximate those locations. In some embodiments, stimulation elements 260 comprise two or more stimulation elements (e.g., electrodes) that span multiple vertebrae of the spinal column (e.g., multiple stimulation elements that span at least T8 to T9 and/or T9 to T10). Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more stimulation elements 260 are configured to deliver energy (e.g., electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g., one or more stimulation elements 260, functional elements 299, functional elements 599 and/or other functional elements of implantable system 20) are configured (e.g., further configured) to record a patient parameter (e.g., stimulation element 260, functional element 299, functional element 599, and/or another functional element of apparatus 10 are configured as a sensor), such as a patient heart or spine parameter, and the information recorded is used to modify the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more stimulation elements 260 can be positioned proximate cardiac tissue and deliver a stimulation signal as described herein (e.g., based on power and/or data received by implantable system 20 from external system 50). The stimulation signal can be used to pace, defibrillate and/or otherwise stimulate the heart. Alternatively or additionally, apparatus 10 can be configured to record cardiac activity (e.g., by recording EKG, blood oxygen, blood pressure, heart rate, ejection fraction, wedge pressure, cardiac output, lung impedance and/or other properties or functions of the cardiovascular system via a sensor-based element 260, and/or other sensor of apparatus 10), such as to determine an onset of cardiac activity dysfunction or other undesired cardiac state. In some embodiments, apparatus 10 is configured to both record cardiac or other information and deliver a stimulation signal to cardiac tissue (e.g., stimulation varied or otherwise based on the recorded information). For example, apparatus 10 can be configured such that external system 50 transmits power and/or data to implantable system 20, where implantable system 20 monitors cardiac activity, and upon detection of an undesired cardiovascular state, implantable system 20 delivers a pacing and/or defibrillation signal to the tissue that is adjacent to one or more stimulation elements 260 configured to deliver a cardiac stimulation signal.

Apparatus 10 can be configured to perform a diagnostic procedure including measuring one or more patient parameters (e.g., patient physiologic or other patient parameters), such as are described in detail herebelow. In some embodiments, apparatus 10 is configured to measure a physiologic parameter that can be sensed from one or more sensor-based stimulation elements 260, functional elements 299, and/or functional elements 599 positioned in subcutaneous tissue. In these embodiments, external system 50 can comprise an external device 500 configured for placement proximate an implantable device 200 implanted in a position to record data from subcutaneous tissue (e.g., blood glucose data). External device 500 can comprise a wrist band, a wristwatch, and/or an arm band configuration such as when the implantable device 200 is positioned in subcutaneous tissue proximate the patient's wrist or upper arm. The external device 500 can comprise a leg, knee, or ankle band configuration, such as when one or more implantable devices 200 are positioned in subcutaneous tissue proximate the patient's ankle, knee, and/or thigh. In some embodiments, external device 500 comprises a band or other attachment device for positioning about the thorax, neck, groin, and/or head of the patient. Power and/or data can be sent to the implantable device 200 from the external device 500, and data (e.g., blood glucose data) can be sent to external device 500 (or another component of external system 50) by implantable device 200, such as using a wireless communication configuration known to those of skill in the art. In some embodiments, external system 50 comprises a functional element 599 (e.g., functional element 599*a*, 599*b*, and/or 599*c*) configured to deliver an agent (e.g., insulin or glucose delivered by a needle-based functional element 599), based on the information received from implantable device 200. Alternatively, or additionally, implantable device 200 comprises a stimulation element 260 configured to deliver an agent (e.g., insulin or glucose delivered by a needle-based stimulation element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

As described hereabove, external system 50 can be configured to transmit power and/or data (e.g., implantable system 20 configuration data) to one or more implantable devices 200 of implantable system 20. Implantable system 20 configuration data provided by external system 50 (e.g., via one or more antennas, antenna 540 shown, of one or more external devices 500) can include when to initiate stimulation delivery (e.g., energy delivery), and/or when to stop stimulation delivery, and/or it can include data related to the value or change to a value of one or more stimulation parameters as described hereabove. The configuration data can include a stimulation parameter such as an agent (e.g., a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

As described hereabove, external system 50 can comprise one or more external devices 500. External system 50 can comprise one or more antennas 540, such as when a single external device 500 comprises one or more antennas 540, and/or when multiple external devices 500 each comprise one or more antennas 540. The one or more antennas 540 can transmit power and/or data to one or more antennas 240 of implantable system 20, such as when a single implantable device 200 comprises one or more antennas 240, and/or when multiple implantable devices 200 each comprise one or more antennas 240. In some embodiments, one or more antennas 540 define a radiation footprint (e.g., a footprint defining a volume, such as a volume of tissue, in which electromagnetic transmissions radiated by antennas 540 can be properly received by antennas 240), such as is described in applicant's co-pending U.S. patent application Ser. No. 17/412,044, titled "Medical Apparatus Including an Implantable System and an External System", filed Aug. 25, 2021.

External system 50 transmits power and/or data with a transmission signal comprising at least one wavelength, k. External system 50 and/or implantable system 20 can be configured such that the distance between an external antenna 540 transmitting the power and/or data and one or more implantable antennas 240 receiving the power and/or data transmission signal is equal to between 0.1λ and 10.0λ, such as between 0.2λ and 2.0λ. In some embodiments, one or more transmission signals are delivered by a transmitter, transmitter 530, at a frequency range between 10 MHz and 10.6 GHz, such as between 0.1 GHz and 10.6 GHz, between 10 MHz and 3.0 GHz, between 40 MHz and 1.5 GHz, between 10 MHz and 100 MHz, between 0.902 GHz and 0.928 GHz, in a frequency range proximate to 40.68 MHz, in a frequency range proximate to 866 MHz, or approximately between 863 MHz and 870 MHz. Transmitter 530 can comprise a transmitter that produces a transmission signal with a power level between 0.01 W and 4.0 W, such as a transmission signal with a power level between 0.01 W and 2.0 W or between 0.2 W and 1.0 W.

In addition to transmitting power and/or data to implantable system 20, external system 50 can be further configured to provide information (e.g., patient information and/or apparatus 10 performance information) to one or more other components of apparatus 10, such as tool 60 shown in FIG. 1 and described in detail herebelow.

One or more external devices 500 (singly or collectively external device 500) can be configured to transmit power and/or data (e.g., implantable system 20 configuration data) to one or more implantable devices 200 (singly or collectively implantable device 200). In some embodiments, one or more external devices 500 are configured to transmit both power and data (e.g., simultaneously and/or sequentially) to one or more implantable devices 200. In some embodiments, one or more external devices 500 are further configured to receive data from one or more implantable devices 200 (e.g., via data transmitted by one or more antennas 240 of one or more implantable devices 200). Each external device 500 can comprise housing 510, power supply 570, a transmitter 530, a controller 550, and/or one or more antennas 540, each shown in FIG. 1 and described in detail herebelow. Each external device 500 can further comprise one or more functional elements 599*a*, such as a functional element comprising a sensor, electrode, energy delivery element, a magnetic-field-generating transducer, and/or any transducer, also described in detail herebelow. In some embodiments, a functional element 599*a* comprises one or more sensors configured to monitor performance of external device 500 (e.g., to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530, controller 550, and/or power supply 570 shown in FIG. 1. In some embodiments, a single external device 500 comprises multiple discrete (i.e. separate) housings 510, two or more of which can each transfer data and/or other signals via a wired or wireless connection to the other, to an implantable device 200, and/or to another component of apparatus 10. In some embodiments, a housing 510 further surrounds a programmer 600 (e.g., programmer 600' or 600") and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g., shielded to prevent transmission of electromagnetic waves), and an unshielded portion, such as an unshielded portion surrounding antenna 540.

Housing 510 can comprise an adhesive element (e.g., a spacer 511, as described herein, configured as an adhesive element), such as an adhesive element configured to temporarily attach an external device 500 to the patient's skin. Alternatively or additionally, housing 510 can be constructed and arranged to engage (e.g., fit in the pocket of) a patient attachment device, such as patient attachment device 70 described herebelow.

One or more antennas 540 (singly or collectively antenna 540) can each comprise one, two, three, or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. For antenna 540 to operate effectively at higher frequencies, the shield material can comprise a ferrite material that has a low conductivity and low magnetic loss tangent at a frequency of interest, and whereby a higher permeability is achieved. By placing a material with a high magnetic permeability ($\mu'$), low magnetic loss tangent ($\mu''/\mu'$), and low conductivity at the operating frequency (such as a high frequency ferrite) between the antenna and other elements of the transmitter, the losses or loading effects due to these elements can be dramatically reduced. In some cases, the magnetic field magnification of this shielding layer will enhance the overall performance. Additionally, this layer shields the outside environment from unwanted radiation from the antenna, and it protects the antenna from radiation originating in the environment.

In some embodiments, a spacing layer is positioned between antenna 540 and the shield material. The spacing layer can comprise a thickness of between 0 mm and 5 mm, such as between 0.25 mm and 1 mm. The spacing layer can comprise non-conductive dielectric materials, air, or other materials that have minimal impact on antenna performance. The spacing layer can also be incorporated into a board thickness, with the antenna being constructed on the opposite side of the board in relation to the shielding layer. The shielding layer can comprise a ferrite material as described hereabove, or any material with the desired permeability, magnetic loss, and conductivity at the frequency of interest. The thickness of the shielding layer can be dependent on its specific material properties and the application. In some embodiments, a conductive layer on the side of the shielding layer is positioned opposite the antenna to further shield unwanted radiation. To reduce weight, the shielding layer material can be porous or incorporate holes or slots spaced in a way to minimize the reduction in performance. The holes and spacings can be sized smaller than a wavelength of the RF signal. If no spacing layer is used, the shielding layer can extend inside the antenna. Additionally or alternatively, the shielding layer can be positioned on the other side or both sides of the antenna because of the field magnification effect. In some embodiments, the shielding layer is constructed to increase the directivity of the antenna or focus the electromagnetic energy.

One or more antennas 540 can be positioned in a housing 510 that is otherwise void of other components (e.g., void of power supply 570, controller 550 and/or transmitter 530), such as when an antenna 540 is positioned within a first housing 510 and communicates with components positioned in a second housing 510.

In some embodiments, one or more spacers, spacer 511 shown, is positioned between antenna 540 and the patient's skin, such as a spacer comprising a thickened portion of housing 510 or a discrete spacer 511 placed on a side of housing 510 (as shown) or on a side of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g., a spacer 511 comprising thermally insulating material). Alternatively, or additionally, housing 510 can comprise a heat insulating and/or dissipating material. Spacer 511 can comprise a soft or otherwise compressible material (e.g., foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g., tilt) with respect to the tissue surface.

In some embodiments, antenna 540 comprises a multi-feed point antenna, such as a multi-feed point antenna configured to: support beam shaping and/or focusing; allow modification of amplitude and/or phase of a transmission signal; increase the radiation footprint; and combinations of one or more of these.

In some embodiments, antenna 540 comprises one or more antennas selected from the group consisting of: patch antenna; slot antenna; array of antennas; a loop antenna (e.g., a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm, and/or a major axis of approximately 4 cm. Antenna 540 can be further configured to receive a signal, such as when an antenna 240 is configured to transmit data to an external device 500. Antenna 540 can be positioned on (e.g., fabricated onto) a substrate, such as a flexible printed circuit board or other printed circuit board (e.g., a single or multiple layer printed circuit board comprising electrical traces connecting components).

A single external antenna 540 can be configured to transmit power and/or data to multiple implantable devices 200 (e.g., each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g., within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 is optimized for a different design parameter than the second antenna 540, and each antenna 540 can be activated independently or simultaneously to realize both benefits. In some embodiments, the first antenna 540 is similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 transmit power and/or data to one or more antennas 240, the transmissions performed simultaneously or sequentially. In sequential power and/or data transfers, a first external device 500 comprising a first one or more antennas 540 can be replaced (e.g., swapped) with a second external device 500 comprising a second one or more antennas 540. Alternatively or additionally, sequential power and/or data transfer can be initiated by one or more of the following conditions: when a first external antenna 540 moves (e.g., moves relative to an implanted antenna 240); when a second external device 500 comprising a second antenna 540 is turned on or otherwise activated; when a second antenna 540 provides improved power and/or data transfer to antenna 240 than that which is provided by a first antenna 540; and/or when power received from a first antenna 540 decreases (e.g., decreases below a threshold). In some embodiments, an antenna 240 receives power from a first antenna 540 and a second antenna 540, but only receives data from the first antenna 540. In some embodiments, a first antenna (e.g., an antenna 240 or an antenna 540) is driven with a different carrier signal than a second antenna (e.g., an antenna 240 or an antenna 540). The two carrier signals can comprise differences in amplitudes and/or relative phases as compared to each other. Each carrier signal can include a data transmission signal (e.g., data to be transmitted to an implantable device 200 from an external device 500 or to an external device 500 from an implantable device 200).

External device 500 can comprise an electronics module, controller 550 shown, which can be configured to control one or more other components of external device 500. Controller 550 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, controller 550 comprises a memory storage component that includes instructions, such as instructions used by controller 550 to produce a stimulation waveform and/or perform an algorithm, each as described herein.

One or more transmitters 530 (singly or collectively external transmitter 530) can each comprise one or more external transmitters that drive one or more antennas 540 (e.g., one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. Transmitter 530 can be configured to perform multi-level amplitude shift keying. The amplitude shift-keying can be configured to provide adjustable-depth modulation between 0-100% depth, such as between 5-75% depth, or such as between 10-50% depth.

As described herein, one or more external devices 500 can be configured to transmit data (e.g., configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to modify the level of power transmitted to one or more implantable devices 200, such as by modifying one or more duty cycling parameters. In these embodiments, power transmitted can be modified to: set a power transfer based on a stimulation level produced by implantable system 20; prevent oversaturation; to reduce interference with implantable system 20 data transmissions (e.g., when one or more implantable devices 200 are further configured to transmit data to external system 50); set a power transfer based on charge information and/or discharge information related to an implantable device 200 (e.g., charge rate and/or discharge rate of implantable energy storage assembly 270 described herebelow); and combinations of one or more of these. In some embodiments, implantable system 20 comprises a first receiver 230 (e.g., of a first implantable device 200) and a second receiver 230 (e.g., of a second implantable device 200'). One or more transmitters 530 can be configured to transmit a first power transmission to the first receiver 230, and a second power transmission to the second receiver 230. The first power transmission and the second power transmission can be modified or otherwise be different, such as to prevent oversaturation.

In some embodiments, transmitter 530 (and/or another component of external system 50) is further configured as a receiver (e.g., can further include a receiver, in addition to a transmitter or include a transmitter that further functions as a receiver), such as to receive data from implantable system 20. For example, a transmitter 530 can be configured to receive data via one or more antennas 240 of one or more implantable devices 200. Data received can include patient information (e.g., patient physiologic information, patient environment information or other patient information) and/or information related to an implantable system 20 parameter (e.g., an implantable device 200 stimulation parameter and/or another configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as a programmer 600; cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 599 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g., via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g., serially replaced) by the second battery (e.g., external device 500 can function with a single battery). In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source. Power supply 570 can include voltage and/or current control circuitry. Alternatively or additionally, power supply 570 can include charging circuitry, such as circuitry configured to interface a rechargeable battery with an external charging device. In some embodiments, apparatus 10 includes one or more charging devices, charger 61 shown, which can be configured to recharge a component of apparatus 10, such as to recharge power supply 570 of one or more external devices 500. In some embodiments, charger 61 comprises one or more electrical contacts configured to electrically connect to one or more electrical contacts of external device 500, such as to transfer charging energy to power supply 570. Charger 61 can be configured to perform various data transfers with one or more external devices 500, and/or perform other functions, such as are described herein in reference to FIGS. 13, 13A, and 13B.

Each external device 500 can include one or more user interface components, user interface 580 shown, such as to allow the patient or other user to enter, adjust and/or otherwise modify ("enter", "adjust", and/or "modify" herein) one or more parameters of apparatus 10 (e.g., one or more variable stimulation parameters of apparatus 10). User interface 580 can include one or more user input components (e.g., buttons, slides, knobs, and the like) and/or one or more user output components (e.g., lights, displays and the like). In some embodiments, user interface 580 includes one or more controls configured to provide a water-ingress-resistant barrier.

Each patient programmer 600' or clinician programmer 600" (singly or collectively programmer 600) comprises a programming device configured to control one or more components of apparatus 10. Programmer 600 can comprise a user interface 680. Programmer 600 can send and/or receive commands to and/or from one or more external devices 500 via a wireless or wired connection (wired connection not shown but such as one or more insulated conductive wires). In some embodiments, one or more external devices 500 comprise all or a portion of programmer 600, such as when all or a portion of user interface 680 is integrated into housing 510 of external device 500. In some embodiments, apparatus 10 comprises multiple programmers 600, such as one or more patient programmers 600' and/or one or more clinician programmers 600".

Programmer 600 can be configured to modify one or more parameters of apparatus 10, such as a stimulation parameter (e.g., a stimulation waveform parameter as described herein); a sensing parameter; a therapy parameter; a data recording parameter (e.g., a patient data recording parameter and/or an implantable device 200 data recording parameter); power transfer; data rate; activity of one or more external transmitters 530; activity of one or more external antennas 540; a stimulation element 260 parameter; a functional element 299 and/or 599 parameter; and combinations of one or more of these, such as is described hereabove. Programmer 600 can be further configured to provide information, such as patient physiologic information recorded by apparatus 10 (e.g., by one or more implantable devices 200 and/or one or more external devices 500), or apparatus 10 information, such as performance and/or configuration information (singly or collectively "status information") of one or more components of apparatus 10 (e.g., one or more external devices 500 and/or implantable devices 200). In some embodiments, programmer 600 uses information recorded by one or more implantable devices 200, apparatus 10 information, and/or information from external devices 500 to adapt configuration parameters of one or more components of apparatus 10.

In some embodiments, programmer 600 is configured to confirm that an adequate power transmission and/or an adequate data transmission has occurred between one or more external devices 500 and one or more implantable devices 200. In these embodiments, programmer 600 can comprise diagnostic assembly 62 described herebelow, or otherwise be configured to detect one or more of: power transmission to the implantable system 20 (e.g., to detect power transmission to implantable system 20 below a threshold); power transmission to the implantable system 20 trending in an undesired direction; improper and/or inadequate data transfer to the implantable system 20; and combinations of one or more of these. In some embodiments, programmer 600 monitors power transfer in real time and modifies power transmission accordingly to optimize the rectifier efficiency (e.g., efficiency of rectifier 232 described herebelow) of one or more implantable devices 200. In some embodiments, apparatus 10 can be configured to modify (e.g., in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These modifications can include modification of one or more of: power transmission amplitude, duty cycle, frequency, phase, and periodicity.

In some embodiments, programmer 600 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 600 can be configured to monitor a standing wave pattern at the output of the transmitter 530.

In some embodiments, programmer 600 comprises a lookup table of stimulation signal waveform patterns, such as to allow a clinician, patient and/or other operator ("user" or "operator" herein) of apparatus 10 to view and/or select a predetermined stimulation pattern (e.g., using user interface 680). In some embodiments, programmer 600 comprises a set of adjustable stimulation signal parameters configured to be varied to allow an operator to construct customized waveforms, such as to vary one or more stimulation parameters described hereabove. In some embodiments, programmer 600 is configured to allow an operator to create a customized waveform by specifying an amplitude of one or more discrete pulses or steps of a stimulation signal. In some embodiments, a clinician programmer 600" can include stimulation waveform customization options not provided by a patient programmer 600'.

In some embodiments, programmer 600 comprises a transmitter configured to transmit data to tool 60 or another device such as a cell phone; computer; tablet; computer network such as the internet or a LAN; and combinations of one or more of these. In these embodiments, programmer 600 can comprise a wireless transmitter; a Bluetooth transmitter; a cellular transmitter; and combinations of one or more of these. In some embodiments, programmer 600 comprises a receiver configured to receive data, or a transceiver configured to both transmit and receive data. In some embodiments, programmer 600 is configured to transmit data to and/or receive data from another component of apparatus 10 (e.g. via a wired or wireless network or other data transfer arrangement), such as is described herein in reference to FIGS. 13, 13A, and 13B.

User interface 680 of programmer 600 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 599, such as functional elements 599*a*, 599*b*, and/or 599*c*, shown positioned in external device 500, programmer 600', and in programmer 600", respectively. Each functional element 599 can comprise a functional element as defined hereabove (e.g., a sensor, a transducer, and/or other functional element as described herein). In some embodiments, a functional element 599 comprises a needle, a catheter (e.g., a distal portion of a catheter), an iontophoretic element or a porous membrane, such as an agent delivery element configured to deliver one or more agents contained (e.g., one or more agents in a reservoir, such as reservoir 525 described herebelow) within an external device 500 and delivered into the patient (e.g., into subcutaneous tissue, into muscle tissue and/or into a blood vessel such as a vein).

In some embodiments, the functional element 599 comprises an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more stimulation elements 260.

In some embodiments, one or more functional elements 599 comprise a sensor, such as a sensor configured to record data related to a patient parameter (e.g., a patient physiologic parameter), an external system 50 parameter and/or an implantable system 20 parameter. In some embodiments, operation of one or more implantable devices 200 (e.g., stimulation energy delivered by one or more implantable devices 200) is configured to be delivered based on the data recorded by one or more sensor-based functional elements 599, such as in a closed-loop energy delivery mode.

Functional element 599 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity (e.g., as measured using electromyography, EMG); electrical activity produced by skeletal muscles (e.g., as measured using EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 599 can comprise one or more sensors configured to record data representing a parameter of external system 50 or any component of apparatus 10. Functional element 599 can comprise one or more sensors selected from the group consisting of: an energy sensor; a voltage sensor; a current sensor; a temperature sensor (e.g., a temperature of one or more components of external device 500 or programmer 600); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g., via controller 250 described herebelow) the data recorded by functional element 599 to assess one or more of: power transfer; link gain; power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 599 are positioned on a housing 510. A functional element 599 can comprise a body conduction sensor, such as a body conduction sensor configured to record and/or receive data via skin conduction. A functional element 599 can be configured to record data associated with stimulation delivered by one or more implantable devices 200 (e.g., record data associated with stimulation energy delivered by one or more stimulation elements 260), such as to provide closed loop or semi-closed loop stimulation. A functional element 599 can be configured to record temperature, such as when apparatus 10 is configured to deactivate or otherwise modify the performance of an external device 500 when the recorded temperature (e.g., patient temperature and/or external device 500 temperature) exceeds a threshold.

In some embodiments, an external device 500, programmer 600', and/or programmer 600" comprises a temperature sensor, such as when functional elements 599*a*, 599*b*, and/or 599*c*, respectively, comprise a temperature sensor. The temperature-based functional element 599 can be positioned proximate a portion of programmer 600, housing 510 and/or one or more antennas 540 (e.g., to measure the temperature of one or more portions of a programmer 600 and/or external device 500). In these embodiments, the temperature data recorded by the functional element 599 is used to modify one or more of: matching network; stimulation level (e.g., stimulation energy delivered by one or more implantable devices 200); power transmission level (e.g., level of power transmitted between one or more external devices 500 and one or more implantable devices 200); and combinations of one or more of these. In some embodiments, the temperature sensor-based functional element 599 is a part of a safety mechanism that deactivates programmer 600 and/or an external device 500 if the recorded temperature exceeds a threshold. Alternatively or additionally, a temperature sensor-based functional element 599 can be configured to measure temperature of the patient, such as when placed on housing 510, such as to modify energy and/or agent delivery performed by implantable device 200 based on the recorded patient temperature.

In some embodiments, an external device 500, programmer 600', and/or programmer 600" comprise an accelerometer, vibration sensor, and/or other motion or shock sensor, such when functional elements 599*a*, 599*b*, and/or 599*c* comprise this type of sensor. In these embodiments, the functional elements 599 can comprise a sensor configured to produce a signal used to detect when an external device 500, programmer 600', and/or programmer 600" is dropped, as well as assess the forces generated during the drop. Alternatively or additionally, this sensor can be configured to produce a signal configured to detect a tap (e.g., on a housing) of the device, such that a tap gesture can be used in place of a control (e.g., a discrete switch) on the device.

As described hereabove, implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200'. Each implantable device 200 can be configured to treat a patient (e.g., treat pain of the patient) and/or record patient information, such as by delivering energy and/or an agent to tissue and/or by recording one or more physiologic parameters of the patient (e.g., parameters of tissue of the patient).

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 (e.g., at least a portion of device 200 such as stimulation elements 260, lead 265, and/or housing 210) can be visualized (e.g., during and/or after implantation) via an imaging device (e.g., imaging device 40 described herein) such as a CT, X-ray, fluoroscope, ultrasound imager and/or MRI.

In some embodiments, implantable system 20 comprises multiple implantable devices 200 (e.g., implantable device 200 and implantable device 200' shown in FIG. 1) and implantable system 20 comprises a "multi-point ready" system, in which the operation (e.g., energy delivery, agent deliver, data recording and/or other function) of the multiple implantable devices 200 is performed simultaneously, asynchronously, and/or sequentially. The implantable devices 200 can be part of a network including one or more external devices 500 (e.g., external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single external device 500 and/or by multiple external devices 500, which can further be synchronized (e.g., to a single clock). Each implantable device 200 of implantable system 20 can receive a power signal and/or a data signal from one or more external devices 500. In some embodiments of the multi-point ready implantable system 20, each implantable device 200 comprises a unique ID, such that each implantable device 200 is individually addressed (e.g., receive unique signals from external system 50). In some embodiments, external system 50 transmits high-bandwidth signals to implantable system 20, such that time-domain multiple access communication is performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g., two components comprising or positioned in different housings), can be attached to each other by a connecting filament as defined hereabove. In some embodiments, a connecting filament comprises a user-attachable (e.g., clinician-attachable) connector on at least one end. The filament connector is configured to operably attach to a mating connector on a component (e.g., a housing 210) of an implantable device 200.

Each implantable device 200 is configured to receive power and/or data (e.g., implantable system 20 configuration data) from one or more external devices 500. In some embodiments, one or more implantable devices 200 are configured to receive both power and data (e.g., simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more stimulation elements 260, configured to stimulate, deliver energy to, deliver an agent to, record information from and/or otherwise interface with the patient. Alternatively or additionally, the one or more stimulation elements 260 can be configured as a sensor, such as to record patient information. Each implantable device 200 can comprise housing 210, receiver 230, controller 250, energy storage assembly 270 and/or one or more antennas 240, each described in detail herein. Each stimulation element 260 can comprise a sensor and/or any transducer, as described in detail herein. One or more stimulation elements 260 can be positioned on a lead, lead 265 shown (e.g., a flexible filament including wires or other conductors that connect each stimulation element 260 to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can comprise one or more other functional elements, such as functional elements 299*a* and 299*b* described herein. Each implantable device 200 can further comprise one or more anchoring or other fixation elements, anchor element 223 shown, as described in detail herebelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g., patient physiologic information recorded by one or more stimulation elements 260 configured as a physiologic sensor), or implantable device 200 information (e.g., data recorded by one or more stimulation elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more stimulation elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g., a flexible or foldable printed circuit board). In some embodiments, one or more antennas 240 and/or other components (e.g., a functional element 299) are positioned outside of housing 210, such as when at least one antenna 240 or other component is operably connected to one or more components (e.g., electrical components) positioned within housing 210 via a tether comprising one or more electrical conduits.

Housing 210 can comprise one or more shapes and/or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm. Housing 210 can comprise a wall thickness between 0.1 mm and 1.0 mm, such as a wall thickness between 0.2 mm and 0.5 mm, such as a wall thickness of approximately 0.3 mm. Housing 210 can comprise a displacement volume less than or equal to 2000 $mm^3$, such as less than or equal to 600 $mm^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; platinum iridium; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g., shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending U.S. patent application Ser. No. 17/412,044, titled "Medical Apparatus Including an Implantable System and an External System", filed Aug. 25, 2021.

In some embodiments, one or more inner or outer surfaces (or portions of surfaces) of housing 210 includes an insulating and/or shielding layer (e.g., a conductive electromagnetic shielding layer), such as inner coating 219*a* and/or outer coating 219*b* shown (singly or collectively coating 219). Coating 219 can comprise an electrically insulating and/or a thermally insulating layer or other coating. In some embodiments, one or more portions of housing 210 comprise an electrically shielding coating, coating 219, while other portions are transmissive to electromagnetic signals such as radiofrequency signals.

In some embodiments, housing 210 comprises an array of feedthroughs, not shown. In some embodiments, housing 210 is surrounded (e.g., partially or fully surrounded) by a covering, such as a flexible and/or non-conductive covering, such as a covering made of an elastomer.

In some embodiments, implantable device 200 and/or another component of apparatus 10 can include one or more features to prevent or at least reduce migration of implant 200 within the patient's body. In some embodiments, one or more implantable devices 200 comprises one or more anchor elements configured to secure one or more portions of implantable device 200 to tissue (e.g., anchor element 223 described hereabove and/or an anchor element in an overmold positioned about a portion of housing 210). Anchor element 223 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these. While anchor element 223 is shown proximate housing 210 (e.g., to fixedly attach housing 210 to tissue), in some embodiments anchor element 223 surrounds or is otherwise proximate lead 265 (e.g., to fixedly attach lead 265 to tissue). In some embodiments, anchor element 223 comprises a porous mesh that surrounds all or a portion of housing 210. The porous mesh can be configured to promote tissue ingrowth, such as to prevent or at least limit ("prevent" herein) migration of housing 210 when implantable device 200 is implanted in the patient. In some embodiments, anchor element 223 comprises a mesh that is attached to the top side of implantable device 200 (side in closest proximity to the patient's skin), such as to prevent housing 210 from migrating away from the patient's skin (e.g., prevent from migrating deeper into the patient).

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g., two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 300 and 900 relative to each other, such as between 400 and 90°, approximately 30°, approximately 450 and/or approximately 600 relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g., a substrate comprising rigid portions and hinged portions). In some embodiments, the substrate is folded or otherwise pivoted to position the various antennas 240 on differently oriented planes, such as multiple planes oriented between 5° and 900 relative to each other, such as two antennas 240 positioned on two planes oriented between 300 and 900 or between 400 and 900 relative to each other, or three antennas 240 positioned on three planes oriented between 5° and 600 relative to each other. Two or more antennas 240 can be positioned on two or more different planes that are approximately 450 relative to each other, or approximately 600 or approximately 900 relative to each other.

Implantable device 200 can comprise three antennas 240. In some embodiments, a first antenna 240 comprises an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g., positioned on two relatively orthogonal planes). In some embodiments, a first antenna (e.g., an electrical dipole antenna) is positioned outside of housing 210, while a second antenna (e.g., a loop antenna) and a third antenna (e.g., a loop antenna) are each positioned on, in and/or within housing 210. In some embodiments, implantable device 200 comprises one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be arranged as follows: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's co-pending U.S. patent application Ser. No. 17/240,629, titled "Method and Apparatus for Minimally Invasive Implantable Modulators", filed Apr. 26, 2021.

One or more antennas 240 can be positioned inside of housing 210. Alternatively or additionally, one or more antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g., rechargeable batteries) and/or capacitors (e.g., a supercapacitor). Energy storage assembly 270 can be configured to provide power to one or more of: one or more stimulation elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 μF and 10 F, such as a capacitance between 1 μF and 1.0 mF, or between 1 μF and 10 μF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g., maintain delivery of stimulation energy and/or delivery of an agent) without the use (e.g., sufficient proximity) of an associated external device 500. A capacitor or other energy storage element (e.g., a battery) can be chosen to provide sufficient energy to maintain operation for at least 30 seconds, at least 2 minutes, at least 5 minutes, at least 30 minutes, and up to several hours or more (e.g., during showering, swimming, or other physical activity). In some embodiments, energy storage assembly 270 is configured to provide continuous and/or intermittent stimulation energy for at least one charge-balanced pulse (e.g., for the duration of at least one charge-balanced pulse). In some embodiments, a capacitor, battery, or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g., an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more stimulation elements 260 to deliver stimulation energy during subsequent (intended or unintended) unavailability of one or more external devices 500 (e.g., an external device 500 is intentionally removed or unintentionally falls off or otherwise loses its position sufficiently proximate one or more implantable devices 200). An energy storage assembly 270 comprising one or more high-capacity energy storage components can be beneficial in applications where therapy interruption provides a significant risk or is otherwise relatively unacceptable, such as for life support therapies, cardiac resynchronization therapies, and the like. The high-capacity energy storage components of energy storage assembly 270 can be positioned in an assembly positioned within housing 210, on an inner or outer surface of housing 210, within a separate housing, and/or within lead 265.

In some embodiments, during use (e.g., during period of providing stimulation or other function) implantable device 200 receives power regularly from external system 50 (e.g., relatively continuously while implantable device 200 delivers stimulation energy), and energy storage assembly 270 comprises a relatively small battery or capacitor, such as a battery or capacitor that has an energy storage capacity of less than or equal to 0.6 Joules, 7 Joules or 40 Joules.

One or more controllers 250 (singly or collectively controller 250) can be configured to control one or more stimulation elements 260, such as a stimulation element 260 comprising a stimulation-based transducer (e.g., an electrode or other energy delivery element) and/or a sensor (e.g., a physiologic sensor and/or a sensor configured to monitor an implantable device 200 parameter). In some embodiments, controller 250 is configured to transmit a stimulation signal (e.g., transmit stimulation energy configured in one or more stimulation waveforms) to one or more stimulation elements 260 (e.g., one or more stimulation elements 260 comprising an electrode and/or other energy delivery element), independent of the power signal received by one or more antennas 240 (e.g., independent of power transmitted by external system 50), such as by using energy stored in energy storage assembly 270. In these embodiments, the power signal and/or the RF path for the power signal can be modified to optimize power efficiency (e.g., by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g., by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g., unaffected). In some configurations, the stimulation signal being delivered by one or more implantable devices 200 is insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; stimulation element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these. Controller 250 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, controller 250 comprises a memory storage component that includes instructions, such as instructions used by controller 250 to produce a stimulation waveform and/or perform an algorithm, each as described herein.

In some embodiments, one or more stimulation elements 260 comprise a stimulation element configured to deliver energy (e.g., one or more electrodes configured to deliver monopolar or bipolar electrical energy) to tissue, and controller 250 is configured to control the energy delivery, such as to control (e.g. provide, determine, and/or adjust) one or more stimulation parameters. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described in applicant's co-pending U.S. patent application Ser. No. 17/372,095, titled "Apparatus with Enhanced Stimulation Waveforms", filed Jul. 9, 2021. In some embodiments, stimulation (e.g., stimulation comprising high frequency and/or low frequency signal components) is varied randomly to eliminate or at least reduce synchrony of neuronal firing with the stimulation signal (e.g., to reduce paresthesia or other patient discomfort). In some embodiments, one or more stimulation elements 260 comprise a stimulation element configured to stimulate a target (e.g., nerve tissue such as spinal nerve tissue and/or peripheral nerve tissue). The amount of stimulation delivered to the target can be controlled by varying a parameter selected from the group consisting of: stimulation element 260 size and/or configuration (e.g., electrode size and/or configuration); stimulation element 260 shape (e.g., electrode shape, magnetic field generating transducer shape or agent delivering element shape); shape of a generated electric field; shape of a generated magnetic field; stimulation signal parameters; and combinations of one or more of these.

In some embodiments, one or more stimulation elements 260 comprise an element configured to deliver electrical energy to tissue (e.g., one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.1 mA and 15 ma, between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g., greater than 10 μF), in order to pass the stimulation waveform with minimal filtering. In some embodiments, apparatus 10 is configured to perform active charge balancing. In some embodiments, an implantable device 200 comprises a precise resistor in series with a stimulation electrode-based stimulation element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g., a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g., pulses delivered within a train or a burst). Implantable device 200 can comprise a precise series resistance comprising an "on-chip" trimmed resistor or an "off-chip" resistor. In some embodiments, implantable device 200 comprises a bank of trimmed resistors that are used to control the net series resistance, such as to adjust resistance based on stimulation amplitude requirements (e.g., to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse.

The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to the discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more stimulation elements 260 configured as a stimulation element (e.g., such that one or more stimulation elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g., symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g., an operator customized waveform), such as by adjusting amplitude at specified time steps (e.g., for one or more pulses). In some embodiments, controller 250 is configured to generate a waveform including one or more random parameters (e.g., random timing of pulses or random changes in frequency, rate of change or amplitude).

In some embodiments, controller 250 is configured to provide a stimulation signal comprising waveforms and/or pulses repeated at a frequency (e.g., includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g., signal) between 1 kHz and 20 kHz. In some embodiments, controller 250 is configured to produce a stimulation signal comprising a mix and/or modulation of low frequency and high frequency signals, which comprise any of the waveform types, shapes, and other configurations. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, stimulation element 260 drivers (e.g., electrode drivers) of controller 250, and/or other components of implantable device 200. The clamping circuit can improve pulse shape by offering additional control and/or configuration of rise and fall times in the shape of the waveform (e.g., to create rapid rise or fall times). In some embodiments, the clamping circuit can be configured to limit the rise and/or fall time to be less than or equal to one-tenth (10%) of the pulse width of an applied stimulation pulse (e.g., less than or equal to 1 μsec rise and/or fall time for a 10 μsec stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232, and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one or more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g., to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable devices 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and that converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that is used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or it can be further boosted by a DC-DC converter or boost converter. In some embodiments, rectifier 232 comprises diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more stimulation elements 260. Lead 265 can comprise one or more stimulation elements 260 configured as a stimulation element (e.g., an electrode configured to deliver electrical energy in monopolar or bipolar mode or an agent delivery element such as an output port fluidly connected to a reservoir within housing 210). Alternatively or additionally, lead 265 can comprise one or more stimulation elements 260 and/or functional elements 299*b* that is configured as a physiologic sensor (e.g., an electrode configured to record electrical activity of tissue or another physiologic sensor as described herein). Alternatively or additionally, lead 265 can comprise one or more stimulation elements 260 and/or functional elements 299*b* that is configured to transmit signals through tissue to external system 50, such as through body conduction.

In some embodiments, implantable device 200 comprises a connector, connector 215, that operably attaches (e.g., electrically attaches) one or more stimulation elements 260 to one or more components (e.g., electronic components) internal to housing 210 (e.g., to transfer power and/or data therebetween). In some embodiments, connector 215 is operably attached (e.g., in a manufacturing process) or attachable (e.g., in a clinical procedure) to lead 265 as shown in FIG. 1. Alternatively, connector 215 can be operably attached and/or attachable to a lead connection assembly, assembly 280, which in turn can be attached to a lead 265. In some embodiments, connector 215 passes through an opening in housing 210, in a feed-through arrangement. In some embodiments, an overmold or other sealing element, sealing element 205 shown, provides a seal about connector 215, the opening in housing 210 and/or the interface between connector 215 and housing 210.

In some embodiments, lead 265 comprises a removable stylet configured to aid in the implantation of lead 265, such as is described in applicant's co-pending U.S. patent application Ser. No. 17/412,044, titled "Medical Apparatus Including an Implantable System and an External System", filed Aug. 25, 2021. In some embodiments, implantable system 20 comprises more than one lead 265, comprising one or more stimulation elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm, such as a lead with a diameter of approximately 1.35 mm. In some embodiments, lead 265 comprises a length between 3 cm and 60 cm, such as a length between 6 cm and 30 cm. One or more leads 265 can include between 2-64 stimulation elements 260, such as when a lead 265 comprises between 2 and 64 electrodes, such as between 4 and 32 electrodes. In some embodiments, lead 265 comprises a paddle lead. In some embodiments, lead 265 comprises a single or multi-lumen catheter, such as when an attached implantable device 200 is configured as an agent delivery apparatus as described herein (e.g., a stimulation element 260 configured as a catheter comprises at least a portion of lead 265).

In some embodiments, lead 265 comprises one or more tines, such as tines 266 shown. Tines 266 can be configured to anchor or otherwise stabilize ("anchor" or "stabilize" herein) lead 265 relative to patient tissue, such as to prevent undesired movement during and/or after an implantation procedure for lead 265. One or more tines 266 can be configured to biodegrade after implantation in the patient, such that the stabilization provided is temporary. Tines 266 can be configured to biodegrade over a time period of approximately 4 to 12 weeks. In some embodiments, biodegradable tines 266 are configured to be incorporated when lead stimulation elements 260 are positioned to stimulate a peripheral nerve (e.g., lead 265 is implanted such that one or more stimulation elements 260 are positioned proximate one or more peripheral nerves).

In some embodiments, one or more tines 266 are configured to be deployed, such as via an operator-accessible control.

One or more stimulation elements 260 (singly or collectively stimulation element 260) and/or functional element 299 (e.g., functional element 299*a* and/or 299*b*) can comprise one or more sensors, transducers and/or other functional elements. In some embodiments, one or more stimulation elements 260 and/or functional elements 299 comprise at least one sensor and/or at least one transducer (e.g., a single stimulation element 260 or multiple stimulation elements 260). In some embodiments, stimulation element 260 and/or functional element 299 comprises a functional element configured to provide a therapy, such as one or more stimulation elements 260 configured to deliver an agent to tissue (e.g., a needle or catheter), to deliver energy to tissue and/or to otherwise therapeutically affect tissue. In some embodiments, stimulation element 260 and/or functional element 299 comprises one or more functional elements configured to record patient information, such as when stimulation element 260 and/or functional element 299 comprises one or more sensors configured to measure a patient physiologic parameter, as described herein. In some embodiments, stimulation element 260 and/or functional element 299 comprises one or more sensors configured to record an implantable device 200 parameter, also as described herein.

One or more stimulation elements 260 can be positioned on lead 265 as shown in FIG. 1. Alternatively or additionally, one or more stimulation elements 260 can be positioned on housing 210. One or more functional elements 299 can be positioned on lead 265 (e.g., functional element 299*b* shown) and/or positioned on and/or within housing 210 (e.g., functional element 299*a* shown).

Stimulation element 260 can comprise one or more stimulation elements positioned at one or more internal body locations. Stimulation element 260 can comprise one or more stimulation elements positioned to interface with (e.g., deliver energy to and/or record a physiologic parameter from) spinal cord tissue, spinal canal tissue, epidural space tissue, spinal root tissue (dorsal or ventral), dorsal root ganglion, nerve tissue (e.g., peripheral nerve tissue, spinal nerve tissue or cranial nerve tissue), brain tissue, ganglia (e.g., sympathetic or parasympathetic) and/or a plexus. In some embodiments, stimulation element 260 comprises one or more elements positioned proximate and/or within one or more tissue types and/or locations selected from the group consisting of one or more nerves; one or more locations along, in and/or proximate to the spinal cord; peripheral nerves of the spinal cord including locations around the back; the knee; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the stimulation element 260 is positioned proximate to and/or within. In some embodiments, apparatus 10, implantable device 200 and/or stimulation element 260 are configured to stimulate spinal nerves, peripheral nerves and/or other tissue as described in applicant's co-pending U.S. patent application Ser. No. 16/993,999, titled "Apparatus for Peripheral or Spinal Stimulation", filed Aug. 14, 2020.

In some embodiments, stimulation element 260 and/or functional element 299 comprises one or more sensors configured to record data representing a physiologic parameter of the patient. Stimulation element 260 and/or functional element 299 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 (e.g., via stimulation element 260, functional element 299, and/or functional element 599) can be configured to record a patient parameter (e.g., patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity (e.g., as measured using EMG); skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, stimulation element 260 and/or functional element 299 comprises one or more sensors configured to record data representing a parameter of implantable device 200. In these embodiments, stimulation element 260 and/or functional element 299 can comprise one or more sensors selected from the group consisting of: an energy sensor; a voltage sensor; a current sensor; a temperature sensor (e.g., a temperature of one or more components of implantable device 200); a contamination detector (e.g., to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g., via implantable controller 250, programmer 600 and/or diagnostic assembly 62 described herebelow) the data recorded by stimulation element 260 and/or functional element 299 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A stimulation element 260 can be configured to record temperature, such as when apparatus 10 is configured to deactivate or otherwise modify the performance of an implantable device 200 when the recorded temperature exceeds a threshold.

In some embodiments, one or more stimulation elements 260 comprise a transducer configured to deliver energy to tissue, such as to treat pain and/or to otherwise stimulate or affect tissue. In some embodiments, stimulation element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g., delivering mechanical energy to tissue); a tissue manipulating element; a heat generating element; a cooling (e.g., cryogenic or otherwise heat extracting energy) element; an agent delivery element such as a pharmaceutical drug delivery element; and combinations of one or more of these.

In some embodiments, one or more stimulation elements 260 comprises a drug or other agent delivery element, such as a needle, port, iontophoretic element, catheter, or other agent delivering element that is connected to a reservoir of agent positioned within housing 210 (e.g., reservoir 225 described herebelow). In some embodiments, one or more stimulation elements 260 comprise a drug eluting element configured to improve biocompatibility of implantable system 20.

In some embodiments, one or more stimulation elements 260 comprise one or more electrodes configured to deliver energy to tissue and/or to sense a patient parameter (e.g., electrical activity of tissue or other patient physiologic parameter). In these embodiments, one or more stimulation elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 (e.g., via stimulation element 260, functional element 299, and/or functional element 599) is configured to both record one or more patient parameters, and also to perform a medical therapy (e.g., stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more stimulation elements 260 comprise an agent delivery element, such as a fluid delivery element (e.g., a catheter, a porous membrane, an iontophoretic element or a needle) in fluid communication with a reservoir of the agent positioned within housing 210, such as reservoir 225 described herebelow.

In some embodiments, apparatus 10 comprises one or more tools, tool 60 shown. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g., patient physiologic information) recorded by implantable system 20; patient environment information recorded by implantable system 20; and combinations of one or more of these. Tool 60 can be configured to receive data from wired or wireless (e.g., Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

In some embodiments, tool 60 comprises a user interface of apparatus 10, such as a user interface configured to allow the patient, clinician, or other user to create a set of stimulation parameter settings based on various user input.

Apparatus 10 can include one or more placement tools, positioning tool 67 shown, which can be configured to aid in the positioning and/or maintenance of one or more external devices 500 on the patient's skin (e.g., at a location proximate an implanted implantable device 200).

Apparatus 10 can include one or more imaging devices, imaging device 40 shown, which can comprise one, two, or more imaging devices selected from the group consisting of: a CT scanner; a fluoroscope or other X-ray imaging device; an ultrasound imager; an MRI; and combinations of these. In some embodiments, positioning (e.g., selection of anatomical location for implantation) of one or more portions of device 200 (e.g., one or more leads 265 and/or one or more stimulation elements 260) is performed using image data provided by imaging device 40. In some embodiments, one or more leads 265 and/or stimulation elements 260 are positioned based on both eCAP data (e.g., to indicate proper positioning relative to one or more nerves, as described herebelow in reference to FIGS. 2-10), as well as data provided by imaging device 40 (e.g., a fluoroscope and/or an ultrasound imager). In some embodiments, imaging device 40 comprises a fluoroscope and/or other X-ray imaging device that is used (e.g., by an implanting clinician) to position leads 265 and/or stimulation elements 260 (e.g., with or without the use of eCAP data). In some embodiments, imaging device 40 comprises an ultrasound imager that is used (e.g., by an implanting clinician) to position leads 265 and/or stimulation elements 260 (e.g., with or without the use of eCAP data). In some embodiments, placement of one or more leads 265 and/or one or more stimulation elements 260 (e.g., proximate one or more peripheral nerves or other body nerves to be stimulated) is performed using an imaging device 40 (e.g., a fluoroscope or other X-ray imaging device) that does not allow visualization (e.g., adequate visualization) of nerve tissue (e.g., the nerve tissue to be stimulated). In these embodiments, apparatus 10 can be configured to utilize at least data from one or more eCAP measurements, as described herein, in order to identify (e.g., via algorithm 15 described hereinbelow), and/or allow a clinician to identify. a proper implant location for the one or more leads 265 and/or the one or more stimulation elements 260. For example, in peripheral nerve stimulation applications, where nerve trajectory is not sufficiently apparent under X-ray visualization, apparatus 10 can be configured (e.g., via algorithm 15 described hereinbelow) to identify an implant location for elements 260 using both the X-ray data and eCAP measurement data (e.g., such that the one or more elements 260 are sufficiently proximate a target nerve to effectively stimulate the nerve during subsequent stimulation energy delivery).

Apparatus 10 can include one or more implantation tools, implantation tool 65 shown. Implantation tool 65 can comprise an introducer, tunneler, and/or other implantation tool constructed and arranged to aid in the implantation of housing 210, implantable antenna 240, lead 265 and/or one or more stimulation elements 260. Implantation tool 65 can comprise a tool as described in reference to FIGS. 14A-14D herein. In some embodiments, implantation tool 65 comprises a component configured to anchor implantable device 200 to tissue, such as a mesh or wrap that slides around at least a portion of implantable device 200 and is configured to engage tissue (e.g., via tissue ingrowth) or be engaged with tissue (e.g., via suture or clips).

In some embodiments, one or more components (and/or portions of components) of implantation tool 65 comprises a lubricious coating and/or a lubricous material ("lubricious coating" herein), such as to reduce tissue trauma and/or reduce pain to the patient. For example, implantation tool 65 can comprise an introducer, tunneler, pocket formation tool, needle, and/or other insertion tool with at least a portion comprising a lubricious coating configured to ease insertion of the tool. Typical coatings and materials include but are not limited to: a polytetrafluoroethylene coating or material; a hydrophilic coating or material; and combinations of these.

In some embodiments, one or more components (and/or portions of components) of implantation tool 65 comprises one or more "visualizable portions", such as a radiopaque portion that is visible in X-ray imaging (e.g., fluoroscopy), an ultrasonically visible portion that is visible in ultrasound imaging, and/or other portion that can be visualized by an imaging device (e.g., imaging device 40 described herein). For example, implantation tool 65 can comprise an introducer including an ultrasonically visible or otherwise visible portion that is used to position the introducer, such as during the implantation of lead 265 or another portion of implantable device 200.

In some embodiments, lead 265 comprises a paddle lead or other stimulating lead and implantation tool 65 comprises an introducer (e.g., a needle or an extended-width introducer) configured to deliver at least a distal portion of lead 265 into an epidural space of a patient. Implantation tool 65 can comprise an introducer comprising a Tuohy needle, such as a Tuohy needle of 12 gauge or smaller. Implantation tool 65 can comprise a handle for manipulating lead 265. Implantation tool 65 can be configured to place lead 265 at an entry point above the lumbar spinal column (e.g., between L1 and L2 vertebrae). Implantation tool 65 can include extension tubing used to insert lead 265. Implantation tool 65 can comprise a tool as described in reference to FIGS. 14A-14D herein. Implantation tool 65 can comprise (e.g. further comprise) a tool configured to anchor lead 265, such as when implantation tool 65 comprises sutures, clips, other anchoring elements and/or an anchor securing tool (e.g., a needle or a stapling device), such as to secure lead 265 in subcutaneous tissue. Lead 265 and/or implantation tool 65 can comprise extension tubing used to place lead 265, such as extension tubing that remains in place after removal of an introducer of implantation tool 65. Implantation tool 65 can be configured to place lead 265 against the dura of the spinal cord of the patient.

In some embodiments, implantation tool 65 and/or lead 265 are constructed and arranged to implant lead 265 to stimulate one or more multifidus (MF) muscle fascicles, such as at least three sets of multifidus muscle fascicles. Lead 265 can be secured to a vertebra (e.g., on the transverse process, lamina or vertebral body). Lead 265 can be placed via implantation tool 65 such that one or more stimulation elements 260 (e.g., electrodes) are positioned within the multifidus muscle structures. One or more stimulation elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Stimulation elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, stimulation elements 260 are positioned to cause transvascular stimulation (e.g., transvascular stimulation from arteries and/or veins in a leg or arm). In some embodiments, stimulation elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, stimulation elements 260 are configured to deliver stimulation energy to contract the multifidus muscle. In some embodiments, stimulation elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool 60 comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g., an RF transmitter), magnetic coupling, inductive coupling; capacitive coupling and/or other wireless transmission means.

Apparatus 10 can include one or more positioning devices, such as patient attachment device 70 shown in FIG. 1, that is used to attach one or more components of external system 50 to a location on or at least proximate the patient. In some embodiments, patient attachment device 70 is constructed and arranged as described in applicant's co-pending U.S. patent application Ser. No. 17/187,654, titled "Method and Apparatus for Neuromodulation Treatments of Pain and Other Conditions", filed Feb. 26, 2021.

Patient attachment device 70 can comprise one or more elements configured to attach one or more external devices 500 and/or programmer 600 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive; adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g., at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 600; and combinations of one or more of these. In some embodiments, patient attachment device 70 comprises multiple pockets, such as to allow repositioning of an external antenna 540, programmer 600, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

In some embodiments, patient attachment device 70 and/or external device 500 can be configured to prevent adversely affecting portions of the skin contacted by either device. Alternatively or additionally, patient attachment device 70 and/or external device 500 can be configured to clean and/or to promote healing of one or more skin-contacting portions. For example, patient attachment device 70 can include an agent (e.g., a coating or other included agent) selected from the group consisting of: a bactericidal agent; an anti-fungal agent; and combinations thereof.

In some embodiments, an anchoring-based tool, patient attachment device 70, is used on a patient-by-patient basis, such as when used on overweight patients and/or to otherwise avoid migration of implantable device 200 sideways and/or downward (e.g., into fat tissue).

Apparatus 10 can comprise a device configured to operate (e.g., temporarily operate) one or more implantable devices 200, such as trialing interface 80 shown in FIG. 1. Trialing interface 80 can be configured to wirelessly deliver power to an implantable device 200, wirelessly deliver data to an implantable device 200, and/or wirelessly receive data from an implantable device 200. Trialing interface 80 can be configured to interface with one or more implantable devices 200 during an implantation procedure in which one or more implantable devices 200 are implanted in a patient (e.g., a sterile clinical procedure in which an implantable device 200 comprising a pre-attached lead 265 is implanted in a patient). Trialing interface 80 can be configured to be sterilized one or more times. Trialing interface 80 can comprise one or more antennas, such as an antenna similar to antenna 540 of an external device 500. Trialing interface 80 can comprise a transmitter, such as a transmitter similar to transmitter 530 of external device 500, and a power supply, such as a power supply similar to power supply 570 of external device 500. In some embodiments, trialing interface 80 is of similar construction and arrangement to the trialing interface described in applicant's co-pending U.S. patent application Ser. No. 17/187,654, titled "Method and Apparatus for Neuromodulation Treatments of Pain and Other Conditions", filed Feb. 26, 2021. In some embodiments, trialing interface 80 includes a housing to be positioned proximate at least a portion of implantable device 200, such as a housing 210 that surrounds an antenna and a transmitter that is configured to operatively couple to (e.g., transmit power and/or data to) one or more antennas 240 of one or more implantable devices 200.

In some embodiments, trialing interface 80 is constructed and arranged as described an applicant's co-pending U.S. patent application Ser. No. 17/379,928, titled "Stimulation Apparatus", filed Jul. 19, 2021.

As described hereabove, trialing interface 80 can be used in clinical procedures (e.g. used in a trialing session portion of a clinical procedure) in which an implantable device 200 including a pre-attached lead 265 is implanted. In some embodiments, implantable device 200 includes an attachable lead 265, and apparatus 10 includes a trialing interface configured for use with an attachable lead, trialing interface 90. Trialing interface 90 can be configured to operably (e.g., electrically) attach to lead 265, such as to deliver stimulation energy via a wired connection during a trialing procedure, as described herein. For example, trialing interface 90 can deliver stimulation energy to one or more stimulation elements 260 of lead 265 during a trialing procedure in which proper position of stimulation element 260 is confirmed and/or modified, and/or one or more stimulation waveforms are tested. Trialing interface 90 can include interface connector 95, which can comprise a connector that is configured to operably attach (e.g., electrically attach) trialing interface 90 to lead 265 (e.g., after lead 265 has been implanted in tissue of the patient). Connector 95 can be configured to be used in a single trialing procedure (e.g., on a single patient), while the remainder of trialing interface 90 can be reused (e.g., in multiple trialing procedures for multiple patients). Trialing interface 90 can comprise a device that is sterilized, and it can be a device that can be re-sterilized (e.g., to be used in multiple sterile clinical procedures). In some embodiments, trialing interface 80 and trialing interface 90 include similar components, (e.g., similar components used to create similar stimulation waveforms to be used in a trialing procedure).

In some embodiments, one or more implantable devices 200 of implantable system 20 comprises an implantable transmitter configured to transmit data, such as to transmit data (e.g., stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 62 shown in FIG. 1. In some embodiments, programmer 600 and/or implantable controller 250 comprise all or a portion of diagnostic assembly 62. Diagnostic assembly 62 can be configured to assess, monitor, determine and/or otherwise analyze patient information and/or implantable device 200 information, such as when one or more stimulation elements 260, functional elements 299, and/or functional elements 599 are configured as a sensor configured to record patient information (e.g., patient physiologic information and/or patient environment information) and/or apparatus 10 information (e.g., implantable device 200 information) as described herein. Diagnostic assembly 62 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g., such as during a calibration procedure). The BER can be tracked by the implant controller 250 or programmer 600, such as to monitor and keep track of any trends in the link. This trend can be used to adjust the link and/or provide feedback to an operator of apparatus 10 (e.g., the patient), in case the link cannot be automatically adjusted to compensate for a negative trend (e.g., such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 62 can be configured to analyze a result of stimulation energy delivered by implantable device 200, such as when a stimulation element 260 comprises an electrode to record electrical activity of tissue (e.g., in addition to delivering electrical energy to stimulate tissue). A stimulation element 260, a functional element 299, and/or a functional element 599 can comprise a sensor configured to record neural activity and/or muscular activity, and the diagnostic assembly configured to analyze the recorded sensor data. In some embodiments, diagnostic assembly 62 is configured to analyze impedance, such as when a stimulation element 260, a functional element 299, and/or functional element 599 comprises a sensor configured to record data related to impedance, such as when implantable device 200 performs a frequency sweep, performs an impulse response and/or compares voltage and current of a stimulation waveform. In some embodiments, diagnostic assembly 62 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 62 is configured to test or otherwise assess the link between one or more implantable antennas 240 and one or more external antennas 540 (e.g., during a procedure in which one or more implantable devices 200 are implanted in a patient). In these embodiments, diagnostic assembly 62 can be configured to perform a test prior to anchoring housing 210 to tissue (e.g., prior to initial or final suturing into tissue such as the fascia layer). For example, lead 265 can be implanted at a location to stimulate target tissue (e.g., one or more nerves identified to treat pain or another patient condition). Prior to suturing housing 210 in its implant location, diagnostic assembly 62 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 62 can comprise a handheld assembly (e.g., a sterile assembly comprising a wand or other handheld housing). Diagnostic assembly 62 can be configured to send a simple signal to one or more implantable devices 200 (e.g., a diagnostic assembly 62 with similar power and/or data transmission capabilities as an external device 500). Each implantable device 200 can respond (e.g., via data sent via an implantable antenna 240 or other transmitter) with information related to the quality of the transmission link (e.g., information about the power received by the one or more implantable devices 200). Diagnostic assembly 62 could provide a user interface (e.g., a speaker, a text screen and/or a video display) that provides quality or other information (go/no go information, digital or other discrete level information, and/or analog information). Diagnostic assembly 62 could be further configured to provide information confirming detection of one or more implantable devices 200, status of one or more implantable devices 200 (e.g., parameter level and/or fault detection status), and/or self-diagnostic status (i.e. diagnostic assembly 62 status).

Each implantable device 200 can be configured to specifically identify and/or specifically reply to diagnostic assembly 62 (e.g., in a different form than communications with an external device 500). Each implantable device 200 can be configured to provide information related to one or more of: the charge and/or discharge rate of energy storage assembly 270 (e.g., the charge and/or discharge rate of a capacitor or battery of energy storage assembly 270); or the frequency of a voltage-controlled oscillator that is driven by an unregulated voltage of power converter 233. Diagnostic assembly 62 can be configured to perform numerous performance tests (e.g., of one or more implantable devices 200 or implantation locations for one or more implantable devices 200), prior to completion of the implantation procedure (e.g., prior to closing one or more incisions).

In some embodiments, apparatus 10 is configured to provide a therapy by delivering stimulation energy to tissue, such as electrical energy delivered to tissue by one or more stimulation elements 260 comprising one or more electrodes. Alternatively or additionally, apparatus 10 can be configured as an agent-delivery apparatus (e.g., a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 599 and/or functional elements 299, respectively (e.g., via one or more tubes). Reservoirs 525 and/or 225 can comprise one or more chambers (e.g., independent chambers configured to separately contain incompatible drugs or otherwise prevent undesired multiple drug interactions). Reservoirs 525 and/or 225 can comprise a volume (e.g., a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g., a peristaltic mechanism, syringe pump or other fluid pump). Reservoirs 525 and/or 225 and can comprise refillable reservoirs (e.g., when reservoir 225 of an implantable device 200 comprises a valved opening such as a silicone septum or a mechanical valve, either accessible via a needle for refilling). The fluidly attached functional elements 599 and/or functional elements 299 can comprise a fluid delivery element selected from the group consisting of: a catheter; a porous membrane; an iontophoretic element; a needle; and combinations of one or more of these. Delivered and/or stored (e.g., in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g., throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g., via a catheter-based functional element 599, functional element 299, and/or stimulation element 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 599 configured as agent delivery elements and/or sensors. The one or more implantable devices 200 can comprise one or more reservoirs 225 described hereabove and/or one or more stimulation elements 260 configured as agent delivery elements and/or sensors.

In some embodiments, apparatus 10 comprises an agent delivery apparatus and agent is delivered into the patient (e.g., into a blood vessel, muscle or subcutaneous tissue) by an external device 500 functional element 599 (e.g., a needle) based on signals recorded by an implantable device 200 functional element 299 and/or stimulation element 260 (e.g., a sensor). Alternatively or additionally, agent can be delivered into the patient (e.g., into a blood vessel, muscle, or subcutaneous tissue) by an implantable device 200 stimulation element 260 (e.g., a needle, catheter, porous membrane or iontophoretic delivery element). The amount of agent delivered by stimulation element 260 can be based on signals recorded by an implantable device 200 stimulation element 260 (e.g., a sensor) and/or an external device 500 functional element **599*a* (e.g., a sensor). External device 500 can provide power to one or more implantable devices 200 and/or it can send data (e.g., sensor data from a functional element 599) to implantable device 200, such as to control agent delivery by implantable device 200**.

Apparatus 10 can be configured to prevent an electromagnetic field (e.g., an electromagnetic field produced by one or more devices not included in apparatus 10 and/or other present in the patient environment) from adversely affecting and/or otherwise affecting the patient treatment and/or patient information recording (e.g., patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding, and other security measures to ensure that interfering signals do not adversely affect the implantable system 20 performance (e.g., stimulation). In some embodiments, external system 50 and/or implantable system 20 incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g., and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its stimulation elements 260 (e.g., electrodes) can be configured to provide localized (e.g., targeted) magnetic and/or electrical stimulation. Combined electrical field stimulation and magnetic field stimulation can be applied by using superposition, and this combination can reduce the overall energy requirement. In some embodiments, implantable apparatus 10 comprises one or more stimulation elements 260 comprising a magnetic field generating transducer (e.g., microcoils or cuff electrodes positioned to partially surround or otherwise be proximate to one or more target nerves). Stimulation elements 260 comprising microcoils can be aligned with nerves to minimize affecting non-targeted tissue (e.g., to avoid one or more undesired effects to non-target tissue surrounding or otherwise proximate the target tissue). In some embodiments, the target tissue comprises dorsal root ganglia (DRG) tissue, and the non-target tissue comprises ventral root tissue (e.g., when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation changes between antennas and/or relative angular misalignment between antennas. In order to compensate for misaligned antennas, electrical beam steering can be included in apparatus 10. Antennas comprising a multi-feed antenna structure and/or those comprising an array of antennas can be incorporated (e.g., into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g., a substrate comprising polyamide, polyimide, liquid crystal polymer (LCP), Rogers, FR4, or a similar material). One or more antennas 540 can be connected to electronics (e.g., a transmitter, receiver, or transceiver) using a flexible waveguide or cable (e.g., 50 ohm 0.047 inch coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g., a piezoelectric actuator) with directional gears configured to translate one or more antennas 240 and/or 540 about one or more axes; a micro-pump with fluid reservoir (e.g., liquid or gas reservoir) configured to hydraulically and/or pneumatically translate one or more antennas 240 and/or 540 about one or more axes, such as by creating a local pressure difference. In some embodiments, a micro-pump with fluid reservoir is used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g., a balloon) positioned between external antenna 540 and tissue. The reservoir can be inflated or deflated to control separation distance of the external antenna 540 from the patient's skin surface.

In some embodiments, implantable system 20 of apparatus 10 is configured to provide paresthesia-reduced (e.g., paresthesia-free) high frequency pain management and rehabilitation therapy (e.g., via delivery of a stimulation signal above 600 Hz or 1 kHz, or other stimulation signal resulting in minimal paresthesia). Apparatus 10 can be configured to provide both low frequency (e.g., <1 kHz) stimulation and high frequency stimulation, such as when providing low frequency stimulation to elicit feedback from a patient during intraoperative or other (e.g., post-implantation) stimulation configuration. For example, trialing interface 80 and/or 90 can be used during an intra-operative titration of stimulation configuration using low frequency stimulation (e.g., to position and/or confirm position of one or more stimulation elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g., via low frequency stimulation and/or high frequency stimulation) is beneficial during stimulation element 260 (e.g., electrode) implantation because a patient can provide feedback to the implanting clinician to ensure that the stimulation elements 260 are positioned close to the target neuromodulation or energy delivery site. This implantation position-optimizing procedure can advantageously reduce the required stimulation energy due to stimulation elements 260 being closer to target tissue, since a minimum threshold for efficacious stimulation amplitude is proportional to the proximity of stimulation elements 260 to target tissue (e.g., target nerves). The patient can inform the clinician of the sensation of paresthesia coverage, and the clinician can adjust stimulation element 260 position to optimize stimulation element 260 location for efficacious treatment while minimizing unintentional stimulation of non-target tissue (e.g., motor nerves or other nerves which are not causing the patient's pain). These paresthesia-inducing techniques (e.g., using low frequency stimulation and/or high frequency stimulation) can be used during or after implantation of one or more implantable devices 200.

In some embodiments, apparatus 10 is configured to deliver low frequency stimulation energy (e.g., electrical energy comprising a low frequency signal) to stimulate motor nerves, such as to improve tone and structural support (e.g., physical therapy). In these embodiments, apparatus 10 can be further configured to provide high frequency stimulation, such as to treat pain (e.g., suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g., electrical energy) to induce paresthesia, which can also be accompanied by the delivery of high frequency stimulation (e.g., to suppress and/or control pain). In some embodiments, apparatus 10 is configured to deliver low frequency stimulation (e.g., electrical energy comprising a low frequency signal)

and burst stimulation, delivered simultaneously or sequentially. The low frequency stimulation and the burst stimulation can be delivered on similar and/or dissimilar stimulation elements 260 (e.g., similar or dissimilar electrode-based stimulation elements 260).

As described herein, apparatus 10 can be configured for treating numerous disease and disorders, such as when apparatus 10 is configured to deliver electrical or other stimulation energy to treat pain (e.g., by delivering electrical or other energy to the spine or other neural location). Apparatus 10 can be configured to stimulate tissue with various stimulation waveforms, such as those described in applicant's co-pending U.S. patent application Ser. No. 17/372,095, titled "Apparatus with Enhanced Stimulation Waveforms", filed Jul. 9, 2021.

Apparatus 10 can be configured to treat neuropathy, neuralgia and/or other nerve pain that is related to: surgery; trauma; infection (e.g., a herpetic infection); and/or diabetes (e.g., diabetic neuropathy). One or more stimulation elements 260 can be configured to deliver stimulation energy (e.g., electrical energy, magnetic energy, light energy, thermal energy, sound energy, and/or chemical energy (e.g., energy from a drug or reagent) to nerve tissue such as tissue of the central nervous system and/or peripheral nervous system. One or more leads 265 (each comprising one or more stimulation elements 260) can be implanted in and/or proximate the spinal cord, the groin and/or a joint such as the hip. For example, apparatus 10 can be configured to treat one or more of: post-surgical neuralgia (e.g., following hernia repair such as a hernia repair including an implanted mesh); headache (e.g., due to occipital neuralgia); post-herpetic neuralgia; chronic pelvic and/or hip pain; knee pain; and combinations of one or more of these.

To treat pain related to hernia or hernia repair, one or more stimulation elements 260 (e.g., on a lead 265 and/or on a housing 210) can be positioned to stimulate tissue of the peripheral nervous system and/or the central nervous system. In some embodiments, one or more stimulation elements 260 are positioned to stimulate the cutaneous branch of the ilioinguinal, inguinal and/or genital branch of the genitofemoral nerves. In some embodiments, one or more stimulation elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these. In some embodiments, apparatus 10 is configured to treat hernia pain by delivering a low frequency stimulation signal (e.g., an electrical signal less than or equal to 1 kHz delivered by one or more electrode-based stimulation elements 260). Alternatively or additionally, apparatus 10 can treat hernia pain with a high frequency stimulation signal, such as a signal comprising a frequency greater than 1 kHz. Stimulation can be accomplished either via subcutaneous field stimulation and/or by stimulation elements 260 positioned adjacent or at least near the nerves and/or their branches. In some embodiments, stimulation is accomplished transvascularly (e.g., stimulation including low and/or high frequencies).

The apparatus of the present inventive concepts can be configured to stimulate the ilioinguinal nerve, genitofemoral nerve and/or iliohypogastric nerves, such as to ameliorate pain following hernia repair. One or more leads 265 (e.g., one or more leads 265 comprising one or more electrode-based or otherwise stimulation-based stimulation elements 260) can be inserted over the inguinal region (which may include the inguinal ring) to stimulate any or all three of these nerves (e.g., in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more stimulation elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g., the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g., transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g., percutaneous or paddle) including stimulation-based stimulation elements 260 can be placed over the dorsal columns, over the dorsal roots and/or in the dorsal root entry zone, in a unilateral, bilateral and/or midline fashion.

To treat occipital neuralgia, also known as C2 neuralgia, one or more stimulation elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more stimulation elements 260, are implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more stimulation elements 260 are positioned to stimulate the trigeminal and/or occipital nerves. One or more leads 265 can be anchored to the fascia proximate the tissue to be stimulated.

To treat post-herpetic neuralgia (e.g., neuralgia associated with shingles), one or more stimulation elements 260 can be positioned to stimulate corresponding branches of the spinal nerves and/or peripheral nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; accidental bowel leakage; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g., using bilateral and/or unilateral stimulation) one or more of the targets listed below.

In some embodiments, the stimulated targets include the sacral nerves (roots) S2, S3 and/or S4. One or more leads 265 (e.g., each including one or more stimulation-delivering stimulation elements 260) can be positioned to stimulate any or all of the three roots, on a single side or both sides, in any bilateral or unilateral combination. The roots can be accessed, with the patient lying in the prone position, by positioning one or more leads 265 (e.g., percutaneously), with or without the use of fluoroscopy, ultrasound, or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound, or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound, or other imaging modality), up to the cauda equina, where the S2, S3 and/or S4 roots can be stimulated where they enter the spinal cord, and/or the conus medullaris can be stimulated directly (e.g., in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals, and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g., fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g., through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g., fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g., voiding dysfunction). In order to provide stimulation of the tibial nerve, lead 265 can be inserted at a location close to the knee and/or at a location near the ankle. For example, the tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down procedure can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g., a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g., using standard interventional techniques). The tibial nerve can be transvascularly stimulated by the popliteal vein and/or artery (e.g., by placing one or more stimulation elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat pelvic dysfunction, overactive bladder, and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more stimulation elements 260 are positioned to stimulate tissue of the central nervous system or tissue and/or tissue of the peripheral nervous system to treat overactive bladder, such as to stimulate one or more nerves that control and/or are otherwise related to bladder function (e.g., to increase bladder capacity, improve bladder emptying, reduce urge incontinence and/or reduce stress incontinence). For example, one or more stimulation elements 260 are be positioned to stimulate tibial nerve tissue and/or sacral nerve tissue (e.g., at least the S3 nerve root) to treat overactive bladder. In some embodiments, one or more stimulation elements 260 can be positioned to stimulate sacral nerve tissue to treat urinary urgency, urinary frequency (e.g., urinary urgency frequency), and/or painful bladder syndrome. In some embodiments, lead 265 is constructed and arranged to be positioned along one or more locations of the tibial nerve, such as a positioning performed using percutaneous technique (e.g., when lead 265 comprises a cylindrical SCS-type lead) and/or surgical (cut-down) techniques (e.g., when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g., transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more stimulation elements 260 are positioned proximate (e.g., in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g., a lead 265 comprising a lead extension) can be extended underneath the skin (e.g., tunneled) to a second incision (e.g., across the flank to the lower abdomen, across the midline to the buttocks, or low back), and a third incision can be made (e.g., in the abdomen, back or buttocks) where housing 210 can be inserted and connected to lead 265. Alternatively, housing 210 can be inserted at another internal location. If lead 265 is already connected (e.g., attached in manufacturing) to housing 210, lead 265 can be advanced in the opposite direction, such as from the third incision to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g., attached in manufacturing) to housing 210, lead 265 and housing 210 are implanted. In some embodiments, a first lead 265 and a first housing 210 (pre-attached or attachable) are utilized in a dose titration or other "trialing procedure" (also referring to as a "trialing session" herein), and a second lead 265 and housing 210 (pre-attached or attachable) are implanted in the patient for subsequent treatment of the patient.

In some embodiments, one or more stimulation elements 260 are positioned to perform posterior tibial nerve stimulation (PTNS), such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more stimulation elements 260 are positioned to perform retrograde stimulation of the sacral nerve plexus and restore the balance between bladder inhibitory and excitatory control systems of the bladder. One or more stimulation elements 260 can be positioned above the ankle, proximate and/or into the tibial nerve. Implantable device 200 can deliver stimulation energy to the stimulation elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, implantable system 20 is configured to deliver a series of repeated stimulation periods, such as a regimen of approximately: weekly thirty-minute sessions of stimulation for twelve weeks. In some embodiments, implantable system 20 is configured to provide weekly, daily and/or hourly sessions that deliver stimulation for between 10 minutes and 60 minutes. Implantable system 20 can deliver stimulation for any number of minutes per day. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing interface 80 and/or 90 described hereabove, such as to provide power and/or data to one or more implantable devices 200 to confirm acceptable improvement of the patient's overactive bladder (e.g., successful stimulation of one or more sacral nerves, tibial nerves or other tissue), before closing an incision or otherwise fully implanting one or more implantable devices 200. In some embodiments, a temporary stimulation (for overactive bladder or in a trialing procedure for any therapy) is provided for up to one week, up to one month, more than 1 month, more than 2 months, or more than 3 months. In some embodiments, one or more implantable devices 200 are left in place if the temporary stimulation period is successful or unsuccessful (e.g., left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more stimulation elements 260 are positioned to stimulate periurethral muscles. In some embodiments, one or more stimulation elements 260 are positioned to stimulate tissue of the vagina or anus. In some embodiments, one or more stimulation elements 260 are positioned to stimulate sphincter muscles for controlling the bladder, such as two stimulation elements 260 positioned on either side of the urethral orifice. In these embodiments, housing 210 can be implanted in suprapubic region or in the enneum. In some embodiments, lead 265 comprises (e.g., on a distal portion) a pessary ring comprising two stimulation elements 260. In some embodiments, stimulation elements 260 comprise periurethral electrodes configured to stimulate pudendal afferents.

As described above, apparatus 10 can be configured for treating numerous diseases, disorders, or other undesirable patient conditions, such as fecal incontinence. Injury of nerves that sense stool in the rectum can lead to fecal incontinence. In some embodiments, one or more stimulation elements 260 (e.g., one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more stimulation elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 stimulation elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 μsec and 240 μsec (or between 1 μsec and 200 μsec); provides electrical stimulation energy with an amplitude of approximately 0.1V to 8.5V (e.g., providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more stimulation elements 260 (e.g., small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratrochlear; sphenopalatine (SPG); and combinations of one or more of these.

In some embodiments, apparatus 10 is configured to treat neuralgia, such as a neuralgia resulting from surgery (e.g., groin, shoulder, lung and/or amputation), trauma and/or phantom pain, and one or more stimulation elements 260 are positioned to stimulate nerve tissue.

In some embodiments, apparatus 10 is configured to treat neuralgia, such as a neuralgia resulting from groin surgery (e.g., hernia or other groin surgery), and one or more stimulation elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more stimulation elements 260 are positioned to stimulate axial nerve tissue (e.g., one or more stimulation elements 260 positioned on a lead 265 implanted in a suprascapular location).

In some embodiments, apparatus 10 is configured to treat neuralgia, such as a neuralgia resulting from lung surgery, and one or more stimulation elements 260 are positioned to stimulate intercostal nerve tissue.

In some embodiments, apparatus 10 is configured to treat neuralgia, such as a neuralgia associated with carpal tunnel syndrome, and one or more stimulation elements 260 are positioned to stimulate median nerve tissue.

In some embodiments, apparatus 10 is configured to treat neuralgia, such as a neuralgia associated with temporomandibular joint disorder (TMJ), and one or more stimulation elements 260 are positioned to stimulate V2 of trigeminal nerve tissue.

In some embodiments, apparatus 10 is configured to treat neuralgia, such as a facial neuralgia, and one or more stimulation elements 260 are positioned to stimulate trigeminal nerve tissue.

In some embodiments, apparatus 10 is configured to treat neuralgia, such as a leg (sciatic) neuralgia, and one or more stimulation elements 260 are positioned to stimulate nerve tissue proximal a contributing lesion.

In some embodiments, apparatus 10 is configured to treat pelvic pain, such as interstitial cystitis and/or bladder pain, and one or more stimulation elements 260 are positioned to stimulate peripheral nervous system tissue (e.g., pudendal tissue and/or S-2, S-3 and/or S-4 roots) and/or central nervous system tissue (e.g., lower spinal cord and/or S3 neural foramen).

In some embodiments, apparatus 10 is configured to treat pelvic pain, such as anal pain, and one or more stimulation elements 260 are positioned to stimulate peripheral nerve tissue such as pudendal tissue and/or S-2, S-3 and/or S-4 roots.

In some embodiments, apparatus 10 is configured to treat subcutaneous pain, and one or more stimulation elements 260 (e.g., paddle electrodes) are positioned to stimulate nerve tissue.

In some embodiments, apparatus 10 is configured to treat diabetic neuropathy, such as painful diabetic neuropathy, and one or more stimulation elements 260 are positioned proximate the lower spinal cord (e.g., to stimulate S3 nerves) or other body location to stimulate nerve tissue.

In some embodiments, apparatus 10 is configured to treat visceral pain, angina and/or other pain, and one or more stimulation elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g., such that one or more stimulation elements 260 are positioned proximate the nerve to be stimulated). In some embodiments, lead 265 is positioned to stimulate the dorsal root ganglia to treat diabetic neuropathy (e.g., diabetic neuropathy of the hand and/or foot). Lead 265 can be implanted percutaneously and/or surgically as described herein. Lead 265 and/or one or more stimulation elements 260 can comprise a paddle electrode, such as one or more paddle electrodes implanted in the foot, leg and/or arm. Lead 265 and/or one or more stimulation elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g., to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g., each including one or more stimulation elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, stimulation element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius, and soleus muscles where it can be accessed surgically or percutaneously. It then surfaces just as it warps around the anterior aspect of the medial malleolus where it supplies the medial posterior foot in front of heel. The medial sural cutaneous nerve comes off the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more stimulation elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more stimulation elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 is configured to transvascularly stimulate at least one of a median nerve, an ulnar nerve or a radial nerve, and stimulation element 260 comprises one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 is configured to transvascularly stimulate at least one of a median nerve or an ulnar nerve, and stimulation element 260 can comprise one or more electrodes positioned in a vessel selected from the group consisting of: brachial vein; brachial artery; and combinations of one or more of these. In some embodiments, apparatus 10 is configured to transvascularly stimulate the radial nerve, and stimulation element 260 comprises one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and stimulation element 260 comprises one or more electrodes positioned in the basilic vein. In some embodiments, apparatus 10 is configured to transvascularly stimulate the ulnar nerve, and stimulation element 260 comprises one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and stimulation element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g., a paddle lead) in the epidural space. A lead 265 can be placed such that one or more stimulation elements 260 (e.g., one or more electrodes) are positioned from T5-S5, such as to capture the area of pain or reduced circulation of the leg or foot. One or more stimulation elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more stimulation elements 260 (e.g., one or more electrodes attached to one or more leads 265) can be positioned to transvascularly stimulate one or more nerves, such as one or more nerves in the foot, leg and/or arm, such as when the one or more stimulation elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more stimulation elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more stimulation elements 260 (e.g., one or more electrodes attached to one or more leads 265) can be positioned to stimulate dorsal root ganglia that supply the following nerves (e.g., to treat the leg and/or foot): common peroneal (L4-S2); tibial (L4-S3); femoral (L2-L4); and combinations of one or more of these. One or more stimulation elements 260 (e.g., one or more electrodes attached to one or more leads 265) can be positioned to stimulate dorsal root ganglia that supply the following nerves (e.g., to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more stimulation elements 260 stimulate one or more nerves in the leg, arm and/or sacrum. One or more leads 265 can be surgically implanted, such as when lead 265 comprises a paddle electrode positioned near a nerve in the foot, leg, or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g., a paddle lead) in the epidural space. One or more leads 265 can be positioned to provide transvascular stimulation of nerves in the leg or arm, such as when one or more stimulation elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua;

trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g., which arise from C2 and C3); the greater and/or lesser auricular nerves (e.g., which also arise from C2/C3); the third (least) occipital nerve (e.g., which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g., a cylindrical SCS-type lead) can be inserted percutaneously either subcutaneously or under the muscle. Alternatively, surgery (e.g., direct cut-down) can be performed to insert lead 265 (e.g., a cylindrical lead, a paddle lead, a cuff or hemi-cuff electrode) proximate, one and/or around these nerves. Alternatively or additionally, the nerves can be accessed transvascularly as described herein (e.g., when one or more stimulation elements 260 are implanted in a blood vessel). Housing 210 can be implanted anywhere in the head under the skin, including: behind the ear, back of the head, the neck, in the face, and the like, where one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more stimulation elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g., a paddle lead) in the epidural space. One or more leads 265 can be positioned to provide transvascular stimulation of nerves in the leg, torso and/or arm, such as when one or more stimulation elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these. In these embodiments, apparatus 10 can be configured to deliver stimulation to median nerve tissue; ulnar nerve tissue and/or radial nerve tissue.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hypogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, apparatus 10 is configured to treat knee pain. Knee pain from joint degeneration or join replacement surgery can be treated via stimulation of the nerves innervating the knee and/or via stimulation of the tissue surrounding the knee (sometimes referred to as peripheral field stimulation). Apparatus 10 can comprise between one and eight leads 265 whose stimulation elements 260 are placed near and around the knee. In some embodiments, four leads 265 are placed, in locations medial, lateral, superior and inferior to the knee. The leads 265 can be placed subcutaneously for field stimulation, or they can be placed directly adjacent to specific nerve targets. Applicable nerve targets are as follows: medial knee can include medial femoral cutaneous and infrapatellar cutaneous branches of saphenous nerve; lateral knee can include constant articular branches of common peroneal, lateral retinacular nerve; anterior knee can include lateral, medial, and anterior cutaneous femoral nerve, infrapatellar branch of saphenous nerve, medial and lateral retinacular nerve and articular branches of peroneal nerve; posterior knee can include obturator, posterior tibial and sciatic nerves. In addition, the following nerves can be stimulated via stimulation elements 260 to treat knee pain: nerves arising from the tibial nerve such as the superior, middle and inferior genicular nerves; nerves arising from the common peroneal such as the superior lateral, inferior lateral, and recurrent genicular nerves; and nerves arising from the obturator nerve such as the genicular branch of obturator; and nerves arising from the femoral nerve such as the saphenous nerve. Each of these targets can be stimulated transvascularly by one or more stimulation elements 260.

In some embodiments, implantable device 200 has an internal battery or other power supply such that stimulation (e.g., stimulation energy and/or a stimulation agent) is delivered to one or more locations within a patient for an extended time period (e.g., at least 1 hour, at least 1 day, at least 1 month or at least 1 year), without receiving a power transmission (e.g., as described herein from an external device such as external device 500) during that time period. In some embodiments, at least a portion of a single pulse of energy (e.g., at least a single phase) is delivered by implantable device 200 using energy provided by an internal power supply 570 such as a battery or a capacitor. In these embodiments, data can be transmitted by one or more of an external device 500 and/or a programmer 600, such as to activate or modify stimulation being delivered, with or without also transmitting power.

In some embodiments, implantable device 200 comprises one or more components configured to receive transmitted power (e.g., via an external device 500), receive transmitted data (e.g., via an external device 500 and/or programmer 600) and/or deliver stimulation (e.g., deliver stimulation energy and/or a stimulation agent).

In some embodiments, one or more implantable devices 200 are configured to deliver stimulation energy (e.g., via one or more stimulation elements 260 comprising an electrode) with a stimulation waveform comprising one or more high frequency signals (e.g., a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described in applicant's co-pending U.S. patent application Ser. No. 17/372,095, titled "Apparatus with Enhanced Stimulation Waveforms", filed Jul. 9, 2021. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g., a pulse comprising at least a cathodic or anodic portion followed by passive capacitive recovery with an optional open circuit time between the first portion and recovery). In some embodiments, a group of pulses is delivered, each pulse comprising an anodic or cathodic portion that can include charge recovery after each pulse, such as charge recovery comprising active (opposite polarity pulse) recovery, and/or passive (capacitive) recovery. In some embodiments, there is no recovery between pulses, but instead active or passive recovery is included at the end of the set of the first (anodic or cathodic) portions. In some embodiments, single or groups of pulses are provided at time-varying modes of repetition (e.g., regular intervals for a period, then a period of irregular intervals) or at regular intervals with occasional (random) spurious pulses inserted (creating a single irregular event in an otherwise regular series). Non-limiting examples of waveform variations include: a variation in frequency (e.g., frequency of one or more signals of the waveform); variation of a signal amplitude; variation of interval time period (e.g., at time period between pulses or a time period between pulse trains); variation of a pulse width; multiple piecewise or continuous variations of one of more stimulation parameters in a single pulse (e.g., multi-step, multi-amplitude in one "super-pulse"); variation of pulse symmetry (e.g., via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" (e.g., automatically and/or at least semi-automatically by apparatus 10) such as a variation performed temporally (e.g., on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device 200 can be configured to vary a stimulation waveform randomly. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g., paresthesia or other undesired condition) from the stimulation signal. In some embodiments, the amplitude of the stimulation signal can be ramped (e.g., up and/or down), a single time or multiple times (e.g., continuously or intermittently). In some embodiments, a titration procedure is performed to set (e.g., define) one or more stimulation parameters based on avoiding patient discomfort.

In some embodiments, one or more implantable devices 200 are configured to deliver stimulation energy (e.g., via one or more stimulation elements 260 comprising an electrode) with a stimulation waveform comprising one or more waveform patterns. The stimulation waveforms delivered can be configured to treat various conditions of a patient. Each stimulation waveform can comprise a series of continuous pulses, intermittent pulses, and/or spurious pulses (e.g., occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g., comprise an exponential portion), such as dynamic return pulses that exceed a minimum current (e.g., at least 1 mA, 10 mA or 50 mA) for a short duration (e.g., for approximately 1 μsec), and then decay to lower current levels (e.g., a level of approximately 100 nA), with a time constant on the order of 1 μsec to 100 μsec.

The stimulation waveforms delivered by implantable device 200 can comprise one or more high frequencies. The stimulation waveform frequency or other stimulation parameter can be set, adjusted, and/or modified ("set", "adjusted", and/or "modified" herein) to optimize therapeutic benefit to the patient and minimize undesired effects (e.g., paresthesia or other patient discomfort). In some embodiments, a stimulation waveform is adjusted based on a signal produced by a sensor of apparatus 10 (e.g., a sensor of implantable device 200, such as a stimulation element 260 configured as a sensor or other sensor of implantable device 200 as described hereabove). Adjustment of a stimulation waveform parameter can be performed automatically by the implantable device 200 and/or via an external device 500 and/or programmer 600).

In some embodiments, a pulse shape of a stimulation waveform can be varied, such as a pulse shape comprising: a sinusoidal geometry; a square geometry (e.g., a waveform comprising a square wave); a rectangular geometry; a triangular geometry; (e.g., symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g., anodal phase) of a stimulation waveform is varied by implantable device 200.

Inter-pulse gap, the time between one or more pulses (e.g., a biphasic or other multiphasic pulse that is repeated continuously), can be varied systematically and/or randomly by implantable device 200. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly, such as a random variation based on a distribution (e.g., a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g., comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g., varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g., a signal comprising a modulation frequency of 1 Hz). In these embodiments, the depth of modulation would be 33%, where depth of modulation is equal to 1−[lower range/upper range]. In some embodiments, amplitude of delivered current fluctuates between 1 mA and 3 mA (i.e. a depth of modulation of 66%), while in other embodiments, current fluctuates between 0 mA and 10 mA (e.g., a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.10% and 100%.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g., a quiescent period) can be included. In some embodiments, controller 250 comprises one or more reconfigurable stimulation blocks including one or more Howland or other current sources. The one or more current sources (e.g., two or more current sources) can each be attached to a stimulation element 260 (e.g., in a monopolar configuration when the current source is also connected to housing 210 or in a bipolar configuration when the current source is connected to a pair of stimulation elements 260). Alternatively, controller 250 can comprise one or more current sources that are attached to a matrix of switches that selectively connect the one or more current sources to multiple stimulation elements 260 (e.g., connect a single current source to 2, 4, 8, 12 or 16 electrodes). In some embodiments, controller 250 is configured such that a stimulation waveform signal provided to the current source passes through a capacitor (e.g., capacitor C1 shown), the capacitor providing DC balance.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 μsec and 1 msec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of sinusoid; square, rectangle; triangle (symmetric or asymmetric); trapezoid; sawtooth; ramp (e.g., a linear ramp); exponential curve; piece-wise step function; and combinations of one or more of these. Implantable device 200 can deliver a train or burst stimulation waveform with an inter-pulse gap less than inter-train period. The inter-pulse gap can be relatively constant, and/or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200 can deliver a train stimulation waveform with an inter-pulse gap between 1 μsec and 1 second. Implantable device 200 can deliver a burst stimulation waveform with an inter-train period between 1 μsec and 1 second. Implantable device 200 can deliver a burst stimulation waveform with an inter-burst period between 20 μsec and 24 hours. The inter-burst period can be relatively constant, and/or it can be varied, such as when implantable device 200 randomly varies the inter-burst period or varies the inter-burst period systematically. In some embodiments, inter-burst period is varied by the user, such as via a user using programmer 600. In these embodiments, user activation can be regulated with one or more safeguards or other limits such as those incorporated into patient-controlled analgesia devices. The inter-train period can be varied between 1 μsec and 24 hours. Implantable device 200 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant, and/or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of cosine; cosine-squared; sine; square; rectangle; triangle (symmetric or asymmetric); trapezoid: sawtooth; ramp (e.g., linear ramp); and combinations of one or more of these. Implantable device 200 can deliver a train and/or burst stimulation waveform with a train ramp duration or burst ramp duration between 1 μsec to 10 minutes. Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period. The amplitude of the signal contained in these quiescent periods can be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g., electrical energy comprising a low frequency signal) and burst stimulation; burst stimulation (e.g., burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more stimulation elements 260, such as two or more electrodes which deliver similar or dissimilar stimulation waveforms simultaneously and/or sequentially. Each of the stimulation waveforms can comprise one or more pulses comprising an entire phase or at least a portion of a phase at a super threshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters. The stimulation parameters can be varied to optimize (e.g., balance the benefits of) therapeutic benefit, system efficiency, stimulation efficiency, avoidance and/or reduction of paresthesia, and/or reduction of charge.

Apparatus 10 can comprise one or more memory storage components (e.g. of an implantable device 200, external device 500, and/or other component of apparatus 10) that can store instructions for performing one or more algorithms, algorithm 15 shown. Algorithm 15 can comprise one or more algorithms that are configured to analyze data (e.g., data produced by a sensor-based functional element of apparatus 10) and produce a result. Algorithm 15 can comprise an algorithm (e.g. one or more algorithms) that are configured to steer current delivered by one or more stimulation elements 260, such as is described in applicant's co-pending U.S. patent application Ser. No. 17/383,972, titled "Systems with Implanted Conduit Tracking", filed Jul. 23, 2021. Algorithm 15 can comprise one or more algorithms configured to analyze data input by a user of apparatus 10 (e.g., a patient and/or a clinician of the patient), such as data entered via a user interface 680, and determine a stimulation paradigm SP, where paradigm SP comprises a set of stimulation parameter settings (e.g., stimulation energy settings as described herein) used to provide a therapy and/or otherwise treat a patient.

Each implantable device 200 of the present inventive concepts can be configured to deliver stimulation energy to one, two, three, four, or more anatomical locations of a patient, such as via sets of one or more stimulation elements 260 (e.g., electrodes) positioned on one or more leads 265. The stimulation energy delivered by the elements 260 can comprise tonic stimulation (e.g. a stimulation paradigm comprising a repeating pattern of pulses that are defined by pulse width, rate, and amplitude, where at the specified rate a pulse is delivered comprising a specified pulse width and a specified amplitude) and/or more complex stimulation waveforms (e.g., as represented by stimulation paradigm SP of apparatus 10). A first set of stimulation elements 260 can be positioned (e.g. implanted) and deliver and/or receive electrical current to deliver therapy (e.g., treat pain) in a first anatomical location, while a second set of stimulation elements 260 can be positioned and deliver and/or receive electrical current to deliver therapy (e.g., treat pain) in a second anatomical location. The first and second anatomical locations can include overlapping portions (e.g., the same tissue is included in each location) or they can be completely different volumes of tissue. The stimulation energy delivered to the two locations can be delivered sequentially, and/or simultaneously. In some embodiments, three, four or more anatomical locations receive therapy from corresponding sets of stimulation elements 260.

In some embodiments, one or more sets of stimulation elements 260 are configured to provide "combination waveform therapy", where the stimulation waveform defined by stimulation paradigm SP and delivered by elements 260 comprises a combination of two or more waveforms. For example, a first waveform can be delivered to a first anatomical location in which pain is present, and a second waveform can be delivered to a second anatomical location. The first waveform can comprise stimulation energy delivered at a frequency up to 100 Hz (e.g., to treat pain). The second waveform can comprise stimulation energy delivered at a higher frequency than the first waveform, such as a frequency of 1 KHz or more (e.g., for sub-threshold stimulation).

In some embodiments, one or more sets of stimulation elements 260 are configured to provide "microburst waveform therapy", where the stimulation waveform defined by stimulation paradigm SP and delivered by elements 260 comprises delivery of stimulation energy that is repeatedly turned on and off, such as to provide a therapy based on the repeated enhancement of onset of stimulation energy delivery (e.g., versus continuous stimulation energy delivery).

In some embodiments, one or more stimulation elements 260 are configured to provide "paired stimulation therapy", wherein the stimulation waveform defined by stimulation paradigm SP and delivered by elements 260 comprises at least two different types of waveforms that are delivered simultaneously, such as when the stimulation waveform comprises two or more of: a tonic stimulation waveform; a microburst stimulation waveform; and/or a waveform comprising a combination of pulses, trains, and/or bursts.

Each implantable device 200 can be configured to perform charge recovery in an "active" and/or a "passive" manner. For example, device 200 can perform active recovery by including a pulse of opposite polarity to the stimulating pulse(s) such that the net charge at the stimulation element 260 is zero (e.g., stimulating charge=recovery charge). Device 200 can perform passive charge recovery by electrically connecting the stimulation elements 260 for a period of time after delivery of stimulation energy to allow charge to dissipate (e.g., to allow the charge on included blocking capacitors to dissipate), thereby resulting in net zero charge at the stimulation elements 260. In some embodiments, implantable device 200 can perform charge recovery as described in applicant's co-pending U.S. patent application Ser. No. 17/384,020, titled "Stimulation Apparatus", filed Jul. 23, 2021. Configuration of active and/or passive charge recovery can be defined by stimulation paradigm SP.

In some embodiments, apparatus 10 (e.g., algorithm 15) is configured to apply a "pulse width constraint" when assessing the compatibility of a set of stimulation parameters, and/or when determining an acceptable range of values for a stimulation parameter to be used with a set of other stimulation parameters. For example, when a delivered stimulation includes delivery of stimulation at a relatively high rate (e.g., above 1 kHz, such as approximately 1.5 kHz), there may be parameter limitations applied due to the shorter pulse widths of stimulation pulses. Implantable device 200 can include a "minimum switching time" to account for in determining stimulation parameter setting compatibility, such as a switching time of approximately 180 μsecs. In some embodiments, apparatus 10 is configured to deliver the pulses for each area before a subsequent stimulation cycle begins. For example, the minimum amount of time available to deliver all the pulses is determined by the highest programmed stimulation rate (i.e. the waveform including the shortest interval), while considering any associated other requirements, "overhead" herein, such as the switching time requirements (e.g., switching requirements of the current sources, such as a time requirement of approximately 180 μsecs). In other words, the minimum stimulation interval is determined (e.g. via algorithm 15) to be at least the time of the sum of all the pulse widths plus the overhead. In some embodiments, the stimulation delivered includes a high-rate stimulation waveform of 1.5 kHz, and algorithm 15 limits passive recovery pulse width to a maximum of 110 μsecs, and active recovery pulse width to a maximum of 55 μsecs.

In some embodiments, apparatus 10 (e.g., algorithm 15) is configured to apply an envelope for stimulation based on: dosage on and dosage off times (DON and DOFF times, respectively, each as described herein). Apparatus 10 can provide up to two dosing periods, which can be associated with the rate of stimulation. In some embodiments, apparatus 10 constrains DON and/or DOFF. DON can be limited to a maximum time period, such as a maximum time period of 1 second. DOFF can be limited to a maximum time period, such as a maximum time period of 2 seconds, such as when the dosage period (DON plus DOFF) is limited to a time period of 2 seconds. Apparatus 10 can be configured to deliver stimulation energy at multiple rates, where a first rate (e.g., a relatively high rate) is delivered at a prescribed rate (e.g., a rate entered via user interface 680), while a second rate (e.g., a relatively low rate or otherwise lower than the first rate) is generated using a "N of M scheme" where a subset N of M pulses of the higher rate are delivered to effectively achieve the lower rate, such as is described herein in applicant's co-pending International PCT Patent Application Serial Number PCT/US2021/047815, titled "Apparatus for Delivering Customized Stimulation Waveforms", filed Aug. 26, 2021.

External device 500 can include one or more sensors, sensor 595 shown. In some embodiments, sensor 595 comprises a sensor-based functional element **599*a* as described herein. In some embodiments, sensor 595 comprises a sensor configured as a control to detect user input, such as is described in reference to FIGS. 2**A-B herein.

In some embodiments, external device 500 is configured to enter a sleep mode, such as a sleep mode which is initiated prior to storage (e.g., after manufacturing) and/or is otherwise temporary (e.g., where device 500 is to be turned on at a future time). In sleep mode, device 500 can be configured to draw no or minimal current (e.g., from its power supply 570), such as to avoid a complete or at least deep discharge of power supply 570. In some embodiments, power supply 570 comprises a Li-on battery, and complete discharge should be avoided. In some embodiments, device 500 is configured to transition out of sleep mode (e.g., turn on) and/or transition into sleep mode, based on one or more actions taken by a user, as described herebelow.

In some embodiments, external device 500 includes one or more functional elements **599*a* configured as charging pins (e.g., electrical contacts), such that charger 61 can electrically connect with the charging pins to deliver charging energy to power supply 570. In some embodiments, external device 500 can include at least one pin (e.g., an additional pin) that is used to cause device 500 to transition into and/or out of sleep mode (e.g., either directly or by interfacing with a push-button controller type device). Alternatively or additionally, device 500 can be configured to transition into and/or out of sleep mode based on charger 61 being placed in proximity to device 500, and/or removed from a location proximate device 500 (e.g., when power supply 570 is configured to receive energy wirelessly from charger 61 and device 500 does not include charging pins). Charger 61 can be configured to generate a signal (e.g., a signal sent through a charging pin of device 500 and/or sent wirelessly to device 500) that is used by external device 500 to enable and/or disable a switch (e.g., a load switch) and/or a regulator (e.g., that powers device 500), such as to turn on device 500 and/or cause device 500 to enter a sleep mode. Alternatively or additionally, device 500 can include a magnetic switch and/or an optical sensor (e.g., photo diode) that is used to cause device 500 to initiate a startup procedure or enter a sleep mode. For example, charger 61 and/or a user device (e.g., a cell phone or other tool 60** of the patient or other user) could be used to activate the magnetic sensor and/or optical sensor.

Figure 13:
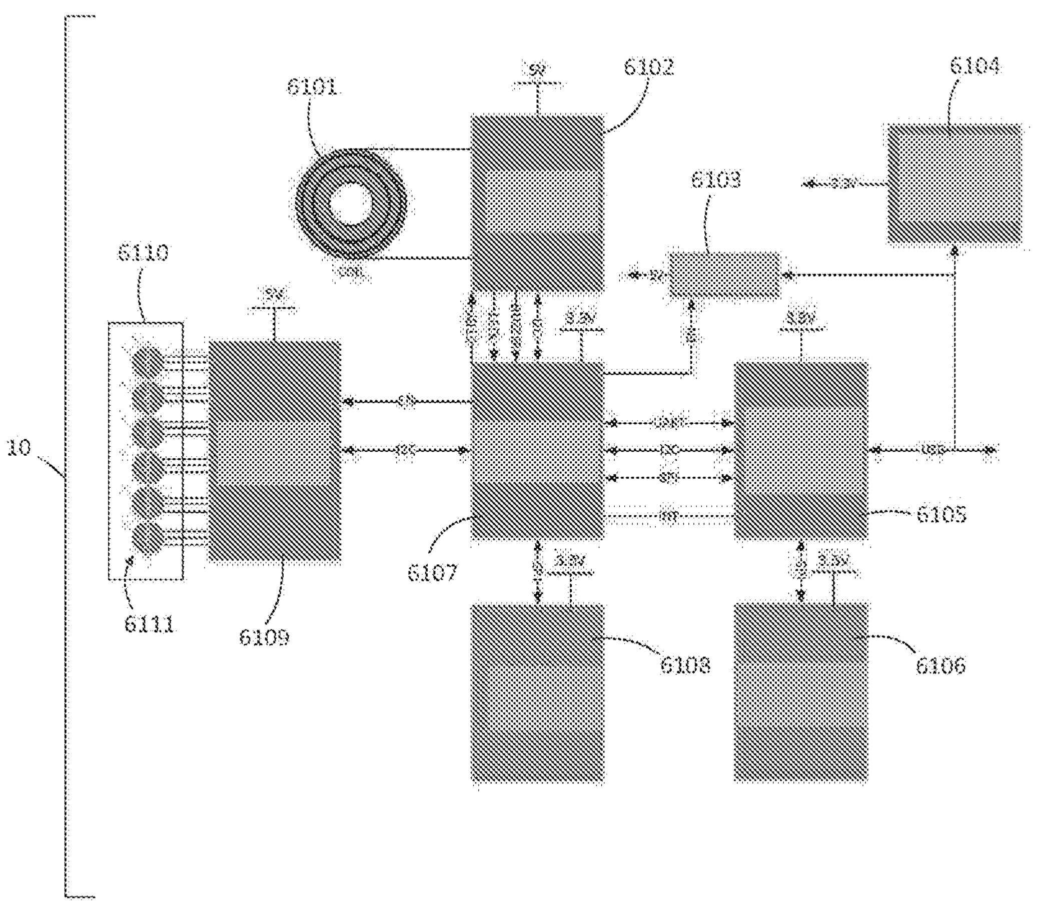
FIG. 13 illustrates a schematic view of a charger, consistent with the present inventive concepts.
Figure 13A:
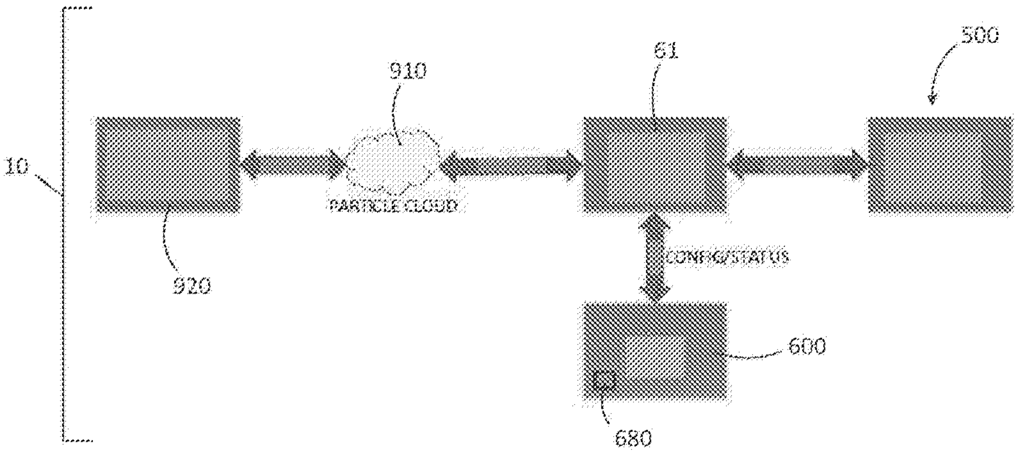
FIGS. 13A and 13B illustrate schematic views of a system including a charger configured to transmit information over a network consistent with the present inventive concepts.
Figure 13B:
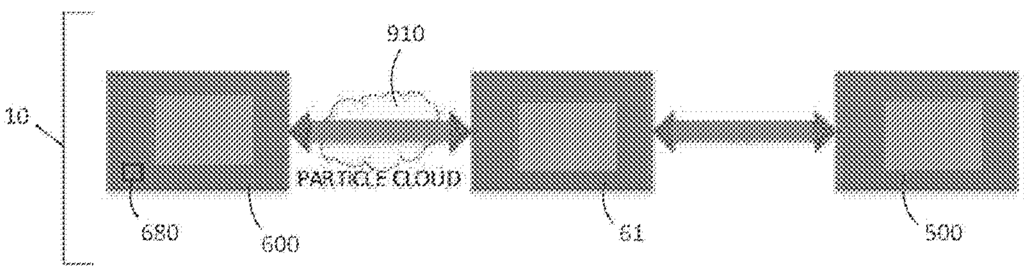

In some embodiments, apparatus 10 is configured to allow a user that is at a location remote from the patient to program an apparatus 10 component that is at the patient location (e.g., the patient's home or current location), such as is described in reference to FIGS. 13, 13A, and 13B herein. For example, an initiation and/or other modification of a stimulation paradigm SP or other system parameter modification can be performed by a representative of the manufacturer of apparatus 10 and/or a health care provider of the patient, where the modification step is performed at a location remote from the patient (e.g., at the manufacturer and/or at a clinical site). In some embodiments, tool 60 (e.g., a cell phone, tablet, and/or computer) is configured to be positioned at a remote location and to transmit and/or receive data (e.g., via the Internet, Wi-Fi, and/or cellular signals, as described in reference to FIGS. 13, 13A, and 13B and otherwise herein) to and/or from an apparatus 10 component at the patient location (e.g., to program that component and/or another apparatus 10 component at the patient location). In some embodiments, data is transferred between the remote location and an external device 500 at the patient location, such as via a communication pathway that includes a wireless communication link at the patient location (e.g., Bluetooth communication between external device 500 and another apparatus 10 component at the patient location). In some embodiments, data is transferred from the remote location and a programmer 600 (e.g., patient programmer 600') that is located at the patient location, such as via a secure link such as is provided in Samsung Knox software. In these remote programming scenarios, the patient may only need to turn on external device 500, and subsequently a user remote from the patient could program the device 500 without further patient input being necessary for operation.

As described herein, apparatus 10 can comprise two or more external devices 500, such as a first device 500*a* (e.g., similar to device 500 shown in FIG. 1) and a second device 500*b* (e.g., similar to device 500' shown in FIG. 1). There may be instances where first external device 500*a* has information (e.g., stimulation parameter settings and/or other information stored in memory of controller 550 of first device 500*a*) that is not also included in second external device 500*b* (e.g., not included in memory of controller 550 of second device 500'). Further in these instances, there may be a time in which the patient has traveled to a location (e.g., a hospital or other clinic) and has brought second device 500*b* but not first device 500*a*, such that the information of device 500*a* that is not stored on second device 500*b* is not available at this location. To avoid this unavailability of information, apparatus 10 can be configured to allow copying or other transfer of information between two or more external devices 500 (e.g., between first device 500*a* and second device 500*b*).

In some embodiments, a programmer 600 (e.g., patient programmer 600' and/or clinician programmer 600") is configured to cause information stored in one or more devices 500 to be transferred to one or more other devices 500, such as via a "synchronization routine" that is facilitated by programmer 600 (e.g., using algorithm 15). For example, programmer 600 can upload information from a first device 500*a* (e.g., all or a portion of the information stored on the device 500*a* uploaded into memory of device 600) and upload similar types of information from a second device 500*b* (e.g., into a different portion of memory of device 600). If the information on the two devices 500 is different, a synchronization routine can be performed, such as a synchronization routine in which a user (e.g., the patient, their clinician, or other user) is asked to confirm which sets of information (e.g., stimulation parameter settings) are to be synchronized (e.g., which are to be stored on both devices, which are to be used as stimulation parameter settings for the next or a future stimulation session, which are to be overwritten and potentially erased, and the like). In some embodiments, one or more stimulation programs (e.g., one or more sets of stimulation parameter settings) and/or firmware (e.g., firmware for one or more external devices 500) stored in a programmer 600 (e.g., sent to a programmer 600), and this information downloaded to one or more external devices 500.

Information transferred from one external device 500 to one or more other external devices 500 in a synchronization routine can include but is not limited to: stimulation parameter settings or other stimulation program information; other apparatus 10 settings; apparatus 10 use information (e.g., history); and/or patient use information.

Apparatus 10 can be configured such that a user can manually check the status of data, such as to be provided an assessment of current synchronization between two or more device 500 (e.g., a quantitative, qualitative, and/or other assessment provided via user interface 680 of device 600). Apparatus 10 can be configured such that a user can cause (e.g., manually cause) a synchronization routine to be performed, such as between two or more external devices 500 as selected by the user. Apparatus 10 can be configured to allow a user to cause particular information to overwrite other particular information (e.g., to cause one set of information to become "current" and the other information to be archived). For example, the synchronization can be configured to: overwrite certain information based on date of the information, such as to overwrite old data with new data, or even overwrite new data with old data; overwrite certain information based on location of the information, such as when data on device 500*a* overwrites data on device 500*b*, or vice versa; or other user-determined customization of an information overwrite and/or other information storage methodology.

In some embodiments, when old data is to overwrite new data (e.g., as initiated manually by a user or automatically by apparatus 10), apparatus 10 is configured to initiate a "confirmation routine" (e.g., a routine including delivering a sound or other alert, and enter a warning state as determined by algorithm 15), such as a confirmation routine which requires user confirmation of the overwriting of the newer data.

Figure 2A:
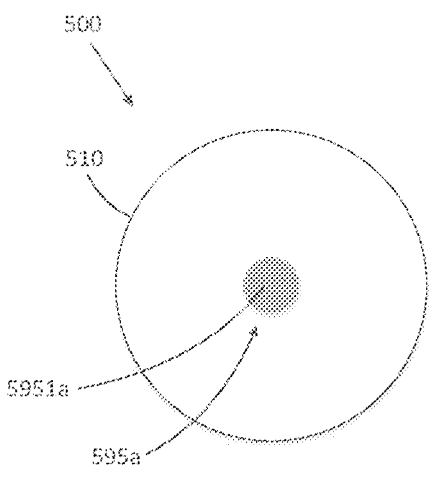
FIGS. 2A and 2B illustrate top views of an external device, consistent with the present inventive concepts.
Figure 2B:
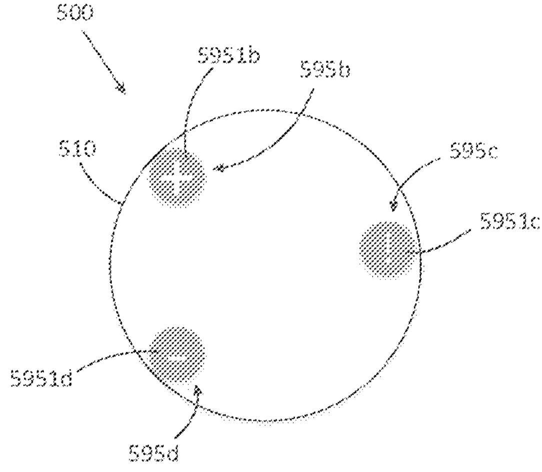

A programmer 600 and/or an external device 500 can include a button, icon, and/or other control (e.g., a sensor-activated control as described in reference to FIGS. 2A-B herein and/or other control of user interface 680 and/or 580 respectively), that is configured to allow a user to enter one or more synchronization routine and/or confirmation routine commands, such as a command causing: initiation and/or cessation of a synchronization routine; selection and/or deselection of data to be transferred between devices 500, overwritten in a device 500, and/or archived in a device 500; confirmation of an overwrite step; and combinations of these. In some embodiments, an icon or other control of user interface 680 and/or 580 that is used in a synchronization routine is only "present" (e.g., made visible or otherwise available to a user) when two devices 500 are in relative proximity to each other (e.g., and in proximity to a programmer 600 such that information can be wirelessly transmitted between the devices).

Apparatus 10 can be configured to copy (e.g., archive) any stimulation program or other stimulation parameter setting prior to overwriting those settings. In these embodiments, apparatus 10 can include a "restore routine" in which data that has been overwritten (e.g., in a synchronization routine) can be restored to previous values (e.g., data that has been archived is copied into its previous memory location).

Apparatus 10 can include a synchronization routine which is configured to avoid data corruption or omission errors when transferring data between two or more devices 500. For example, algorithm 15 can be configured such that if an error is detected during a synchronization routine, data (e.g., in each associated device 500) is restored (e.g., via a restore routine) to the state it was in prior to the initiation of the synchronization routine in which errors were detected. In some embodiments, a restore routine is configured to restore information to a state prior to two or more previous synchronizations.

In some embodiments, firmware (e.g., of controller 550) of a first device 500*a* is different than firmware of a second device 500*b*. In these embodiments, a synchronization routine of algorithm 15 may be configured to confirm the firmware differences do not create a compatibility issue, such as when algorithm 15, when a compatibility issue is detected, performs one or more of the following: causes apparatus 10 to enter an alert state (e.g., provide a visual, audible, and/or haptic alert); and/or prevents synchronization of one or more sets of data between the devices 500.

In some embodiments, apparatus 10 comprises a "cloning routine" that is configured to transfer appropriate information from a first external device 500*a* that has been used by the patient in one or more therapy sessions, to a second device 500*b* that has not yet been used with the patient (e.g., device 500*b* is a new device). The cloning routine can be configured to transfer program data (e.g., stimulation parameter settings), patient data, and/or other information stored on device 500*a* to memory of device 500*b*. In some embodiments, the cloning routine is configured to confirm that the second device 500*b* is within physical range (e.g., of programmer 600 and/or first device 500*a*), and/or confirm that the device is actually new (e.g., in a "factory shipped condition") prior to performing the cloning routine (e.g., prior to providing a control to allow a user to initiate the cloning routine).

Referring now to FIGS. 2A-B, top views of an external device 500 of the present inventive concepts is illustrated, consistent with the present inventive concepts. External device 500 can comprise one or more sensors, such as sensor 595*a* shown in FIG. 2A, and sensors 595*b, c, d* shown in FIG. 2B. Each sensor 595 can comprise one or more sensors as described in reference to FIG. 1 herein. In some embodiments, sensor 595 comprises one or more sensors configured to detect a tap, touch, or other intentional temporary contact of a user's finger or other body part with an exterior surface of housing 510 or another surface portion of external device 500. Each sensor 595 can comprise a portion that is positioned through a hole in housing 510 (e.g., exposed to a user's touch), and/or positioned within housing 510 (e.g., covered, but positioned proximate a portion of housing 510 to sense a user's touch to the housing 510 portion). In these embodiments, the exterior surface of external device 500 can be void of switches, buttons, and other movement-activated controls (e.g., controls that include at least a portion that must be moved by an operator for the control to sense an input from the operator. Absence of these movement-activated controls can provide numerous advantages, such as reduced cost of external device 500, resistance to fluid ingress (e.g., due to the lack of buttons, switches, and other movement-activated controls), and/or improved reliability of external device 500 (e.g., due to less moving parts). In some embodiments, external device is configured to detect a tap or other touch ("tap" herein) upon any exterior surface portion of external device 500 (e.g., any part of housing 510) as applied by the patient or other user of apparatus 10. In other embodiments, a particular exterior surface portion of external device 500 (e.g., a portion proximate a sensor 595) can be configured to detect a tap from a user. In these embodiments, external device 500 can include a decal or other marker, marker 5951 shown, which can be positioned on an exterior surface and proximate an associated sensor 595. In some embodiments, marker 5951 (e.g. one or more of markers 5951*a, b, c, d* shown) comprises a surface feature (e.g., a projection, a recess, a smoother surface than adjoining surfaces, a rougher surface than adjoining surfaces, and/or other surface feature) that can be identified via touch (e.g., finger touch) by the user, such as to identify the location of sensor 595 via touch (e.g., to identify one or more particular locations to be tapped or otherwise contacted by an operator to change a system setting or system state, as described herein). In some embodiments, marker 5951 comprises a surface feature that has a geometry recognizable by touch, such as a plus sign, a minus sign, a letter, a number, and/or a symbol.

In some embodiments, sensor 595 comprises an accelerometer, pressure sensor, mechanical switch, strain gauge, optical sensor, and/or other sensor configured to detect a tap applied to external device 500 by a user. In some embodiments, sensor 595 comprises a resistivity sensor positioned on housing 510 and configured to detect a user tap (e.g., a touch) applied to the sensor 595 (e.g., an exposed sensor 595 positioned on housing 510 configured to detect a reduction in resistance due to presence of tissue of a user's finger). In some embodiments, sensor 595 comprises a temperature sensor configured to detect a user tap of sensor 595 and/or a portion of housing 510 proximate the sensor 595 (e.g., due to a temperature change due to a finger touch). In some embodiments, sensor 595 comprises an optical sensor configured to detect a user tap of the sensor 595 (e.g., due to a blockage of light emitted by sensor 595 due to a finger touch, such as when sensor 595 detects reflections of the emitted light from a finger positioned over sensor 595).

External device 500 can be configured to use one or more taps and/or touches ("taps" herein) from a user, as detected by one or more sensors 595, as a form of user input (e.g., when user interface 580 comprises one or more sensors 595). The number of taps applied (e.g., within a time window) can correlate to a particular command. External device 500 can be configured to associate various arrangements of number of taps with particular system settings to be controlled (e.g., to set or modify stimulation parameter settings such as amplitude and other stimulation parameter settings). In one example, a single tap, or known combination of multiple taps, can cause a decrease in stimulation waveform amplitude, two taps can cause an increase in stimulation waveform amplitude, and five taps can cause external device 500 (and/or other component of apparatus 10) to turn on and/or off. In another example, a single tap, or known combination of taps, can cause one or more components of apparatus 10 (e.g., external device 500) to enter a lower-power state, such as a low-power state in which additional taps are detectable, but some or all other functions are disabled. In some embodiments, a low-power state comprises a device (e.g., external device 500) providing power of wireless communication (e.g., Bluetooth), while one or more other functions are disabled.

In some embodiments, external device 500 is configured to differentiate a tap applied to one exterior surface location of device 500 (e.g., a first location of housing 510) from a tap applied to another surface location of device 500 (e.g., a second location of housing 510). For example, external device 500 can include multiple sensors 595 (e.g., sensors 595*b, c, d* shown in FIG. 2B) that can be positioned proximate two, three, or more device 500 locations that are configured to differentiate taps applied to each of these locations. In some embodiments, a first tap location is on one side of device 500 and a second tap location is on the opposite side of device 500. In some embodiments, one or more taps at a first location is configured to initiate (e.g., allow) a user input correlating to a change to a stimulation parameter, while one or more taps at a second location are configured to record the user input defining the change to the stimulation parameter (e.g., such as to minimize the risk of undesired changes due to inadvertent taps to the second location).

Device 500 and/or another component of apparatus 10 can be configured to provide confirmation and/or other feedback of a successful tap delivered by the patient or other user (e.g., confirm a tap has been detected by a sensor 595), such as by activating a transducer-based functional element 599 (e.g., an LED or other light, a buzzer or other audio transducer, and/or other haptic transducer).

Figure 3A:
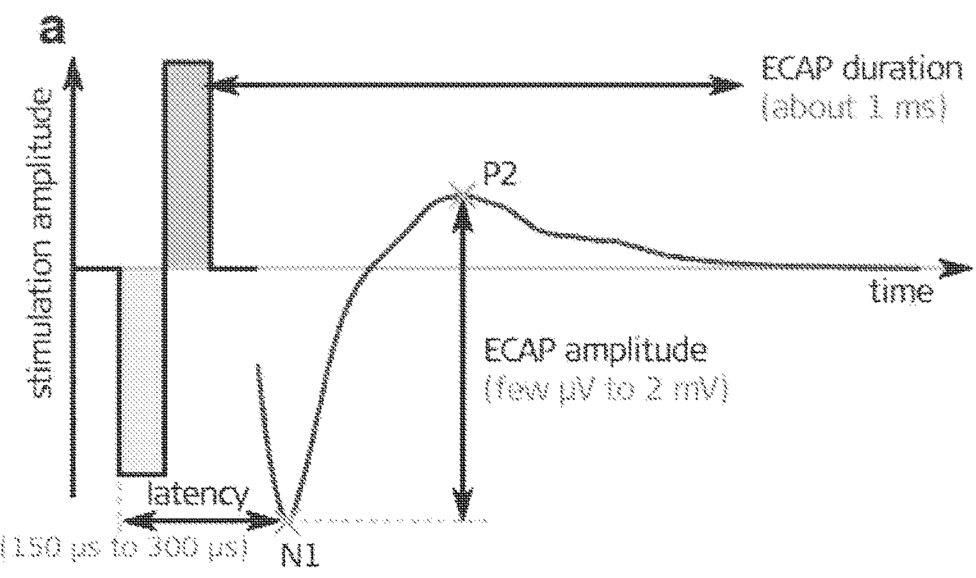
FIG. 3A illustrates a stimulation waveform and an electrically evoked compound action potential (eCAP), consistent with the present inventive concepts.

Referring now to FIG. 3A, a stimulation waveform of an electrically evoked compound action potential is illustrated. In some embodiments, apparatus 10 is configured to operate based on the measurement of one or more electrically evoked compound action potentials (eCAPs), such as is described in applicant's co-pending International PCT Patent Application Serial Number PCT/US2021/058673, titled "Apparatus for Delivering Enhanced Stimulation Waveforms", filed Nov. 9, 2021. An eCAP represents the synchronous firing of a population of electrically stimulated nerve fibers (e.g., as described in https://biomedical-engineering-online.biomedcentral.com/articles/10.1186/s12938-018-0588-z/figures/1). The stimulation waveform shown in FIG. 3A comprises a biphasic waveform (e.g., as provided by apparatus 10, where the stimulation energy is delivered by one or more stimulation elements 260 of an implantable device 200). In some embodiments, a monophasic waveform can be provided (e.g., as provided by apparatus 10, which can include passive charge recovery and/or accompanied by a delayed charge recovery).

Figure 3B:
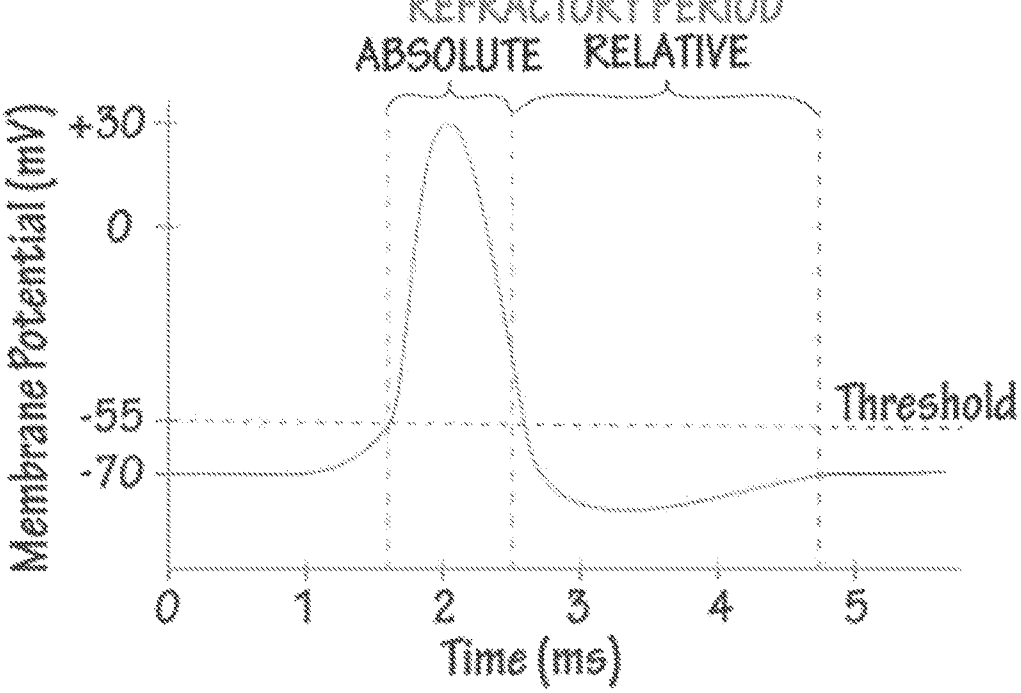
FIG. 3B illustrates a naturally occurring action potential, consistent with the present inventive concepts.

The resultant eCAP is a biphasic signal characterized by a negative peak, N1, and a positive peak P2. The magnitude of the absolute difference between N1 and P2 is referred to as the eCAP amplitude. The P1 peak of the eCAP (e.g., as shown in FIG. 3B) occurs during the stimulation pulse, and it is obscured by a stimulus artifact.

Due to the large stimulus artifact, the eCAP is usually measured by a recording element (e.g., an electrode) that is a different component than the component delivering the stimulation pulse (e.g., a stimulation element 260). The latency of the N1 peak relative to the stimulus is an indication of the distance between the recording component and one or both of: the stimulation pulse-delivering elements (e.g. elements 260) and one or more neural structures in the vicinity of the stimulation pulse-delivering delivery elements 260.

Figures 3C, 3D:
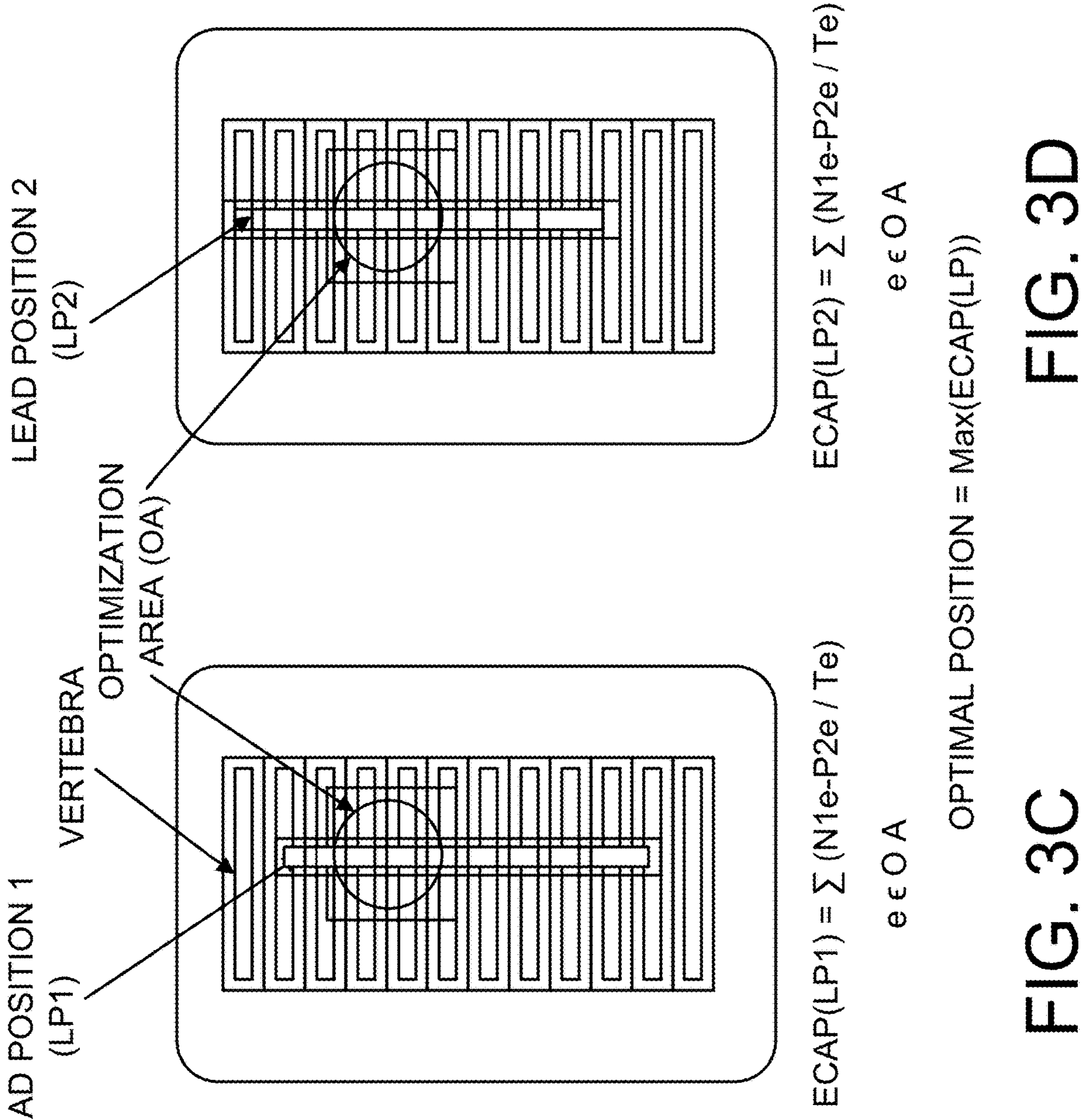
FIGS. 3C-3D illustrate top views of an implanted lead, consistent with the present inventive concepts.

Referring now to FIGS. 3C-3D, two anatomical schematic views of an implanted lead are illustrated, consistent with the present inventive concepts. In some embodiments, apparatus 10 is configured to measure one or more eCAPs, such that apparatus 10 and/or an implanting clinician can use the measured eCAP data in the placement of lead 265 at an implant location, such as to optimize the placement of one or more stimulation elements 260 positioned on the lead 265. For example, apparatus 10 can use eCAP measurements to determine the distance between one or more stimulation elements 260 and a desired neural target to be stimulated (e.g., to optimize treatment of pain). In some embodiments, multiple measurements (e.g., multiple relatively continuous measurements) of eCAPs are performed via one or more stimulation elements 260. During lead 265 placement (e.g., advancement, retraction, and/or other movement of lead 265), measured eCAPs can be displayed to the implanting clinician (e.g., via user interface 680" and/or 580) as a function of time and/or lead 265 location. Alternatively or additionally, other forms of feedback can be provided, such as audible and/or haptic feedback, as described herein. In some embodiments, an operator (e.g., the implanting clinician) provides information to apparatus 10 regarding an anatomical location (e.g., a starting location and/or a present location) of one or more stimulation elements 260 or other portion of lead 265. For example, for spinal cord placement and stimulation, the clinician may enter location information regarding the position of a particular element 260 (e.g., the distal-most element 260 on lead 265) relative to an anatomical location (e.g., an anatomical landmark such as vertebral level in spinal cord placement).

In some embodiments, apparatus 10 and algorithm 15 can be configured to optimize lead 265 placement and/or determine a stimulation paradigm SP (e.g., selection of stimulation elements 260 to deliver energy and/or the stimulation energy parameters for these elements 260) based on the equations shown in FIGS. 3C-3D.

In some embodiments, during an implantation procedure (e.g., in an operating room or other clinical setting) an implanting clinician places lead 265 in a first, "initial" anatomical location (e.g., LP1 shown in FIG. 3C) and then uses apparatus 10 to make one or more eCAP measurements while making small changes in the location of lead 265 (e.g., via advancement, retraction, and/or rotation to LP2 shown in FIG. 3D). Algorithm 15 of apparatus 10 can use various criteria for analyzing the eCAP measurements in a stimulation area of interest (e.g., optimization area OA shown in FIGS. 3C-3D) to optimize lead 265 placement (e.g., optimize placement of the stimulation elements 260 by an implanting clinician). For example, a location can be selected that provides a low (e.g., lowest) amplitude stimulation while achieving a high (e.g., highest) eCAP response. This technique can be used for multiple elements 260, such as when algorithm 15 identifies a location for lead 265 based on the best average eCAP response over multiple elements 260 (e.g., all elements 260 of lead 265 and/or at least all elements 260 of lead 265 selected to deliver stimulation energy). In some embodiments, a user (e.g., the implanting clinician) provides one or more proposed final locations for lead 265, and algorithm 15 uses one of the eCAP-based optimization techniques to select a final location based on the one or more potential final locations. For example, algorithm 15 can be configured to determine an eCAP response at a lead position "x" per the following equation:

$$eCAP(LPx) = \text{Sum}\left((N1_e - P2_e)/T_e\right) \text{ for all } e$$

where e is an index for each eCAP recording configuration (e.g., each combination of two or more electrodes 260) in the optimization area OA.

The optimal position of leads 265 is determined by:

$$\text{Optimal Position} = \text{Max}(eCAP(LP[1:N]))$$

where N represents the total number of lead positions LP in which lead 265 has been located during the eCAP recordings, and LP[1:N] represents the full set of lead positions LP.

In some embodiments, a proposed final location for lead 265 can be determined (e.g., by a clinician and/or automatically by apparatus 10), and algorithm 15 can be configured to identify which stimulation elements 260 should be delivering stimulation energy based on the proposed final location. In some embodiments, algorithm 15 is configured to determine a final location for lead 265 based on both eCAP measurements as well as patient anatomical image information (e.g., as provided by CT, X-ray, fluoroscope, ultrasound imager, MRI, and/or other imaging device). Similarly, when the leads are moved (up or down) to "search" for the optimal lead 265 location, an operator can input to apparatus 10 which stimulation elements 260 correspond to (e.g., should be selected for) the optimization area OA, and/or apparatus 10 can determine those elements 260 automatically.

Figure 4:
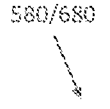
FIG. 4 illustrates an operator's view of a user interface of a stimulation apparatus, consistent with the present inventive concepts.
Figure 4:
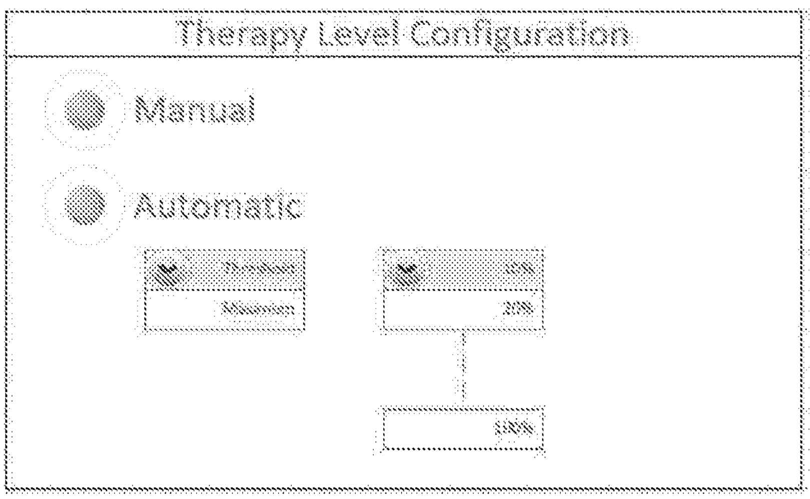

Referring now to FIG. 4, a user interface of stimulation apparatus is illustrated, consistent with the present inventive concepts. The user interface of FIG. 4 can comprise user interface 580 of an external device 500 and/or user interface 680 of a programmer 600 (e.g., patient programmer 600' and/or clinician programmer 600"). User interface 580/680 of FIG. 4 is depicting a configuration of apparatus 10 in which programming (e.g., setting of one or more stimulation parameters) can be configured in a manual mode and/or an automatic mode, as selected via a control (e.g., a touch-screen control) of user interface 580/680 that causes apparatus 10 to transition between the two modes. In some embodiments, when in the automatic mode apparatus 10 is configured to automatically select a stimulation paradigm SP (e.g., a set of one or more stimulation parameter settings determined by algorithm 15) based on a clinician or other operator-performed measurement that measures one or more parameters (e.g., one or more stimulation thresholds, and/or one or more maximum setting parameters, such as a maximum setting that is set based on an acceptable level of paresthesia). In some embodiments, apparatus 10 is configured to deliver a stimulation paradigm SP comprising a stimulation waveform as described in applicant's co-pending U.S. patent application Ser. No. 17/372,095, titled "Apparatus with Enhanced Stimulation Waveforms", filed Jul. 9, 2021. A stimulation paradigm SP stimulation setting (e.g., a stimulation parameter setting for a customized stimulation waveform and/or high-rate tonic stimulation) can be based on a measured threshold (e.g., a first sensation of paresthesia by the patient). In some embodiments, a stimulation parameter setting is set to a percentage of the measured threshold, such as 70%, 50%, and/or 30% of the measured threshold, such as when the percentage of the threshold used is selected via user interface 580/680 as shown in FIG. 4. For low-rate tonic stimulation (e.g. a rate of no more than 100 Hz), the stimulation parameter setting can be set to a maximum level, also as selected via user interface 580/680. A user (e.g., a technician or clinician of the patient) can set a stimulation level, such as a stimulation parameter setting for multiple therapy programs (e.g., 6 programs each requiring two settings, one for each posture of the patient).

To reduce programming time, apparatus 10 can be configured to automatically provide one or more stimulation parameter settings. For example, user interface 580/680 can provide a therapy level configuration screen as shown in FIG. 4, including various icons as shown. If a "manual" icon is selected, manual setting of stimulation parameters can be performed. If an "automatic" icon is selected, stimulation parameter settings can be set based on either a threshold level (e.g., for sub-threshold stimulation) by selecting a "threshold" icon, or it can be set to a maximum level (e.g., for supra-threshold stimulation) by selected a "maximum" icon.

Apparatus 10 can be configured to allow selection by a user of threshold or maximum arrangements irrespective of whether the thresholds or maximums have been determined. For example, if a measurement required to set a stimulation level has not been performed, upon selection of an associated icon of user interface 580/680, user interface 580/680 can provide a message that additional action is required (e.g., additional information is required). Algorithm 15 can comprise various configuration "rules" to notify an operator if required information is not yet available at the time that the programming step is performed (e.g., an icon is selected). Apparatus 10 can be configured to allow this programming, and to automatically determine an associated stimulation parameter when the currently missing information becomes available (e.g., threshold and/or maximum level information). Additionally or alternatively, apparatus 10 can be configured to prevent delivery of stimulation energy until all such required information is made available.

In some embodiments, when switching from a manual mode to an automatic mode, apparatus 10 is configured to update one or more stimulation parameters if the associated information (e.g., threshold and/or maximum level information) is available. If the information is not available, apparatus 10 can be configured to leave one or more stimulation parameters unchanged. While operating in an automatic mode, if a configuration setting is changed between a maximum-based configuration and a threshold-based configuration, stimulation parameter settings can be changed accordingly, and/or left blank (setting not yet set) if currently blank. Configuration rules of apparatus 10 can be maintained when a user is performing a function related to copying, exporting, importing, uploading, and/or otherwise setting one or more stimulation parameters.

Figure 5A:
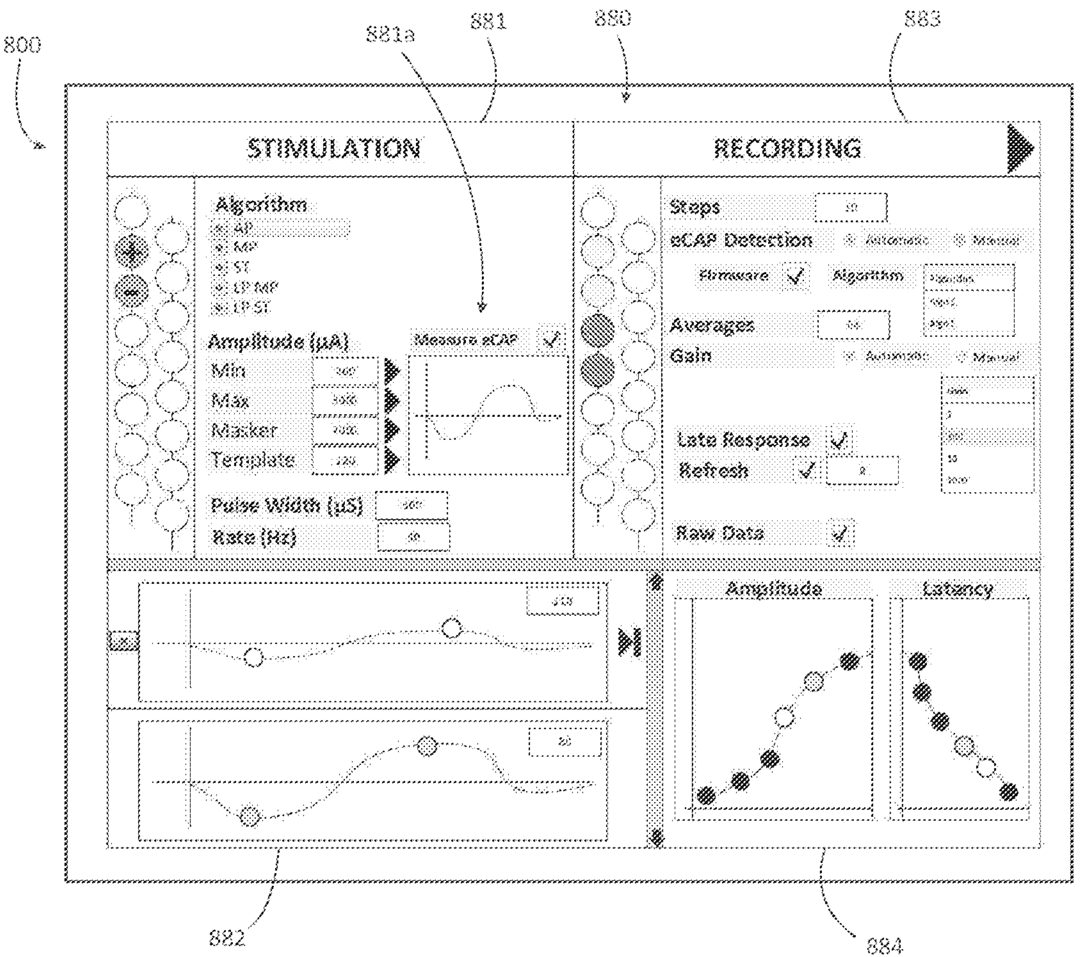
FIG. 5A illustrates a top view of a trialing interface of a stimulation system, consistent with the present inventive concepts.

Referring now to FIG. 5A, a top view of a trialing interface of a stimulation system is illustrated consistent with the present inventive concepts. Apparatus 10 can comprise one or more devices configured to operate (e.g., temporarily operate) one or more implantable devices 200, such as trialing interface 800 shown. In some embodiments, trialing interface 800 is of similar construction and arrangement as trialing interface 80 and/or 90 described herein in reference to FIG. 1. Trialing interface 800 can be configured to operate an implantable device 200 during a trialing procedure, also as described herein. In some embodiments, trialing interface 800 can be configured to include eCAP measurement circuits. In these embodiments, the trialing interface 800 can include firmware and/or other componentry that implements eCAP capture, artifact cancellation, and/or feature extraction of the captured waveform.

Trialing interface 800 can also be configured (e.g., include software that is configured) to allow measurement and display of stimulation optimization tests, such as "growth", "spatial", and the like. In some embodiments, a growth curve can represent a comparison of the amplitude of a delivered signal (e.g., delivered by a pair of stimulation elements 260) to the eCAP response. In some embodiments, a growth curve can represent a comparison of pulse width of a delivered signal to the eCAP response (e.g., with amplitude held constant). In some embodiments, a growth curve can represent a comparison of rate of a delivered signal to the eCAP response (e.g., with amplitude and pulse width held constant). As stimulation amplitude is increased, eventually a saturation occurs in which minimal additional neuron recruitment occurs. A spatial curve can be created by delivering stimulation energy on a first set of two or more electrodes (e.g., a first set of stimulation elements 260), and recording eCAP response on a different set of two or more electrodes (e.g., a different set of stimulation elements 260). In some embodiments, the first set of electrodes includes some or all of the same electrodes as the second set of electrodes. In other embodiments, all or at least one of the first set of electrodes is different than the electrodes of the second set of electrodes. The eCAP response can be measured on multiple pairs of electrodes (e.g., some or all of the electrodes on a lead 265), such as to identify an area of increased (e.g., maximized) neural response. Apparatus 10 can vary the electrodes used to measure the eCAP response (e.g., resulting in a spatial variation of recording locations), such as to provide an assessment of how stimulation present in one location affects neurons in other locations and/or propagates through other locations.

Trialing interface 800 can store one or more sets of eCAP recordings. In some embodiments, duplicating a session will carry forward only the user settings (not the recorded data). This duplication enables an operator to start a new session with similar recordings made in a previous session, such as for the same patient or a different patient, without having to enter all the necessary parameters prior to each session.

In some embodiments, trialing interface 800 includes one or more templates that can be used to configure different types of measurements (e.g., including operator-defined measurement sets), such as to determine growth curves versus spatial curves.

Trialing interface 800 can include user interface 880 shown in FIG. 5A. In some embodiments, user interface 880 is included in a programmer 600 (e.g., patient programmer 600' and/or clinician programmer 600" described herein) and/or other component of apparatus 10. Trialing interface 800 can be configured to upload data (e.g., stimulation paradigm SP data and/or other apparatus 10 configuration data) from one or more components of apparatus 10, such as a trialing interface 80 and/or 90, an external device 500, an implantable device 200, and/or a programmer 600. Trialing interface 800 can be configured to duplicate parameters of a therapy session (e.g., stimulation paradigm SP parameters used to provide pain relief or other therapy). Trialing interface 800 can be configured to perform (e.g., allow an operator to perform) one or more impedance measurements for stimulation elements of an implanted lead 265.

Apparatus 10 can be configured to perform various methods of artifact cancellation, such as via the "masker probe" MP method and/or the "scaled template" ST method described herebelow. Apparatus 10 can be configured to provide a "live playback" LPB mode of operation, also as described herebelow. User interface 880 can be configured (e.g., by an operator) in various layouts (e.g., arrangements of information and controls), such as the example layout shown in FIG. 5A. In FIG. 5A, user interface 880 comprises sections 881, 882, 883, and 884. Section 881 includes graphical components (e.g., icons and information display) that enable an operator to configure settings of stimulation energy to be delivered, and one or more algorithms (e.g., of algorithm 15) to be utilized by trialing interface 800. Stimulation amplitudes can be set based on patient comfort. Section 881 includes portion 881*a* that displays a real-time display of the measured eCAP. This measurement of portion 881*a* can be used by an operator to quickly determine if a stimulation pulse does or does not generate an eCAP. If apparatus 10 is providing an MP method of artifact cancellation, it is necessary to confirm that a substantial eCAP has been generated by the associated masker pulse. If apparatus 10 is providing an ST method of artifact cancellation, also as described herebelow, it is necessary to confirm that no eCAP is generated by the template pulse. Utilizing the simplified view provided by portion 881*a*, an operator can determine the amplitude of these pulses and enter them for use in subsequent measurements of growth or spatial curves. Section 882 includes graphical components that can display measured eCAP response (e.g., in real-time). Section 883 includes graphical components that enable an operator to configure eCAP recording parameters. Section 884 shows amplitude and latency of eCAP measurements.

Trialing interface 800 can be configured to perform artifact cancellation, and/or resolving of eCAPs (e.g., via averaging). An operator may have selected an algorithm (e.g., of algorithm 15) to detect a response (e.g., via the algorithms shown in section 881). Alternatively or additionally, trialing interface 800 can be configured in an automatic mode, such as an automatic mode in which a series of algorithms (e.g., one or more algorithms 15) are utilized (e.g., sequentially or in parallel). An algorithm 15 can mark the appropriate stimulation elements 260 (e.g., shown shaded), and/or an operator can manually mark the elements 260. In some embodiments, if an operator notices a response, the operator can cause (via an icon or other control of user interface 880) a next step to be performed (e.g., to save time).

In a particular example, an operator selects an algorithm 15 via section 881. A "masker pulse" can be entered for an MP mode and/or a mode comprising LPB (live playback) and MP, and a template can be entered for ST mode and/or a mode comprising LPB (live playback) and ST, each as described herebelow. The operator can test the intensity of the stimulation. For amplitude of a masker pulse, the operator will ensure that the stimulation generates a larger eCAP response.

In some embodiments, the maximum rate available for programming is governed by the recording duration where:

$$\text{maximum rate} = (1/\text{recording duration})$$

Depending on the amplitude and the pulse width, the maximum rate can be further limited by apparatus 10 to enhance stimulation safety (e.g., limited based on charge density, current density, and/or charge per phase).

In some embodiments, automatic eCAP detection can be selected, and apparatus 10 can be configured to allow an operator to execute the detection algorithm (e.g., an algorithm 15 comprising a detection algorithm) via the firmware and/or an application of apparatus 10 (e.g., firmware and/or an application of programmer 600). The detection algorithm can detect the presence of an eCAP and stop the performance of a subsequent step (e.g., a subsequent measurement). The numbers of averages required to achieve a positive eCAP response is therefore dynamic and determined by the algorithm 15. For example, at low signal-to-noise ratio (SNR), the detection algorithm may require a larger number of samples to converge and detect an eCAP response than that would be required with a higher SNR.

In some embodiments, manual eCAP detection can be selected, and apparatus 10 can be configured to allow the operator to pre-determine the number of measurements to average for a given eCAP measurement.

In some embodiments, apparatus 10 is configured such that a "late response" is included in the eCAP measurement (e.g., where an eCAP response generally occurs between a duration of 2 msec to 5 msec after the onset of the stimulus).

In some embodiments, apparatus 10 is configured to update a display (e.g., a graphical display) of the measured eCAP response as it is being measured. An operator can set the number of measurements before displaying an updated measurement. In some embodiments, an operator can specify the rate of updating to be provided, such as by specifying a number of updates to be provided per second. Apparatus 10 can be configured to operate in an automatic mode of eCAP detection (e.g., detection by an algorithm 15), and it can be further configured to allow an operator to manually identify presence of an eCAP (e.g., overriding the automatic detection). For example, this manual detection by the operator can be performed when the detection algorithm 15 is not fully optimized and/or sufficiently conservative, and manual detection by the operator can be performed more readily than via the algorithm 15. Apparatus 10 can be configured to allow an operator to advance to the next step (e.g., via an icon or other control of user interface 880).

Apparatus 10 can store the raw data of all recordings, such as the eCAP recordings (e.g., individual recordings, such as the anodic-leading, cathodic-leading, and signature measurements of the alternating polarity method described herebelow). Apparatus 10 can be configured to store the eCAP of each individual measurement (e.g., the A+B result of the alternating polarity method). Apparatus 10 can be configured to periodically store the averaged eCAP, such as a running average stored after a certain number of eCAP measurements. Apparatus 10 can be configured to store a final eCAP result.

Apparatus 10 can be configured such that the eCAP and latency that are displayed (e.g., on interface 800) are highlighted on displayed growth and/or latency curves.

Apparatus 10 can be configured to allow an operator to deselect a measurement from being used in a growth and/or latency curve (e.g., by activating a deselecting icon or other control of user interface 880).

Apparatus 10 can be configured such that user interface 880 provides the numbers of averages that were used for each curve displayed (e.g., such as when configured to automatic eCAP detection). In some embodiments, apparatus 10 (e.g., trialing interface 800) includes an algorithm (e.g., algorithm 15 described herein) that determines a confidence interval for the eCAP detection (e.g., a confidence interval that is displayed on user interface 880).

Figure 5B:
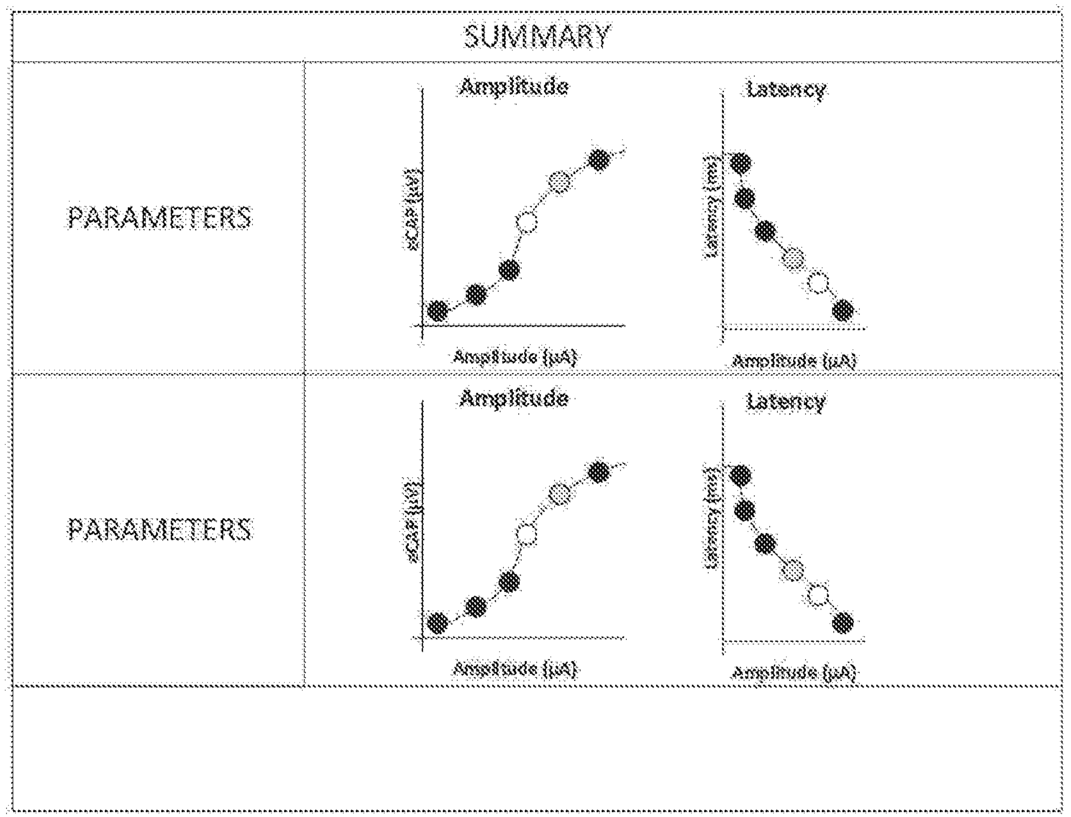
FIG. 5B illustrates a user's view of a summary tab of information of the trialing interface of FIG. 5A, consistent with the present inventive concepts.

In some embodiments, user interface 880 is configured to provide various tabs of information, such as multiple tabs that provide measurement information, as well as a summary tab (e.g., as shown in FIG. 5B) that allows an operator to view responses and parameters from each of the measurement tabs.

Apparatus 10 can be configured to perform one or more forms of artefact cancellation. Various stimulation and other parameters can be used in order to perform artefact cancellation. Apparatus 10 can provide various stimulation parameters and/or eCAP measurement parameters (e.g., operator and/or apparatus 10 provided parameters), that can be used by algorithm 15 in performing artefact cancellation, such as is described herebelow. These parameters include, but are not limited to: electrodes used to deliver stimulation energy; amplitude of energy delivery; pulse width of stimulation energy; electrodes used to record eCAPs; duration of recordings; signature enable (e.g., enablement of a "signature" measurement that can be used to cancel systemic drift and/or synchronous noise which is usually a recording with zero stimulation amplitude); and combinations of these. Apparatus 10 can provide various eCAP recording options, as well as various ways in which eCAP measurements can be provided to an operator and/or used by algorithm 15. Apparatus 10 can be configured to provide eCAP recording options (e.g., recording selection options) selected from the group consisting of: all raw traces; eCAP response raw traces; individual traces averaged; averaged eCAPs; features such as N1-P2 magnitude; N1 latency; a late response (e.g., a feature in the eCAP that occurs significantly after the stimulus is delivered); modes such as "one-shot" (e.g., a single, relatively continuous measurement and recording of eCAP performed until a memory threshold is reached, after which recording is stopped); "circular" (e.g., a single, relatively continuous measurement and recording of eCAP performed until a memory threshold is reached, after which recording is continued and memory overwritten in a cyclic arrangement); and/or "event" (e.g., an eCAP capture that is initiated by a sensor-activated and/or operator-activated trigger); and combinations of these. Event mode can comprise a capture that is triggered by patient posture (e.g., change or a particular posture); patient activity; and/or another patient parameter. Event mode can be triggered by a change to a system parameter (e.g., stimulation amplitude) made by an operator (e.g., the patient). At each event, apparatus 10 can enter a one-shot, circular, and/or other measure of eCAP, such as for a pre-determined duration. Apparatus 10 can be configured to measure and record eCAP until a second event occurs, at which time the measuring and recording can be stopped. In some embodiments, modes such as one-shot, circular, and/or event, are used (e.g., preferentially used) when the patient is at locations separate from their clinical site(s) and/or otherwise separate from a clinician.

Referring now to FIGS. 6A-6C, apparatus 10 (e.g., via algorithm 15) can be configured to perform an alternating polarity method of artefact cancellation, where responses (including artifact and eCAP) evoked by a cathodic leading pulse, trace shown in FIG. 6A, and the anodic-leading pulse, trace shown in FIG. 6B, are recorded. The polarity of the stimulus artifact in these two traces is reversed. In contrast, the polarity of the eCAP remains the same. Apparatus 10 can eliminate or at least reduce ("reduce" herein) the stimulus artifact and derive the eCAP by averaging the responses of both polarities, as shown in FIG. 6C.

Referring now to FIGS. 7A-7D, apparatus 10 (e.g., via algorithm 15) can be configured to perform a masker-probe (MP) method of artefact cancellation, which utilizes refractory properties of a nerve. Apparatus 10 can be configured to record responses in three stimulation conditions. In a first condition, a response evoked by delivery of a single biphasic pulse, referred to as the "probe pulse", is recorded, as shown in FIG. 7A. This response includes the stimulus artifact and the eCAP evoked by the probe pulse. In the second condition, two biphasic pulses are delivered sequentially, as shown in FIG. 7B, with a relatively short inter-pulse interval (e.g., an interval of 1 msec or less). The first pulse, referred to as the "masker pulse", is typically higher in stimulation level than the second pulse, a probe pulse. When the masker-probe-interval (MPI) is sufficiently short, such as a time period of less than 100 μsec, less than 500 μsec, and/or less than 1 msec, the response to the masker pulse is assumed to leave the nerve in a refractory state such that it is unable to generate a neural response to the probe. Therefore, the trace recorded in this condition includes artifacts evoked by the masker pulse and the probe pulse and the eCAP evoked by the masker pulse. In the third condition, only the masker pulse is delivered, as shown in FIG. 7C, and the recorded response includes the artifact and the eCAP evoked by the masker pulse. The eCAP elicited by the probe pulse can be derived by subtracting artifact evoked by the probe pulse from the response evoked by the probe pulse alone, as shown in FIG. 7D. Optionally a recording with no stimulus (called a "signature") can be made (before or after the two measurements) and subtracted from the final response to eliminate any systematic and/or correlated noise and/or drift. System parameters associated with the masker-probe method of FIGS. 7A-D include but are not limited to: masker electrodes used; amplitude of masker pulse; pulse width of masker pulse; and masker-probe-interval (MPI).

Figures 8A, 8B, 8C:
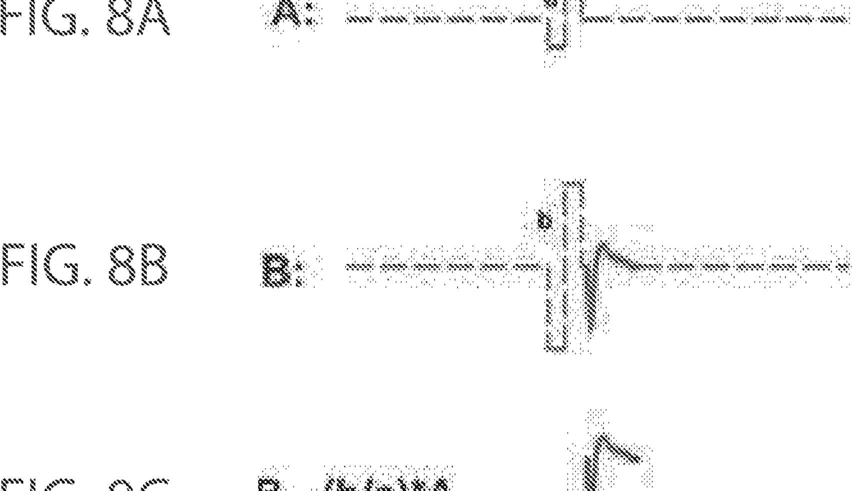
FIGS. 8A-8C illustrate a scaled template method of artefact cancellation, consistent with the present inventive concepts.

Referring now to FIGS. 8A-8C, apparatus 10 (e.g., via algorithm 15) can be configured to perform a scaled template (ST) method of artefact cancellation. Apparatus 10 can be configured to deliver and record a biphasic pulse that is below a neural threshold, as shown in FIG. 8A. This recording includes only stimulus artifact, which apparatus 10 uses as a template. Apparatus 10 can be further configured to deliver a supra-threshold biphasic pulse, and to record the resultant trace including both the stimulus artifact and the eCAP, as shown in FIG. 8B. Apparatus 10 can scale up the template of FIG. 8A to match the magnitude of the stimulus artifact of FIG. 8B, and then subtract the scaled template from the recording of FIG. 8B to produce the resultant trace of the eCAP with artifact removed, as shown in FIG. 8C. System parameters associated with the scaled template method of FIGS. 8A-8C include but are not limited to: amplitude of the template; and/or pulse width of the template.

Figure 9:
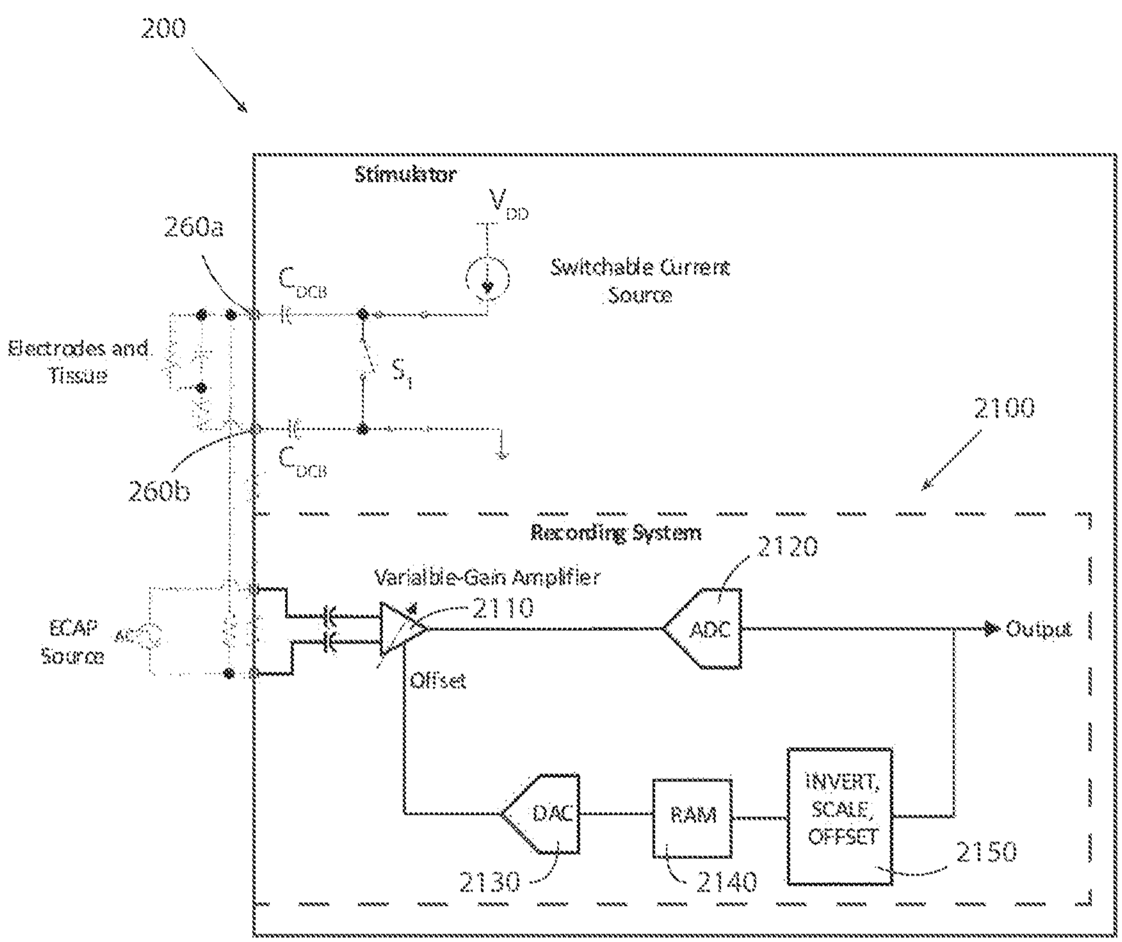
FIG. 9 is a schematic of a device configured to perform a live playback mode of operation, consistent with the present inventive concepts.

Referring now to FIG. 9, apparatus 10 can be configured to provide a "live playback" (LPB) mode of operation. For example, algorithm 15 can be configured to record eCAPs generated by monophasic pulses with passive recovery. Passive recovery introduces a "long tail" which swaps the evoked response. In some embodiments, apparatus 10 is configured to provide a LPB mode as described in applicant's co-pending U.S. patent application Ser. No. 17/384,020, titled "Stimulation Apparatus", filed Jul. 23, 2021. In the LPB mode, apparatus 10 first records the recovery artefact with a low-level stimulus (low enough that there is now eCAP response), and then inverts and plays back the scaled (to match the stimulus) and inverted artefact into an amplifier for the eCAP measurement. Alternatively, apparatus 10 can utilize a masker-probe (MP) method, as described hereabove, to record the artefact, where a biphasic masker pulse could be delivered such that the following monophasic probe pulse does not generate and eCAP and the artefact is recorded for later playback. In some embodiments, apparatus 10 is configured to combine LPB mode with AP and/or MP modes. In these embodiments, the underlying signals used in AP and/or MP mode are monophasic with passive charge recovery, which can enable use of various stimuli that may better correlate with the stimulation paradigm SP or other stimulation energy delivery being used therapeutically. A schematic of an implantable device 200 including a recording system 2100 is shown in FIG. 9. Implantable device 200 can be configured to perform an LPB mode of operation.

Implantable device 200 can be configured to implement monophasic stimulation, and it can comprise a switchable current source $V_{DD}$ and a shorting switch S1. Current source $V_{DD}$ and shorting switch S1 can connect to one, two, or more stimulation electrodes 260 through DC-blocking capacitors $C_{DCB}$. Current source $V_{DD}$ can be switched on during a stimulation phase and turned off while shorting switch S1 is closed during a charge recovery phase.

Recording system 2100 can comprise a variable-gain amplifier, amplifier 2110, and an analog-to-digital convertor, ADC 2120. Amplifier 2110 can be configured to provide gain for a combined eCAP/artifact signal, and its output can be digitized by ADC 2120. Recording system 2100 can further comprise a digital-to-analog-convertor, DAC 2130, a random-access memory, RAM 2140, and a computing element 2150 (e.g., hardware and/or software) configured to perform inversion, scaling, and/or offset arithmetic of the combined eCAP/artifact signal. The output of DAC 2130 can drive an offset adjustment pin of amplifier 2110. RAM 2140 can be configured to provide the input of DAC 2130, and this input can contain digitized samples from ADC 2120 (e.g., samples that were previously inverted, scaled, and/or offset).

In these embodiments, a stimulation waveform is applied, and the artifact is recorded with amplifier 2110 in a low gain setting, such that the artifact falls within an amplifier 2110 dynamic range. To record the artifact without the eCAP signal, one stimulation pulse can be followed by a second pulse within the refractory period of the neurons, such that there is minimal or no eCAP signal following the second pulse. The artifact from that second pulse is recorded. The low-gain artifact output from amplifier 2110 can be digitized by ADC 2120. The output from ADC 2120 can then be inverted (e.g., negated) such that the artifact and its inverse sum to zero. Computing element 2150 can also apply scale and offset factors to the inverted artifact, such as to provide adjustability.

Next, a recording of the eCAP signal can be performed, with amplifier 2110 at a high gain setting (e.g., a setting configured to provide sufficient resolution to the eCAP signal). While the eCAP signal is recorded, the previously stored inverted artifact signal can be played back from RAM 2140, converted to an analog signal by DAC 2130, and applied to an offset pin of amplifier 2110. This playback can be synchronous with the sampling of the input signal. The offset pin can be positioned at a front end of amplifier 2110, where gain is low, and both input and offset are within a linear operating range. The previously recorded offset can be configured to negate the artifact component in the input signal. The result can comprise a reduction (e.g., significant reduction) in artifact amplitude, such that the result is within the linear range of amplifier 2110 at high gain setting. The eCAP signal, with a small residual artifact, can be accurately digitized by ADC 2120. Conventional artifact cancellation techniques, such as forward masking or template subtraction, can then be applied to fully extract the eCAP signal. Averaging of multiple ADC 2120 captures can be used to reduce noise, both in the low-gain artifact recording and the high-gain eCAP recording.

System parameters associated with the live playback (LPB) mode include but are not limited to: template amplitude.

Apparatus 10 can be configured to perform artefact cancellation by combining multiple methods (e.g., two or more of the artefact cancelation methods described hereabove or otherwise herein). In some embodiments, apparatus 10 "layers" an alternating polarity (AP) method, masker pulse (MP) method, and/or a scaled template (ST) method on top of a live playback (LPB) method, such as by reversing recording and reference electrodes. These combinations (LPB plus AP, LPB plus MP, and/or LPB plus ST) can reduce errors caused by LPB alone, such as errors due to the variation in the polarity of the leading pulse (anodic or cathodic) causing a change in the magnitude and latency of the eCAP response which distorts the signal. The LPB plus ST method can uniquely avoid this issue since the template can be of the same polarity as the stimulus.

Figures 9A, 9B, 9C, 9D:
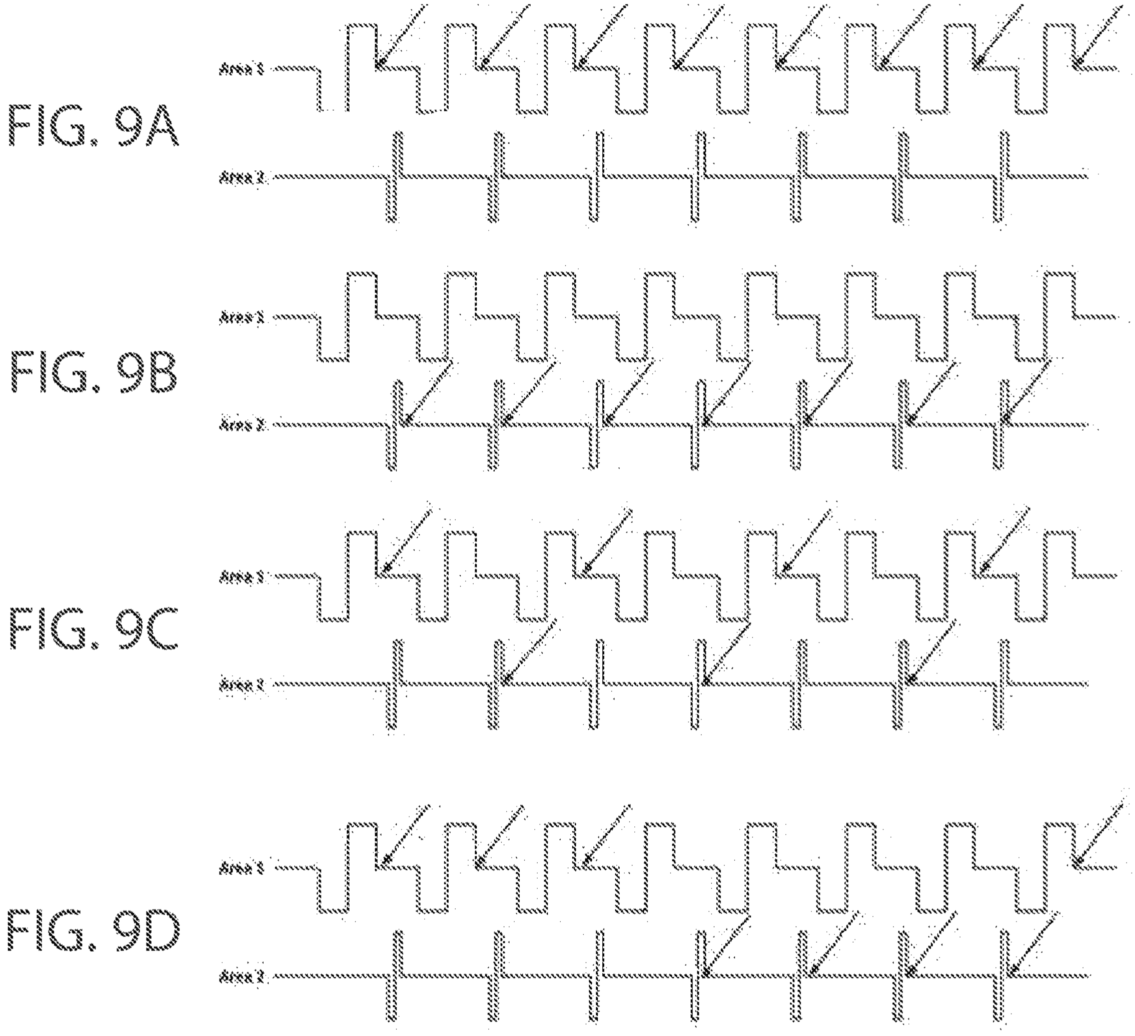
FIGS. 9A-9D illustrate waveforms associated with measuring eCAPs from two target areas, consistent with the present inventive concepts.

In some embodiments, apparatus 10 can utilize LPB and AP methods to make measurements during "standalone" use, where standalone use comprises a routine use of a trial stimulator (e.g. also referred to as a "trialing interface") by the patient. LPB mode can make measurements using stimulation parameter settings that are commonly used in stimulation therapy. LPB mode can be used when the stimulation signal comprises monophasic pulses (e.g., using passive recovery). When stimulation of multiple target areas (e.g., multiple target tissue volumes) is performed by apparatus 10, stimulation pulses can be delivered in a temporally interleaved arrangement. Apparatus 10 can be configured to perform eCAP measurements in a "round robin" arrangement in which eCAP measurements are made after a different pulse in each stimulation interval, such as is shown in FIGS. 9A-9D. In each of FIGS. 9A-9D, each arrow shown indicates the timing of an eCAP measurement being performed. In each of FIGS. 9A-9D, two target areas, Area 1 and Area 2, are shown. In some embodiments, apparatus 10 can be configured to perform the method of FIGS. 9A-9D in three or more areas. In FIG. 9A, apparatus 10 performs eCAP measurements after delivery of each pulse to Area 1. In FIG. 9B, apparatus 10 performs eCAP measurements after delivery of each pulse to Area 2. In FIG. 9C, apparatus 10 performs eCAP measurements in a single pulse alternating fashion, making an eCAP measurement after a pulse is delivered to Area 1, subsequently making an eCAP measurement after a pulse is delivered to Area 2, and so on in a repeating arrangement. In FIG. 9D, apparatus 10 performs eCAP measurements in a multi-pulse alternating fashion, making an eCAP measurement after each of a series of pulses are delivered in Area 1 (three pulses shown), subsequently making an eCAP measurement after each of a series of pulses are delivered in Area 2 (three pulses shown), and so on in a repeating arrangement. In another configuration, not shown, apparatus 10 can be configured to "dwell" on one target area (e.g., delivering a series of pulses with correlating eCAP measurements) until a particular criteria has been reached (e.g., an eCAP has been positively detected and/or a time duration has elapsed), after which apparatus 10 delivers a series of pulses to another target area until a particular criteria has been reached (e.g., the same criteria or different criteria as previously used). For stimulation of multiple areas using tonic stimulation, the area to be measured can be: fixed (e.g., one area is pre-selected); round-robin with each measurement; and/or round-robin with the inclusion of a "dwell" on each area for a fixed amount of time or until an eCAP is reliably detected. If active recovery is used, then an AP method can be used without using an LPB method. When using monophasic pulses, at low frequencies, apparatus 10 can be configured to delay charge recovery and measure the evoked response immediately after the stimulation pulse. In such instances, LPB method is not required except for the last pulse of the last train (e.g., when recovery starts).

With paired stimulation, apparatus 10 can apply LPB and AP methods after the tonic pulse (the recording electrodes will likely need to be excluded from those used in the stimulation waveform, such as a waveform including one or more trains and/or bursts). If active recovery is used, then apparatus 10 can use an AP method without an LPB method.

For some stimulation waveforms, apparatus 10 can be configured to measure the evoked response between pulses within a train, although the response may be partial (depending on the inter pulse interval). Similar to what is described hereabove for multi-area tonic stimulation, the measurement performed by apparatus 10 can be made: after a pre-selected pulse; in a round-robin manner after each pulse (e.g., where feasible); and/or in a round-robin manner after a dwell time or detected eCAP response.

Apparatus 10 can be configured to measure the evoked response after a group of pulses to optimize the number of pulses in the group. If monophasic pulses with passive recovery are used, apparatus 10 can apply a combined LPB method and AP method. For active recovery, the LPB method can be avoided. Applicable parameters include but are not limited to: the number of stimulation pulses; and/or charge recovery configuration (e.g., after each pulse and/or each group of pulses).

Figure 10:
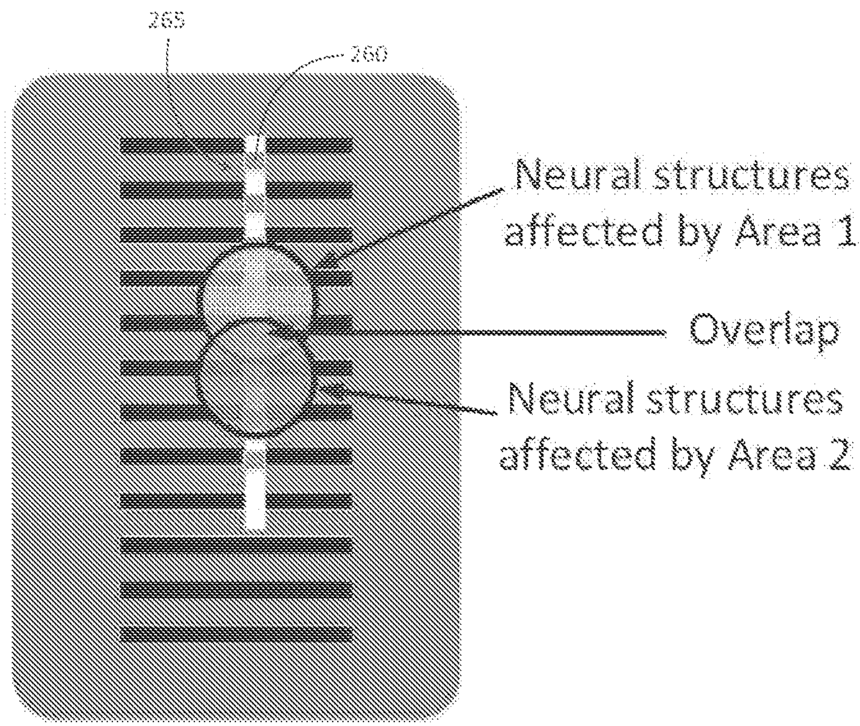
FIG. 10 illustrates an anatomical view of an implanted lead including multiple stimulation elements, consistent with the present inventive concepts.

Referring now to FIG. 10, an anatomical view of an implanted lead including multiple stimulation elements is illustrated, consistent with the present inventive concepts. Lead 265, including multiple (eight shown) stimulation elements 260, has been implanted in a patient to stimulate area 1 and area 2 as shown. If two or more stimulation areas within a stimulation paradigm SP target some overlapping neural structures, then the stimulation efficiency for each area is decreased. In FIG. 10, area 1 and area 2 have the overlapping portion (e.g., volume of tissue) shown. The stimulation pulses delivered for each area can be non-overlapping in time and therefore the amount of interaction (meaning the number or type of neural structures that are affected by both areas) depends on the temporal gap between the pulses from each area. At relatively high rates (e.g., at least 100 Hz, or at least 500 Hz) there may be significant interaction in the overlapping portion. By measuring the neural response in the overlapping portion, the degree of interaction can be quantified. In some instances, it can be advantageous to optimize (e.g., maximize) the interaction, and in other instances it can be advantageous to minimize the interaction. Depending on the particular therapeutic goal, the stimulation areas can be brought closer together (by selecting stimulation elements 260 that are physically closer together) or the stimulation areas can be brought farther apart, such as while evaluating the interaction via eCAP measurements (in a pre-defined overlap area).

Section 1—Introduction to Applicant-Conducted Studies

Figure 11A:
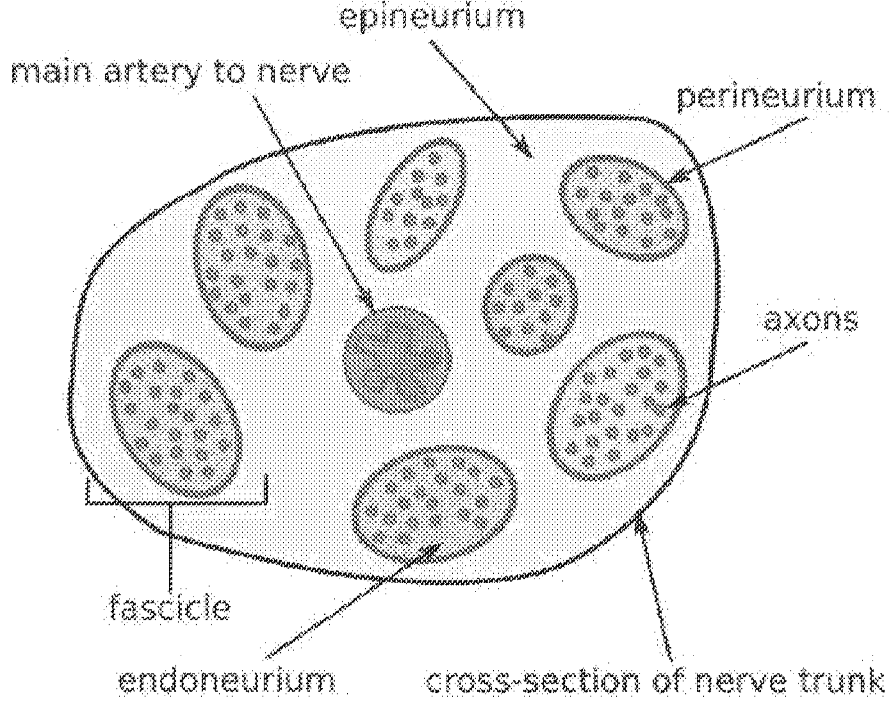
FIGS. 11A-11Q illustrate various schematics, graphs, and stimulation models of a medical apparatus, consistent with the present inventive concepts.

Referring now to FIG. 11A, an anatomical schematic depicting the geometry of fascicles and nerve fibers within a nerve bundle is illustrated, consistent with the present inventive concepts. The peripheral nervous system (PNS) of a mammalian patient has a complex anatomical structure. Stimulation of nerve fibers in the PNS not only depends on the nerve fiber diameter and myelination, as well as its location within the nerve; packing fraction; and fascicle distribution in a nerve bundle. The impact of variation in PNS anatomy and the distance of stimulating electrodes 260 (e.g. electrodes) from the nerve on generating an action potential is described hereinbelow.

Applicant has developed a mathematical model to capture variation in the packing fraction and fiber diameter through an effective fascicle conductivity evaluation. A linear activation function was utilized to analyze the impact of this effective conductivity and fascicle distribution on the generation of action potentials. The effect of stimulation element 260 distance on activation function and total current through a nerve bundle was also studied. The simulation results indicated that the PNS anatomy and stimulation element 260 distance have a significant effect on the threshold and selectivity of stimulation.

The therapeutic application of artificial peripheral nervous system stimulation has been a field of growing interest throughout the last few years, particularly as an effective tool for the treatment of chronic pain. According to the gate control theory of pain, non-painful input closes the nerve gates to painful inputs. Painful nociceptive stimuli are carried by Aδ and C nerve fibers, while Aα, Aβ nerve fibers carry non-nociceptive stimuli for proprioception and touch. The gate control theory implies that the effectiveness of pain relief depends on the selective stimulation of Aα, Aβ nerve fibers within a nerve bundle. In order to achieve preferential stimulation of the Aα and Aβ nerve fibers within a nerve bundle, it is necessary to consider the complexity of, and variation in, the anatomy of a nerve bundle.

Anatomical studies of PNS nerves have shown that the nerve bundle construction varies significantly across mammalian subjects. Different features of nerve bundle construction, such as: packing fraction (ratio of total fiber cross-sectional area to fascicle cross-sectional area); quantity of nerve fibers in a fascicle; spatial distribution of nerve fibers within a fascicle; and spatial distribution of fascicles within a nerve bundle vary across patients. Based on literature, it can also be said that these anatomical features differ even across different nerve bundles within a single patient. Furthermore, packing fraction changes with age and sex, and changes are also associated with the presence of diabetes and other neuropathies. An improved computational simulation model can be used to analyze the effect of these features on the stimulation of the associated nerves in the PNS.

Computational simulation of PNS nerve bundle is an effective method to analyze selectivity of nerve fibers. A PNS simulation model of the present inventive concepts can consider geometry and material properties of the nerve bundle along with stimulation element 260 geometry and its placement relative to the nerve. Historically, PNS simulation models have primarily focused on electrode placement and current stimulation patterns (e.g. current intensity, frequency, and/or pulse shape) to analyze the selectivity of nerve fibers, but they have rarely considered variation in anatomy of PNS nerve bundles. Though the anatomical features change with patients, historical data in the literature shows that PNS simulations are generally performed for a fixed geometry and a fixed set of material properties. Since the anatomical features affect the electric potential that is generated by an external stimulating electrode, it is important to analyze the associated impact on stimulation.

The apparatus, systems, and methods of the present inventive concepts can be configured to perform one or more algorithms (e.g. algorithm 15) that are derived from and/or otherwise based on a mathematical model that estimates the effective conductivity of a fascicle based on anatomical features. Apparatus 10 can be configured to deliver one or more stimulation paradigms SP that are based on (e.g. optimized based on) one, two, three, and/or all of the following four factors: conductivity of fascicles based on packing fraction and/or nerve fiber type; impact of effective conductivity values on linear activation function values; impact of fascicle distribution on an activation function; total current passing through a nerve; and combinations of these. Described hereinbelow are simulation results demonstrating the effects of the conductivity estimate on electric potential. An analysis is presented to assess the impact that electrode distance from a nerve bundle has on electric potential generation. First presented is a mathematical model to estimate the effective conductivity of fascicles based on packing fraction and nerve fiber type. Presented second is the impact of the effective conductivity values on linear activation function values. Presented third is the impact of fascicle distribution on the activation function. Presented fourth is an analysis of the total current passing through the nerve bundle for stimulation elements 260 placed at different distances with respect to the nerve bundle.

Section 2—Effective Fascicle Conductivity Computation

Nerve fiber diameters range from 1 μm to 10 μm, whereas fascicle diameters are in the range of 0.075 mm to 1 mm and nerve bundle diameters are of the order of 5 mm to 15 mm. Modeling a geometry comprising parts ranging from 1 μm to 15 mm in a single simulation model is difficult. Hence in the PNS model, nerve fibers are not considered explicitly, but their contribution is considered in computing the effective conductivity of a fascicle. Generally, simulation models assign the same anisotropic effective conductivity values for all fascicles, however the effective conductivity of a fascicle will depend on fiber type and their packing fraction (ratio of total fiber cross-sectional area to fascicle cross-sectional area) within a fascicle.

As shown in FIG. 11A, a nerve bundle has fascicles surrounded by epineurium. Each fascicle has nerve fibers surrounded by endoneurium and perineurium that forms a thin layer around each fascicle. Nerve fibers are of two types: myelinated and unmyelinated. Each myelinated nerve fiber is surrounded by a myelin sheath, whereas in unmyelinated fibers the myelin sheath is absent. The nerve fibers in the PNS travel between muscles and the spinal cord (central nervous system, or CNS). The effective conductivity of a fascicle along its travel axis (axial conductivity) is different than in a cross-sectional plane perpendicular to the travel axis (radial conductivity). Based on this geometry, the computation of effective conductivity is described below.

Table 1 is a table of properties for the biological materials listed.

TABLE 1

| Conductivity | Direction | Value (S/m) |
| --- | --- | --- |
| Endoneurium | radial | 0.0826 |
| Endoneurium | axial | 0.0021 |
| Axon | all directions | 1.4286 |
| Myelin sheath | all directions | 7.3e−8 |
| Perineurium | all directions | 0.0021 |

TABLE 1-continued

| Conductivity | Direction | Value (S/m) |
|---|---|---|
| Epineurium | all directions | 0.0826 |
| Fat | all directions | 0.04 |

Section 2.1—Effective Axial Conductivity

Figure 11B:
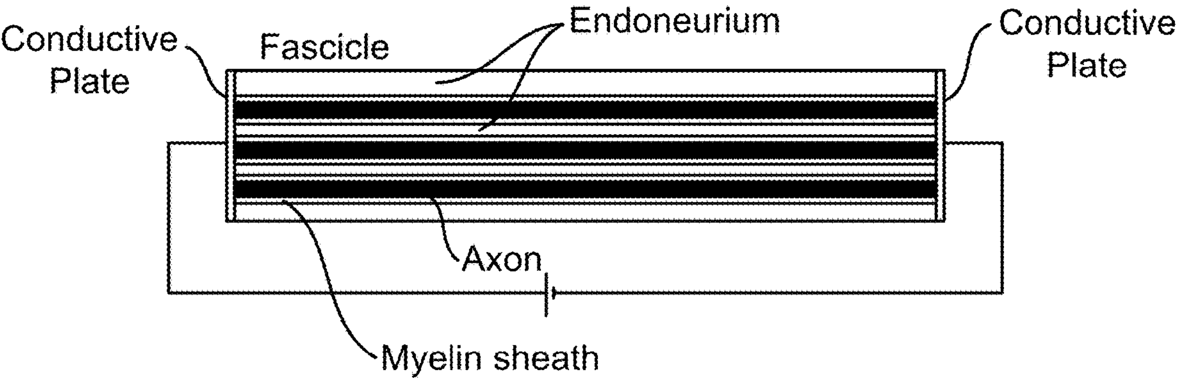

In computing an effective conductivity estimate for a fascicle, it can be assumed that nerve fibers travel parallel to each other, such as is shown in the model presented in FIG. 11B. A fascicle primarily consists of three types of biological materials: endoneurium; axon; and myelin sheath (the myelin sheath is absent in unmyelinated fibers). If a fascicle is placed between two conducting plates, as shown in FIG. 11B, and a potential difference is applied between the plates, then the total current flowing through the fascicle will depend on the effective conductance of the fascicle. This effective conductance can be computed by assuming nerve fibers and endoneurium can be modeled as conductors connected in parallel. The conductance, conductivity, cross-sectional area, and length, are related as follows:

$$C = \frac{\sigma A}{l} \tag{1}$$

where C is the conductance [S], σ is the conductivity, A is the cross-sectional area [$m^2$] and l is the length [m].

For conductors connected in parallel, the effective conductance value is the sum of the individual conductance values.

$$C_{eff} = C_a + C_m + C_e \tag{2}$$

$$\frac{\sigma_{eff} A_{total}}{l} = \frac{\sigma_a A_a}{l} + \frac{\sigma_m A_m}{l} + \frac{\sigma_e A_e}{l} \tag{3}$$

Using $$A_{total} = A_a + A_m + A_e,$$

equation 3 can be rearranged to get the expression for the effective fascicle conductivity:

$$\sigma_{eff} = \frac{A_a \sigma_a + A_m \sigma_m + A_e \sigma_e}{A_a + A_m + A_e} \tag{4}$$

where $A_a$ is total cross-sectional area of axons, $A_m$ is total cross-sectional area of myelin and $A_e$ is total cross-sectional area of endoneurium. $\sigma_{eff}$ represents the effective fascicle conductivity, $\sigma_a$ represents conductivity of an axon, $\sigma_m$ represents conductivity of a myelin sheath, and $\sigma_e$ represents conductivity of endoneurium. The total area of axons, myelin sheath and endoneurium depends on the packing fraction of nerve fibers in a fascicle. If the packing fraction of fibers and total cross-section area of a fascicle are known then the total area of axon, myelin sheath and endoneurium can be calculated. The following formula assumes that a fascicle has a single type of myelinated fiber with a fixed cross-section area:

$$A_a + A_m = \underline{pA}$$

$$A_e = (1 - \underline{p)A}$$

where, p is packing fraction, ratio of total fiber cross-sectional area to fascicle area and A is total cross-sectional area of a fascicle.

Section 2.2—Effective Radial Conductivity

Figure 11C:
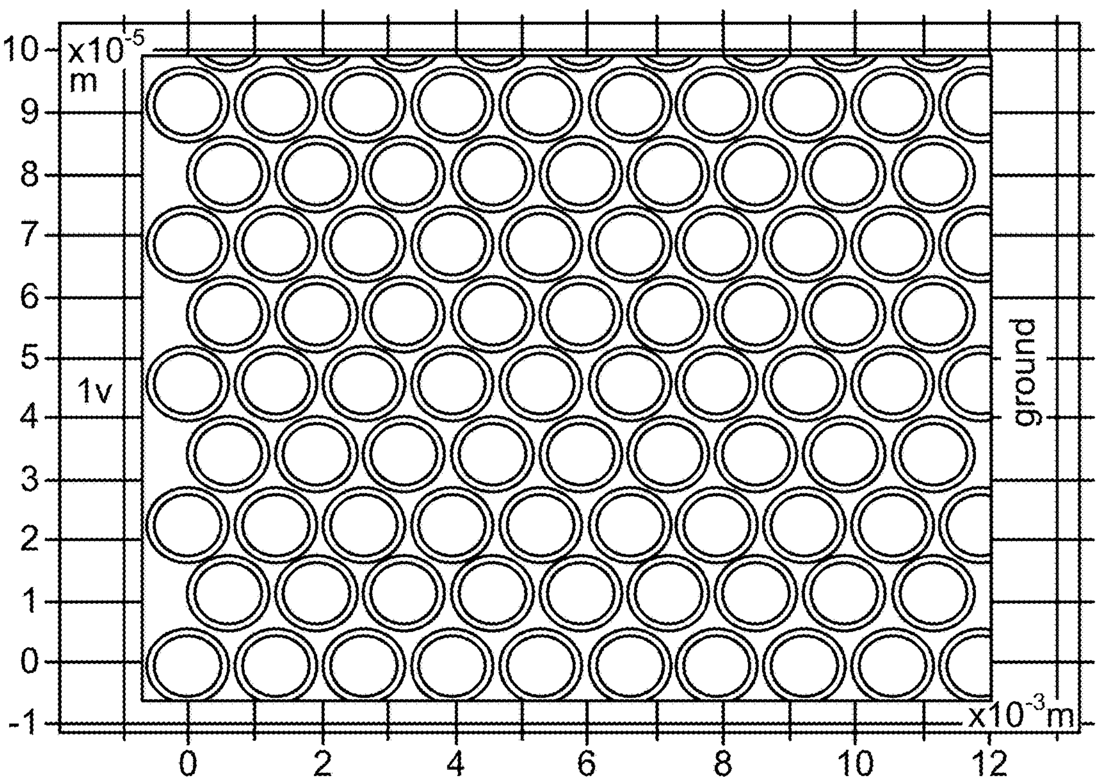

The effective radial conductivity was computed through simulations. Referring now to FIG. 11C, a square cross-sectional area of Aα nerve fibers considered for computing effective radial conductivity is illustrated. The packing fraction of FIG. 11C is 70%. FIG. 11C can represent an infinitely long box containing uniformly distributed nerve fibers. A one volt potential difference was applied across opposite sides of the box and the remaining two sides were insulated.

The total current flowing through the box was measured using finite element analysis (FEA) simulations. In order to compute the effective radial conductivity, another simulation was performed where the box dimensions were kept the same, but nerve fibers were replaced by a pseudo material. The conductivity of the pseudo material at which total current flowing through the box matches the current when nerve fibers are present, is the effective radial conductivity for the packing fraction. No changes in effective radial conductivity were observed with varying fiber diameters. The cross-sectional area of fibers was computed using the mean diameter values listed in Table 2.

TABLE 2

| Fiber Type | Value μm |
|---|---|
| C diameter | 0.8 |
| Aα diameter | 16 |
| Aβ diameter | 9 |
| Aδ diameter | 6 |
| Aα myelin sheath thickness | 1.75 |
| Aβ myelin sheath thickness | 1.49 |
| Aδ myelin sheath thickness | 0.2 |

Figure 11D:
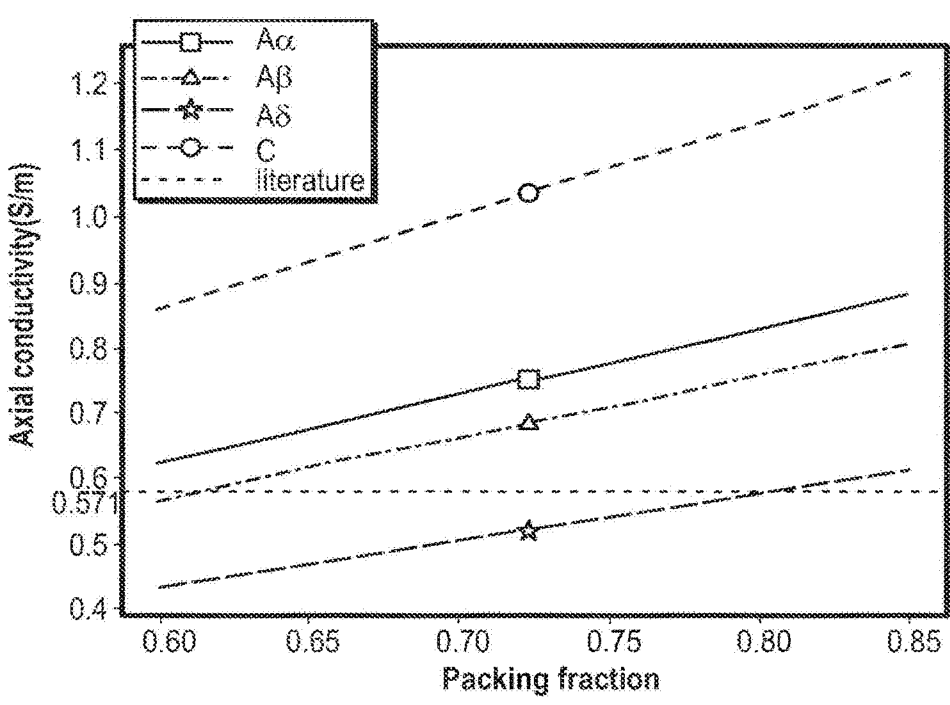
Figure 11E:
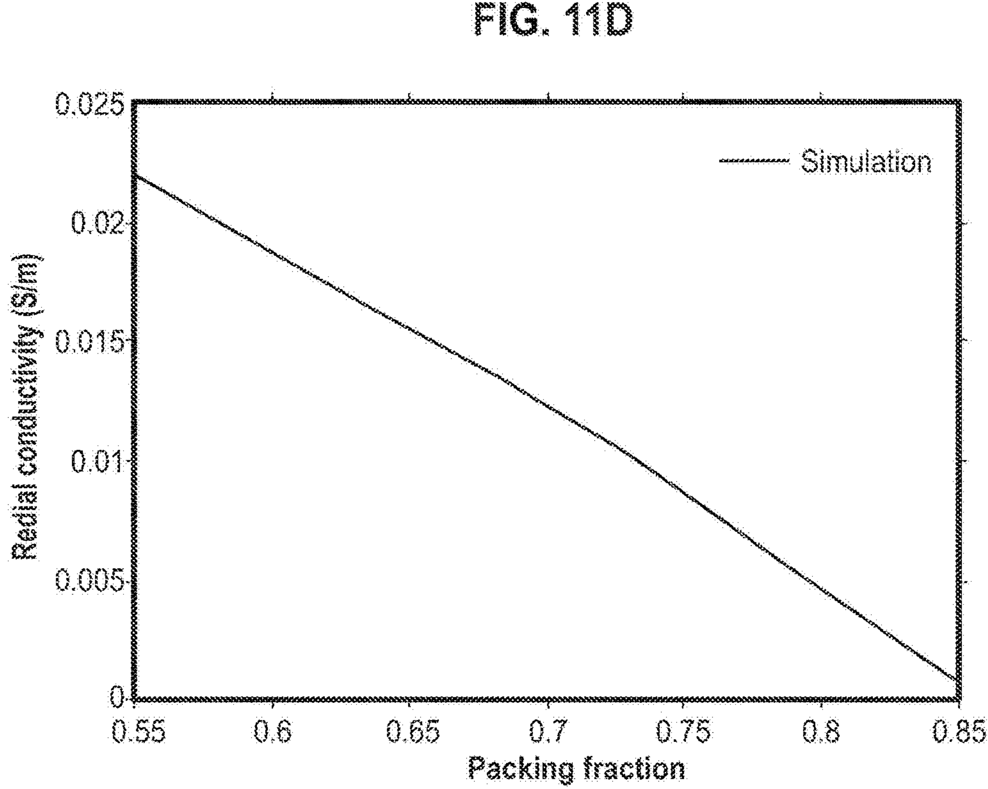

Assuming that a single type of fiber is present in a fascicle, and that a myelin sheath acts as a perfect insulator, FIGS. 11D and 11E show the variation in radial and axial conductivity values as a function of packing fraction. In literature, 0.571 S/m is often used as axial conductivity (shown by the dashed line in FIG. 11D) and 0.0826 S/m (endoneurium conductivity in Table 1) is used as radial conductivity. Using a single value of conductivity ignores the wide variation in values that exists due to the fiber type. The effective radial conductivity value approaches endoneurium conductivity as packing fraction tends to 0.0. Based on the intersection of the dotted line with other lines in FIG. 11D, it can be said that the value seen in literature (0.571 S/m) corresponds to a packing fraction of 0.5-0.6 for Aα and Aβ fibers, and a packing fraction of 0.8 for Aδ fibers.

Section 3—Stimulation of a Peripheral Nerve

Stimulation of axons in a PNS nerve bundle can be predicted using FEA simulations. The activation potential can be computed from the second spatial derivative of the extracellular potential distribution (V) along the axon axis (z axis in applicant's simulations). This mathematical model is referred to as activation function and this linear estimator can be denoted by: $Q(X)=(\partial^2 V/\partial z^2)$ at the site (X). Previous work has shown that the response of myelinated and unmyelinated fibers to extracellular stimulation is qualitatively similar as long as Q(X) does not vary too much within the inter-nodal distance between nodes of Ranvier. Since simulations described below have a single source electrode the Q(X) is a smooth function and can be used to analyze relative values across different packing fractions. This study performs quasi-static simulations to analyze relative change in Q(X) values.

Section 3.1—Analysis of O(X) for Aα Fascicles with Different Packing Fraction

Figure 11F:
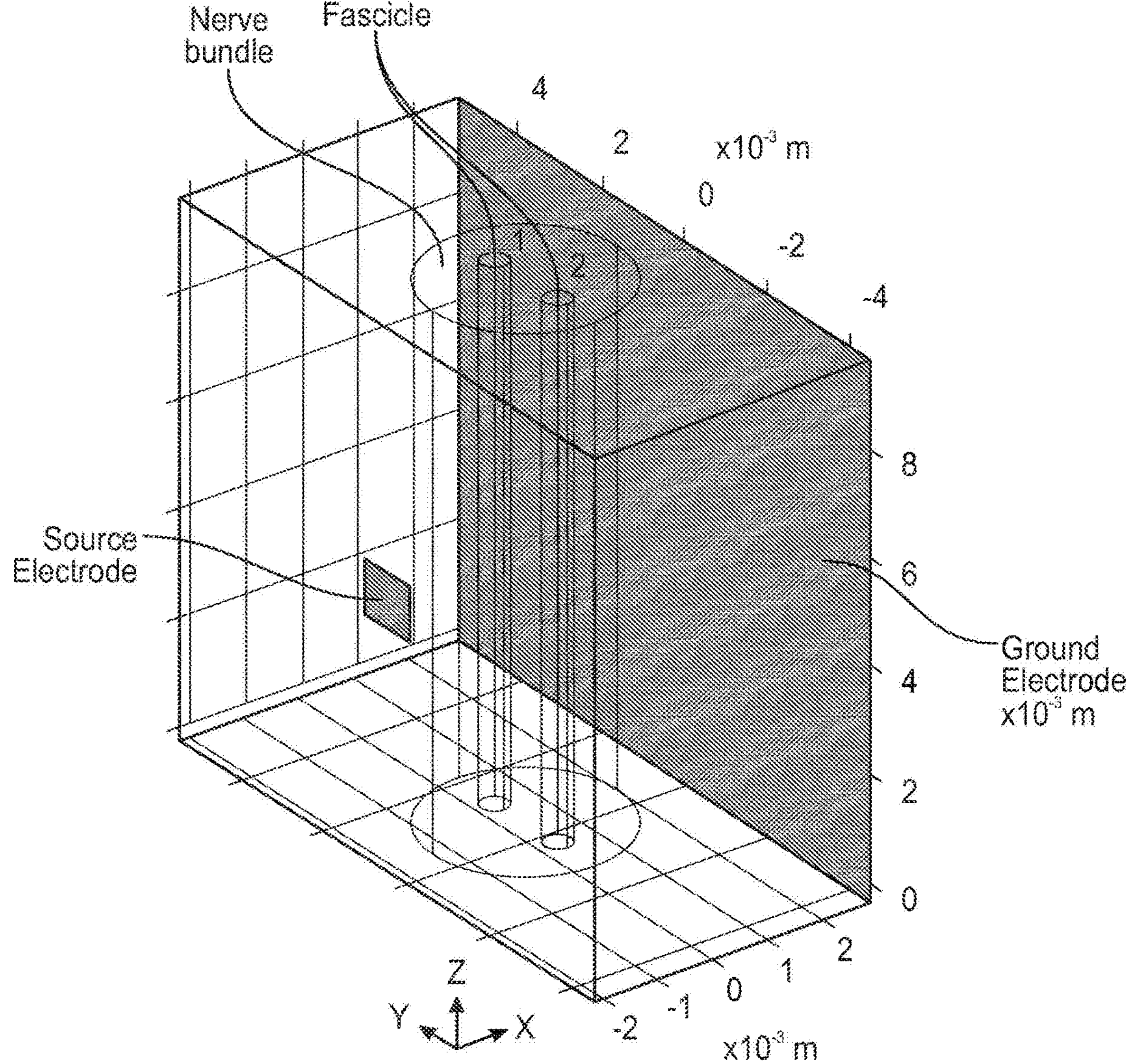
Figure 11G:
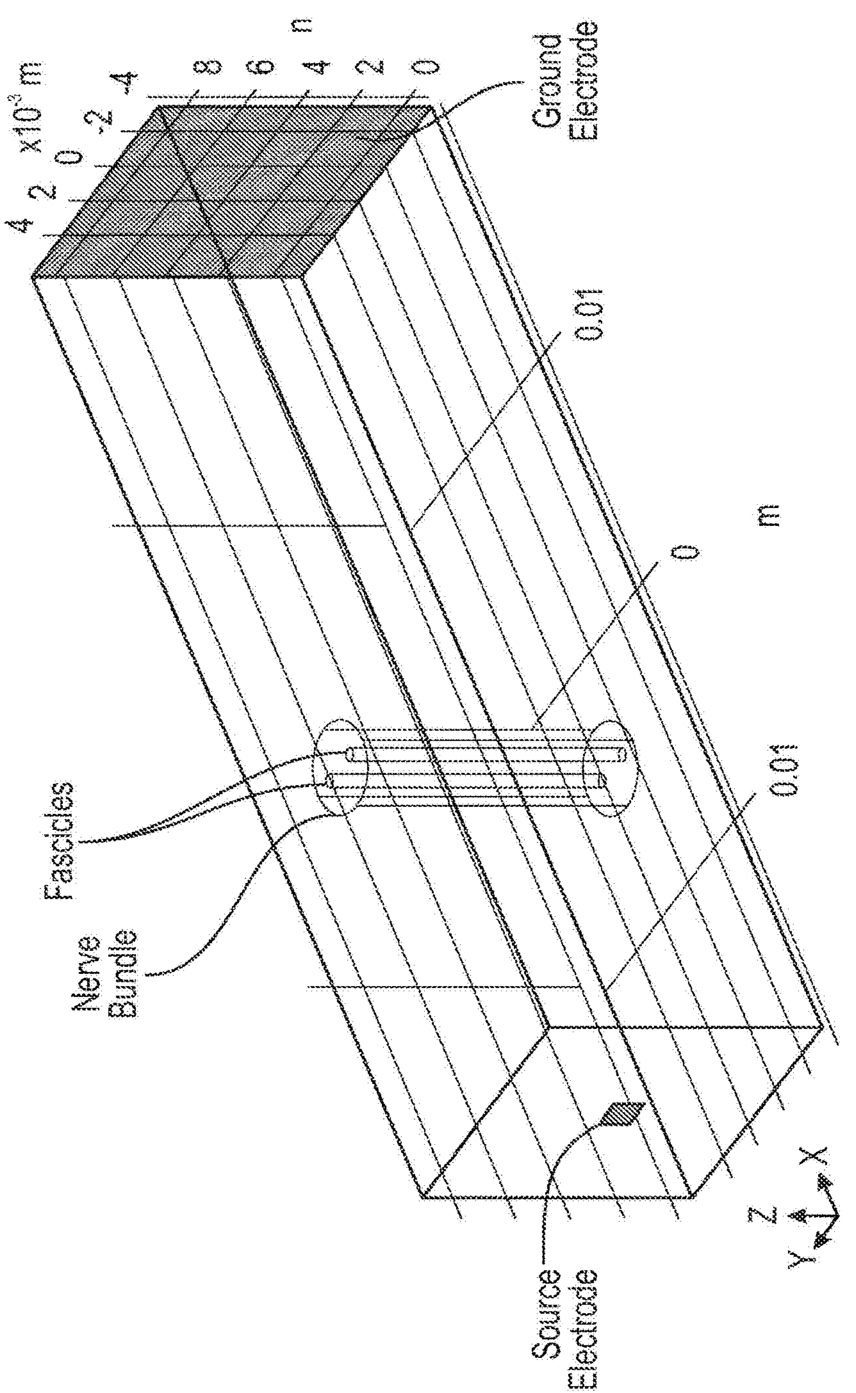

Anatomical studies have shown that packing fraction varies over a wide range of values. An analysis was performed regarding the effect of the variation in packing fraction using two fascicles with different packing fractions. FIGS. 11F and 11G represent two geometries, each having the two fascicles but with different distances between a stimulation element 260 (e.g. an electrode) and nerve bundle. In the first geometry shown in FIG. 11F, source and ground electrodes were at 1 mm distance from the nerve bundle; and in the second geometry shown in FIG. 11G, the source electrode was at 15 mm and ground electrode at 20 mm distance from the nerve bundle. In both of these geometries, fascicle 1 had a 0.55 packing fraction and fascicle 2 had a 0.7 packing fraction of Aα fibers. As described in the previous section, the effective conductivity of the fascicles was decided based on the packing fraction and fiber type. Both the fascicles were placed at an equal distance from the source electrode. Perineurium boundary surrounding the fascicle had a width equal to 3% of the fascicle diameter.

A constant current was sourced through the source electrode and an electric potential was computed in the domain using FEA. In order to compare results between the two models (FIGS. 11F and 11G), it was ensured that the same amount of current enters the nerve bundle in both cases. Except for the source and ground electrodes, all remaining surfaces were insulated. In order to analyze the effect of different packing fractions Q(X) values were plotted along the fascicle axis.

Figure 11H:
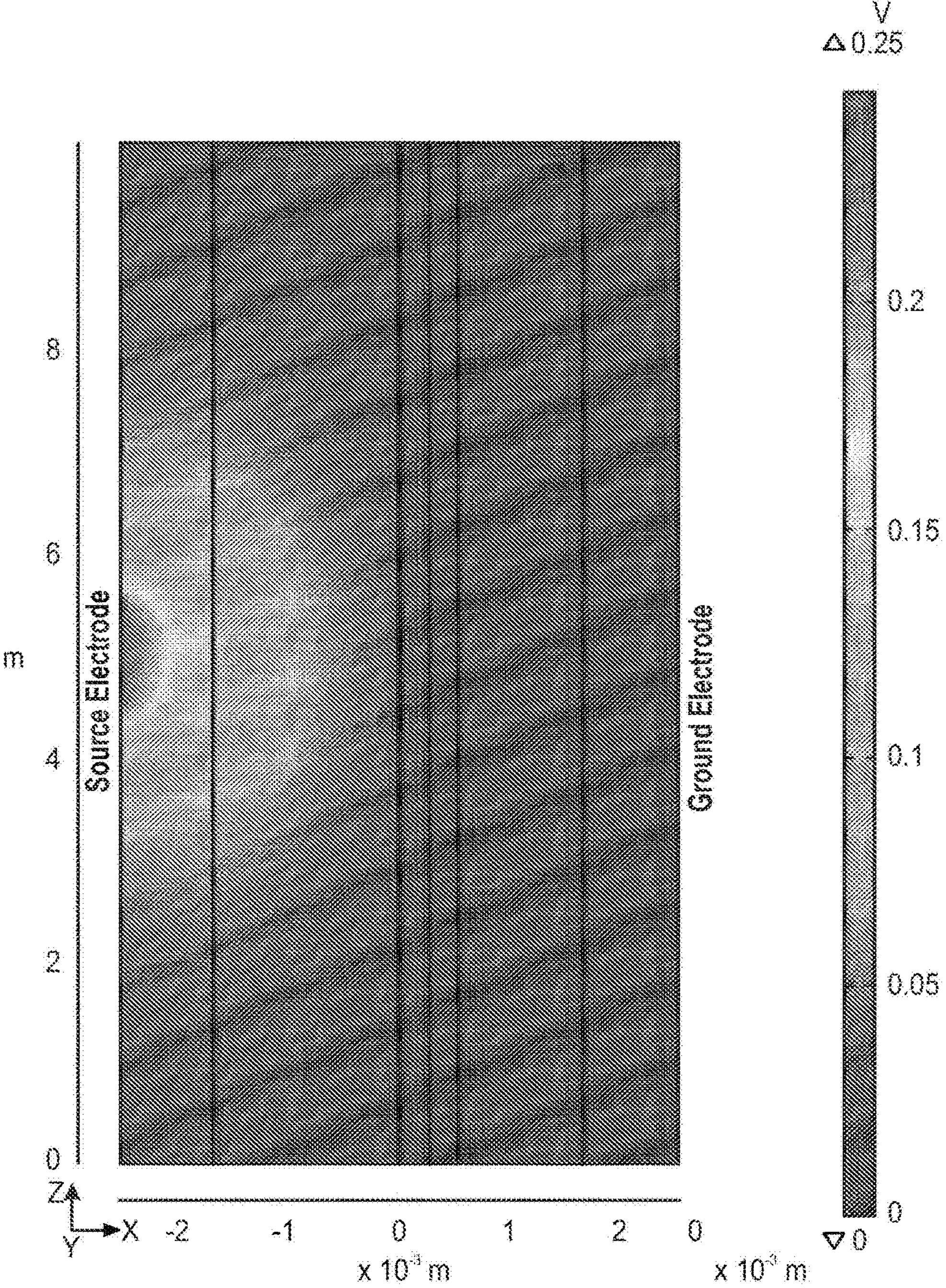
Figure 11I:
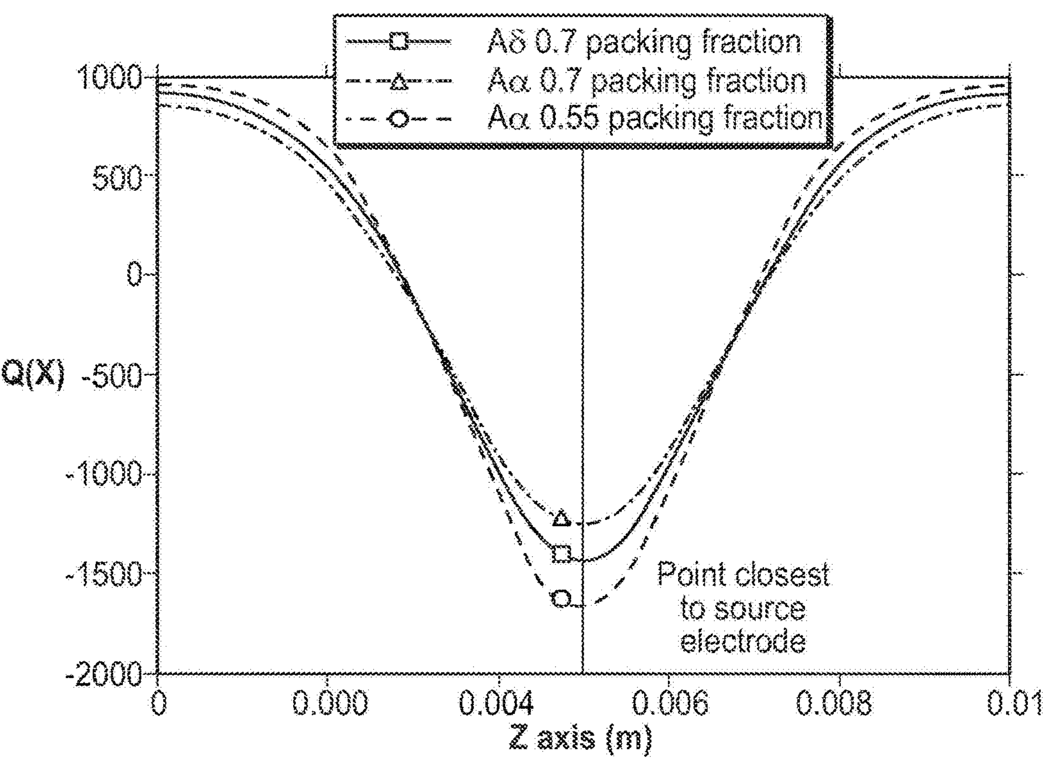
Figure 11I:
Figure 11J:
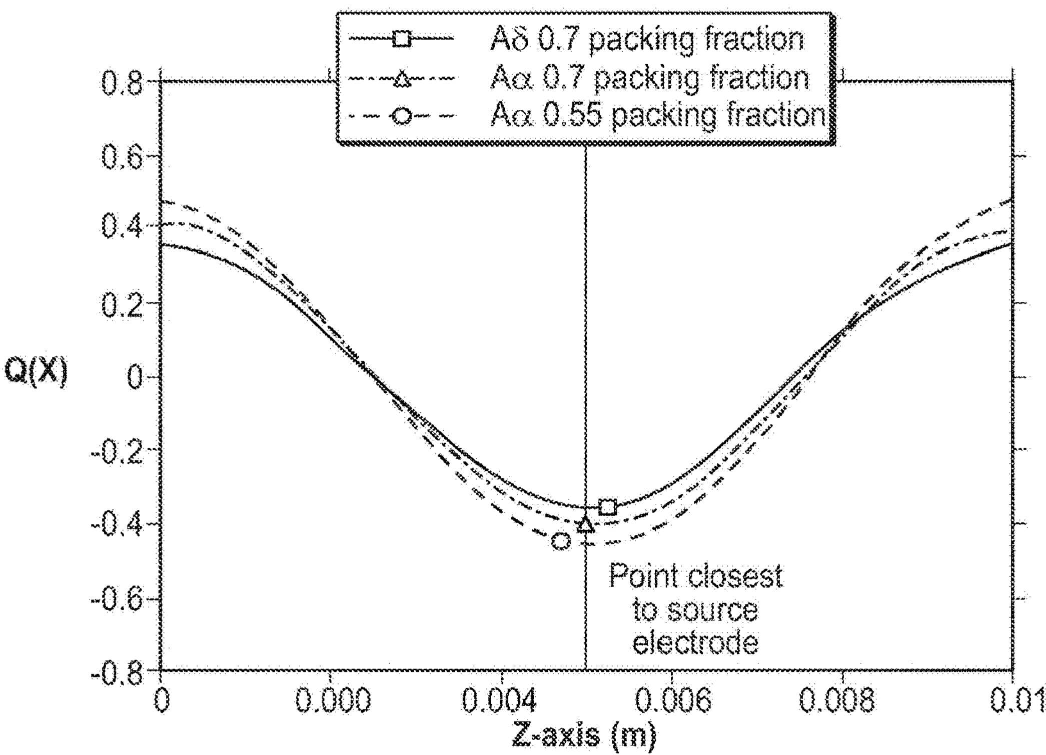

The Q(X) along the center line (red lines in FIGS. 11F and 11G) of both fascicles are shown in FIGS. 11I and 11J for the two geometries respectively. In the region closest to the source electrode, Q(X) is negative, while it is positive towards the extremities of the fascicle. This difference is because, as shown in FIG. 11H, along the axis of the fascicles, electric potential decays from the center of fascicle to its extremities. Though the trend of Q(X) in both fascicles is similar, the value of Q(X) differs considerably. Positive values of Q(X) indicate depolarization, whereas negative values indicate hyperpolarization. This result clearly indicates that packing fraction affects Q(X) considerably, and hence has an impact on the generation of the action potential. It can also be observed even in the second model (FIG. 11G) where the source electrode is located at 15 mm from the nerve bundle, that Q(X) trends remain the same even though overall Q(X) magnitude is small as the electric potential is comparatively uniform. Simulations were also performed by applicant by placing the ground electrode further away from the nerve bundle, and the Q(X) trends remained consistent.

Section 3.2—Analysis of O(X) for Aα and Aδ Fascicles with the Same Packing Fraction In the simulation experiment described above, the same geometric arrangement (FIGS. 11F and 11G) was considered, but effective conductivity values of the second fascicle were evaluated assuming only Aδ fibers in the fascicle. Both fascicles had the same packing fraction of 0.70. Variation of Q(X) along the fascicle axis is shown in FIGS. 11I and 11J. There was no considerable change in Q(X) values for the Aα fascicle when compared with previous experiments, such as those described in Section 3.1. It can be observed that the Q(X) values of Aδ fascicle lie between Q(X) values of two Aα fascicles with 0.7 and 0.55 packing fractions.

The relative comparison of activation function Q(X) among these simulation results shows that a stimulation signal which will generate an action potential in nerve fibers of both Au fascicles will also generate an action potential in Aδ fascicle. This result implies that utilizing a single threshold value for the activation function to selectively activate Aα fibers will be challenging if not impossible. This result clearly shows that packing fraction has a significant impact on the effect of activation function values. Furthermore, while analyzing other locations in the fascicles (apart from the center line), applicant found that the values of activation function change across the fascicle cross-section. These observations highlight the challenge of using a single current threshold to stimulate all non-nociceptive nerve fibers.

Section 4—Effect of Fascicle Distribution on PNS Stimulation

Figure 11K:
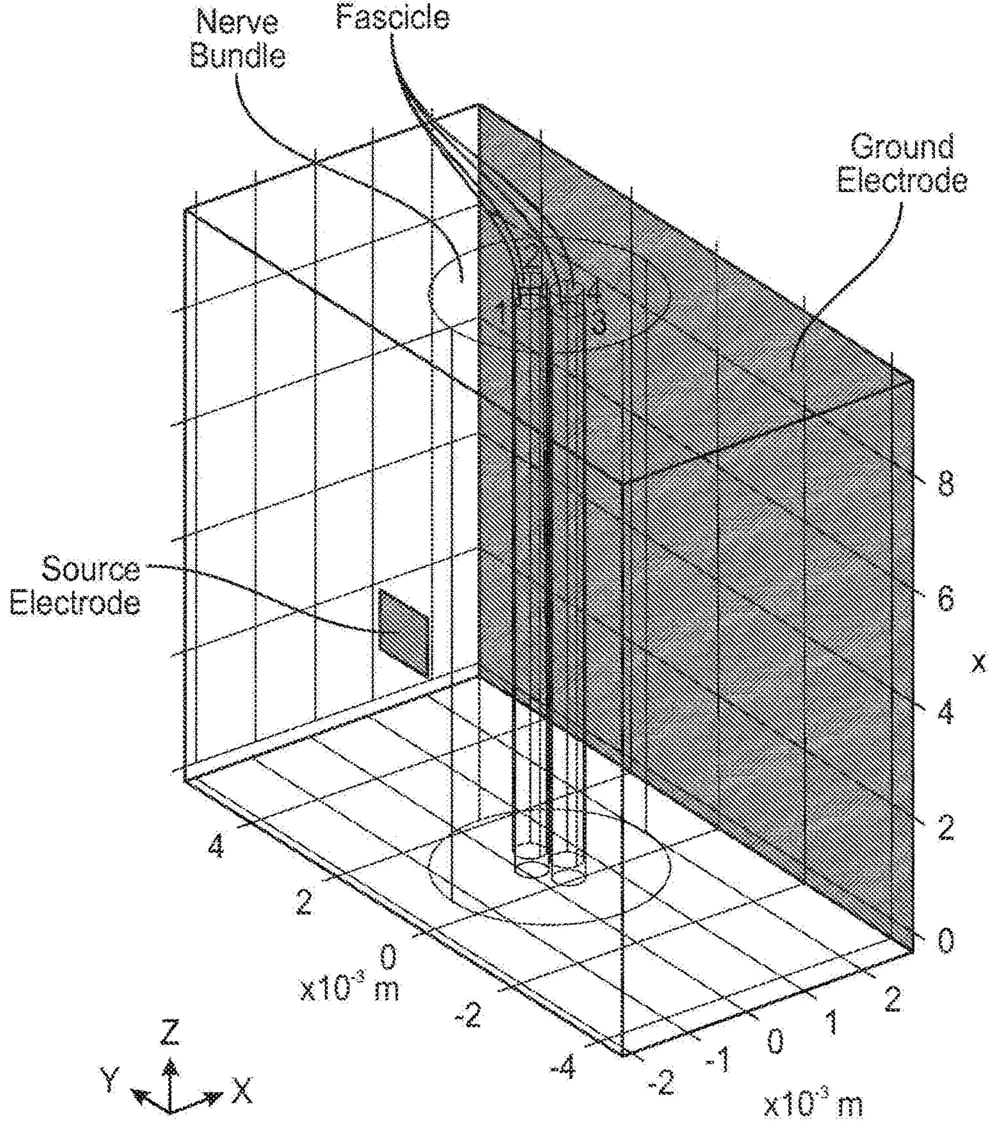
Figure 11L:
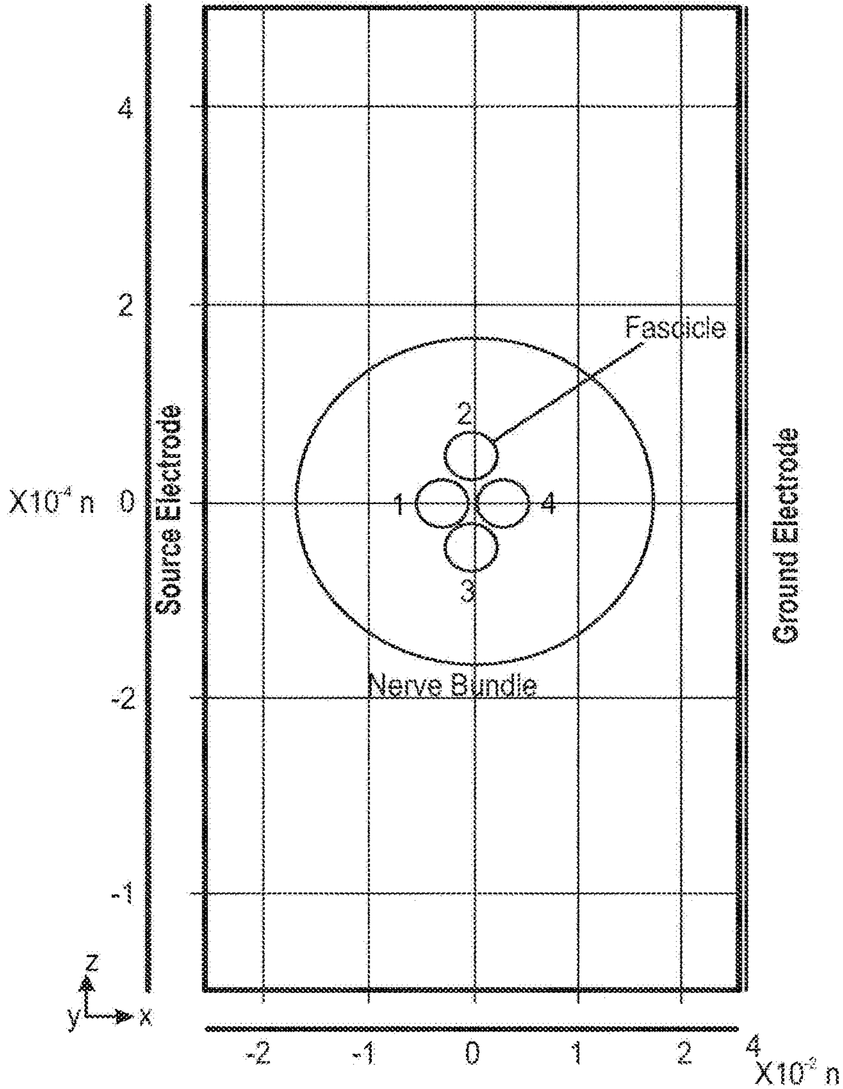
Figure 11M:
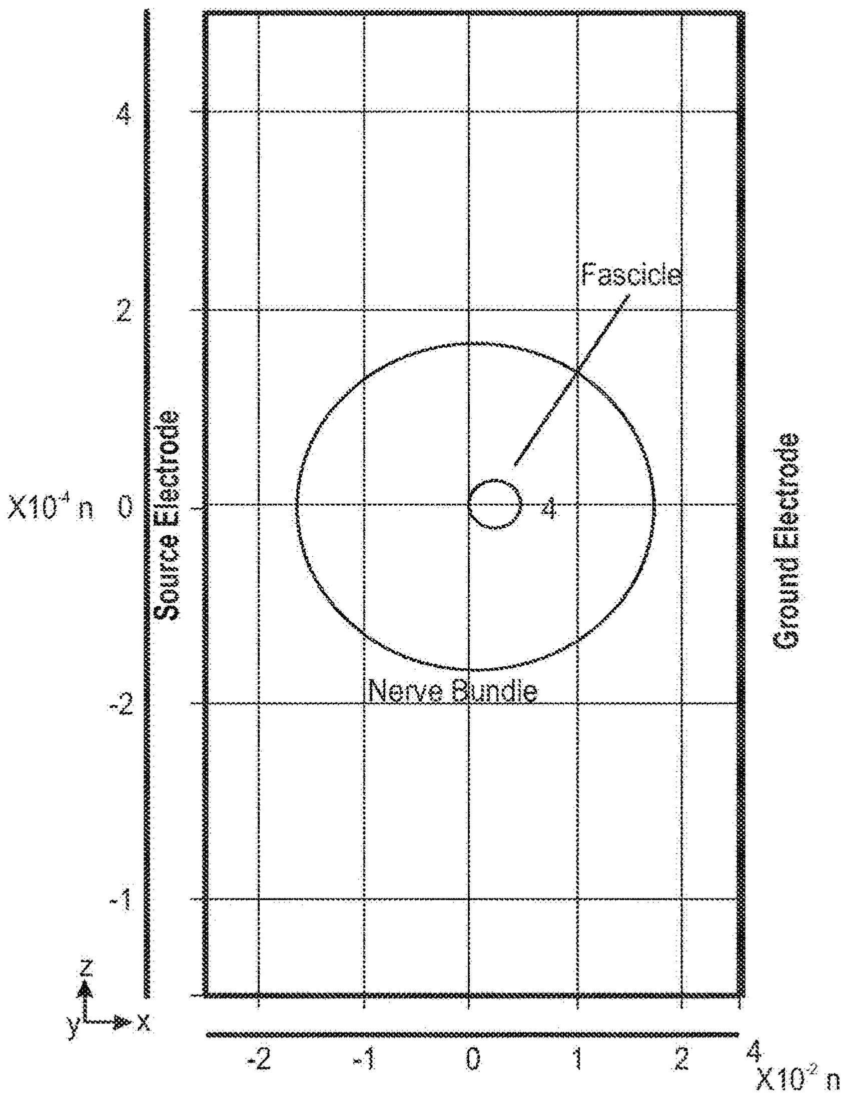

It is known that fascicle distribution within a nerve bundle varies across different patients. In addition to this variability, the number of fascicles in a PNS nerve bundle changes across patients. Distribution of fascicles within a nerve bundle affects the overall potential field within the bundle. In order to analyze this effect, applicant performed two simulation experiments. The first experiment used a model including four fascicles, each having an effective conductivity of Aα fibers with a packing fraction of 0.7 (reference FIG. 11K). The second experiment only considered the fourth fascicle, the fascicle under test. FIGS. 11L and 11M depict the top views of the fascicles in the two experiments, respectively. These two experiments evaluated the effect of relative position of the fascicles with respect to the source electrode. In both experiments, linear estimator Q(X) at the center line of the fascicle under test was analyzed.

Figure 11N:
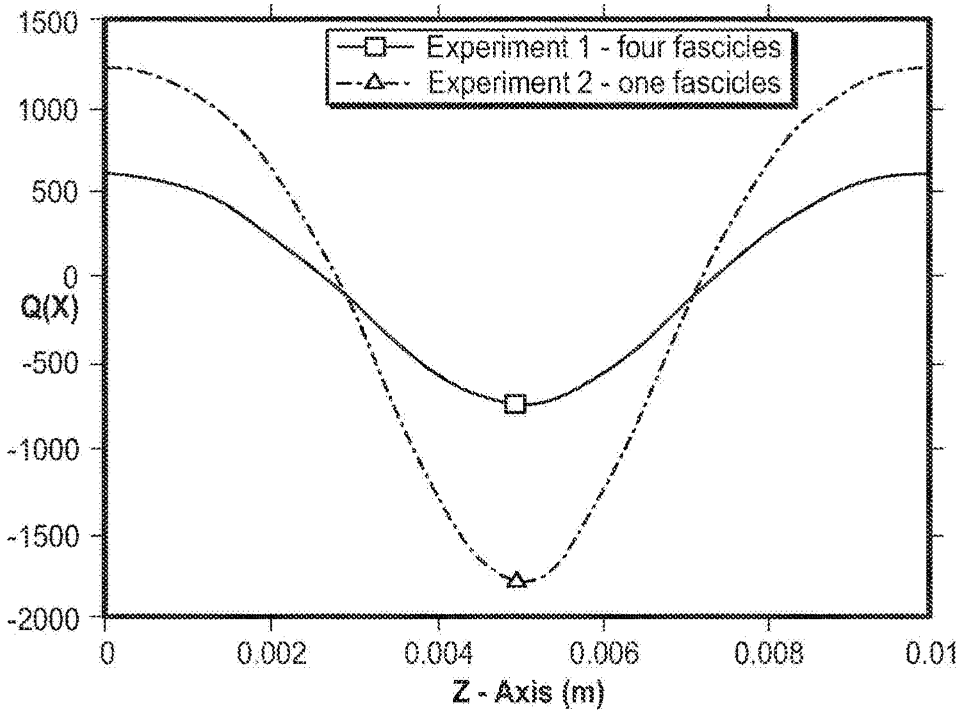

The results of these experiments are shown in FIG. 11N. It can be observed that positive Q(X) values when all fascicles are present are considerably lower than Q(X) values when only the test fascicle is present in the nerve bundle. Since positive Q(X) values in experiment 2 (of single fascicle) are higher than the values in experiment 1 (with four fascicles), the same magnitude of source current applied can lead to generation of an action potential in experiment 2 but not in experiment 1. This result shows that, even though the fiber type, packing fraction and location of a test fascicle is the same in both the experiments, the presence of fascicles between the test fascicle and the source electrode changes the activation function values. This in turn implies that the distribution of fascicles in a nerve bundle affects the generation of action potentials. The likely reason for this observation is that the total resistance of the path between the source electrode and the test fascicle changes based on the fascicle distribution within a nerve bundle. In order to generate an action potential for a different fascicle distribution, better control over the electric potential in a nerve bundle is needed. This control can be achieved by placing more stimulation elements 260 (e.g. electrodes) around a nerve bundle. More electrodes will increase the probability that an appropriate potential field can be generated to selectively stimulate desired nerve fibers. Since fascicle distribution varies across patients, selective stimulation of desired nerve fibers will enable the delivery of a personalized therapy while minimizing unwanted stimulation. These results suggest that apparatus 10 should include one or more implantable devices 100 that include several stimulation elements 260, in order to maximize the probability of selectively depolarizing the target fibers while avoiding depolarization of others.

Figure 11O:
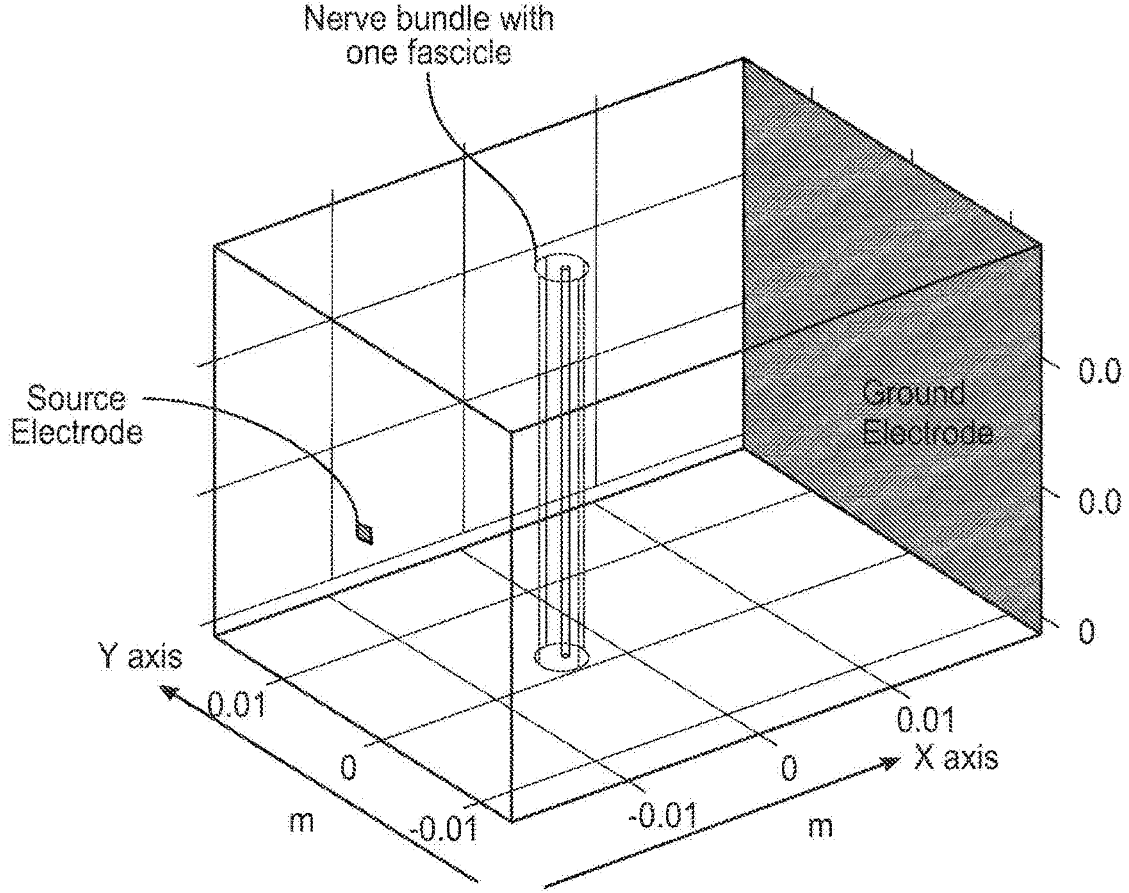

Section 5—Effect of Distance of Electrode on Current Passing Through a Nerve Bundle This simulation experiment performed by applicant analyzes the effect of variation in the distance of a stimulation element 260 (e.g. an electrode) from a nerve bundle on current passing through a nerve bundle. In the simulation experiment, a source electrode and a ground electrode were placed at different distances with respect to a nerve bundle. For each distance, the total amount of current entering the nerve bundle was kept constant. The corresponding current sourced from the electrode was scaled so as to maintain the total current entering the nerve bundle. The simulation geometry for source electrode at 13.3 mm from nerve bundle is shown in FIG. 11O.

Figure 11P:
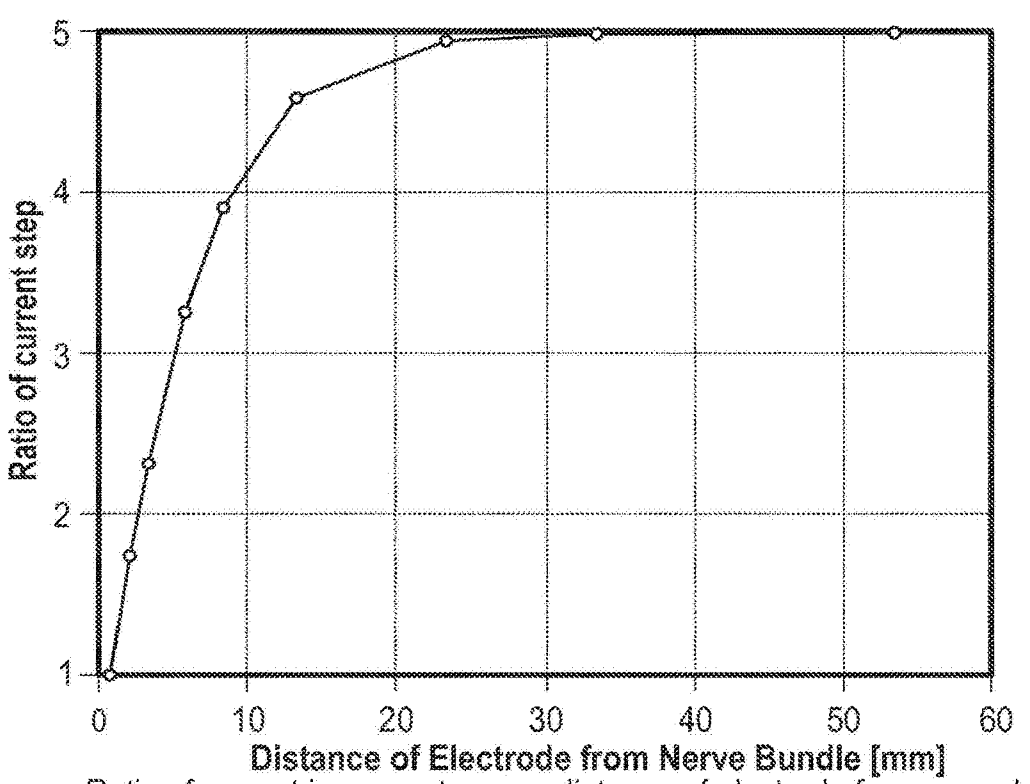

As stimulation elements 260 (e.g. electrodes) are positioned farther away from the nerve bundle, only a part of the sourced current enters the nerve bundle and the remaining current flows outside the nerve bundle. FIG. 11P shows the ratio by which the source current magnitude needs to be increased for the same amount of total current to pass through the nerve bundle. For example, for an electrode at 1 mm distance, if current is increased by 100 μA then at 10 mm distance, the current has to be increased by 410 μA (4.1*100 μA). It is also observed that the ratio tapers off after 30 mm distance of source electrode from nerve bundle. The ratio values and the distance at which it tapers depends on the volume surrounding the target nerve bundle and on the relative conductivity values of the nerve bundle and the surrounding tissue.

Based on these observations of FIG. 11P, it is clear that as the stimulation element 260 (e.g. electrode) is at distances further away from the nerve bundle, a higher amount of current needs to be sourced to make the same change in total current passing through nerve bundle. Thus as the distance between nerve and electrode increases, a larger amount of current is required to generate action potentials in nerve fibers. The remaining current that does not pass through the target nerve bundle is wasted in passing through other tissue. Furthermore, as the fraction of current that passes through the nerve bundle depends on the surrounding volume and its conductivity, the current requirement may vary considerably based on patient anatomy.

Figure 11Q:
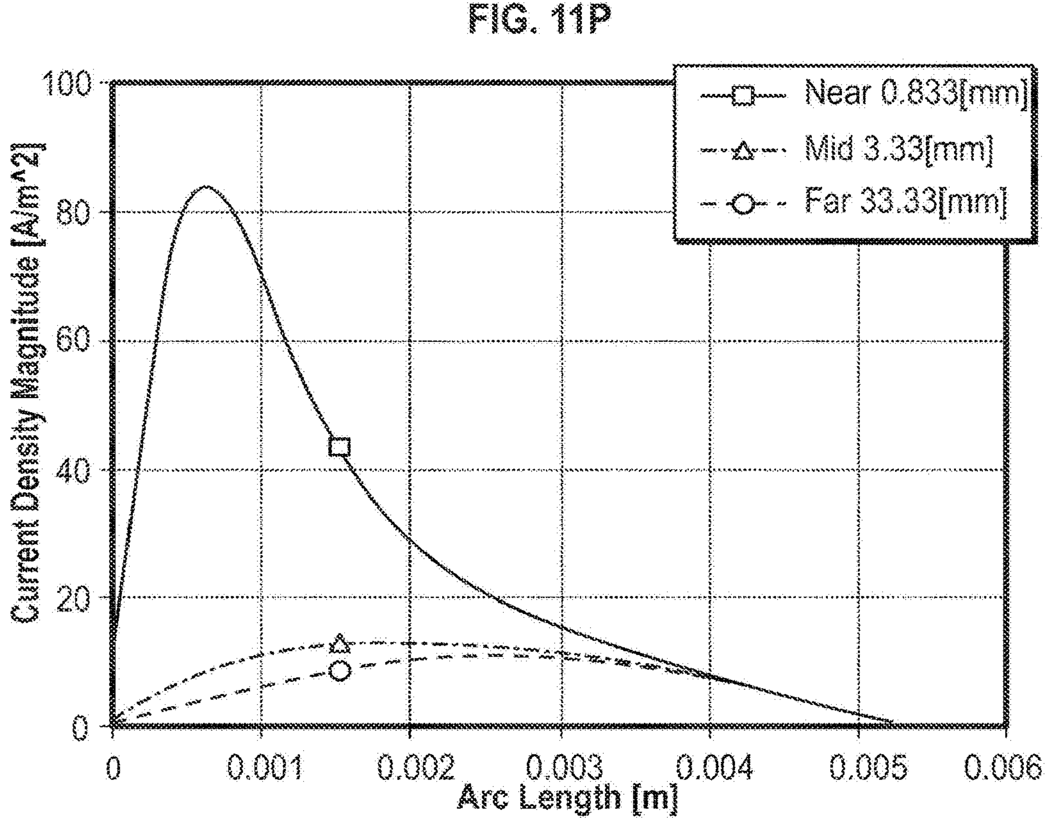

The spatial variation in the current density along the circumference of the nerve bundle has also been studied by applicant. FIG. 11Q illustrates a comparison of the current density along the circumference of the nerve bundle for various distances between a source electrode and the nerve bundle. As the source electrode is at locations farther away from the nerve bundle, the potential gradient near the nerve bundle decreases. Current density is dependent on the potential gradient. Hence it can be observed in FIG. 11Q that the current density profile is skewed when a source electrode is positioned closer to the nerve bundle and in comparison, as the electrode is positioned farther away, the current density profile evens out.

Based on the skewed current density profile, it can be determined that more current is sourced in a local region of the nerve bundle. In presence of multiple such stimulation elements 260 (e.g. multiple electrodes) positioned close to the nerve bundle, steering of the current in desired parts of the nerve bundle is enabled. On the other hand as the current density profile evens out, it will be difficult to have a local control of stimulation in the nerve bundle. Since fascicle distribution within a nerve bundle is not uniform, it is beneficial for apparatus 10 to be configured to steer current in specific regions of the nerve bundle (e.g. steering current to specific fibers of the nerve bundle while avoiding delivery of current to other fibers of the nerve bundle). In some embodiments, apparatus 10 is configured to steer current as described in applicant's co-pending U.S. patent application Ser. No. 17/383,985, titled "Stimulation Energy Systems with Current Steering", filed Jul. 23, 2021.

These observations presented in FIGS. 11P and 11Q indicate that the ability to steer stimulation current in the tissue regions of interest can enable local control over current flowing through the target nerve bundle and reduction of the wastage current. Together these experiments suggest that an implanted device 100 should be placed close to the target nerve to maximize efficiency (and correspondingly decrease the implanted battery and/or other energy storage element size), and to increase selectivity of the target fascicle.

Section 6—Conclusion

Simulation results conducted by applicant as described above indicate that a single stimulation element 260 (e.g. a single electrode) cannot selectively stimulate all non-nociceptive fibers while avoiding stimulation of other neural targets. Apparatus 10 comprising multiple stimulation elements 260 (e.g. multiple electrodes) that are placed close to the target nerve will have better spatial control to selectively depolarize the non-nociceptive fibers while consuming less power. Apparatus 10 can be configured to perform field focusing by current steering with multiple stimulation elements 260 to further optimize the stimulation efficacy (e.g. pain relief).

Figures 12A, 12B:
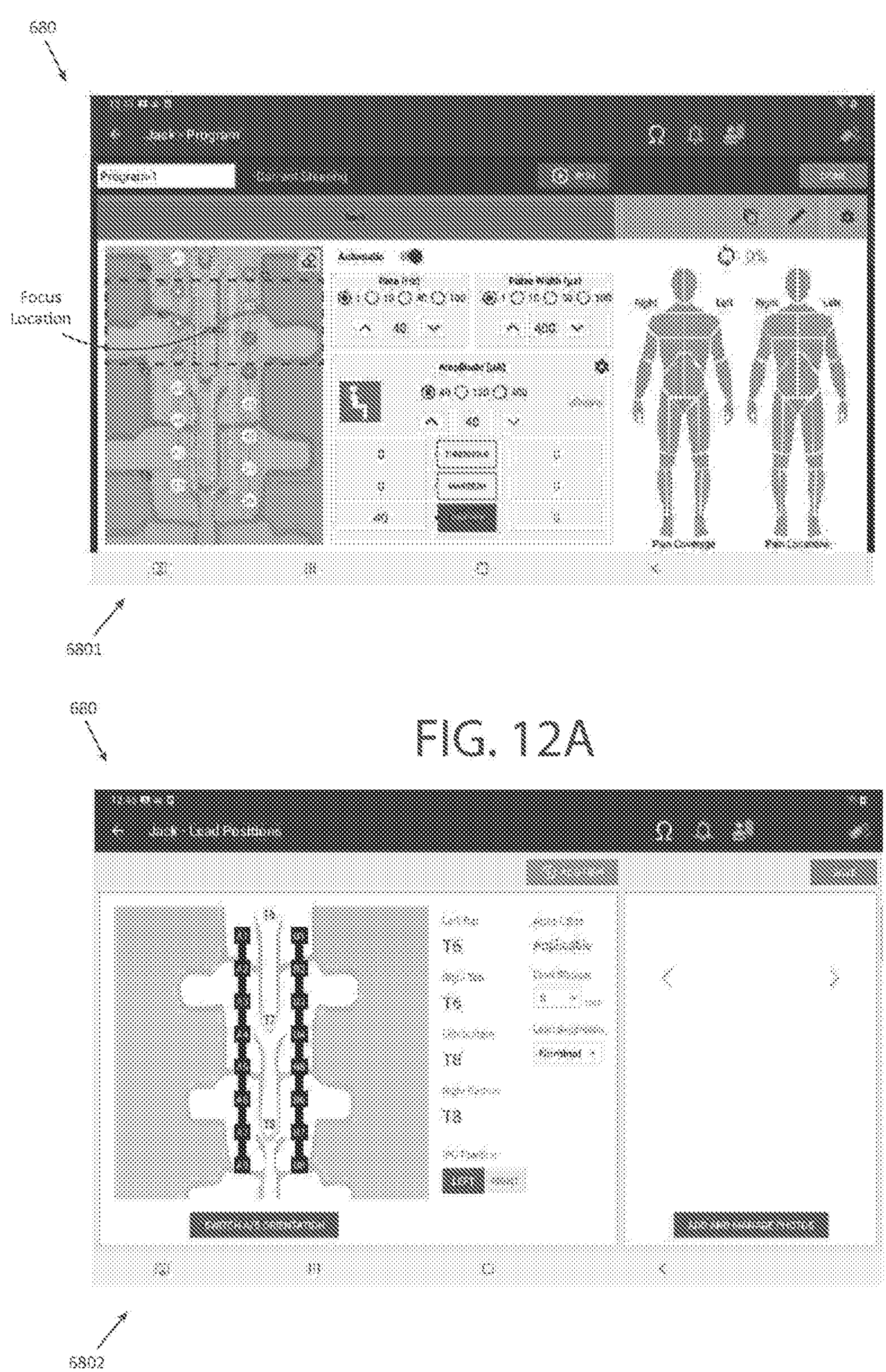
FIGS. 12A and 12B illustrate various user's views of a user interface, consistent with the present inventive concepts.

Referring now to FIGS. 12A and 12B, a user's view of various screens of a user interface of a stimulation apparatus is illustrated, consistent with the present inventive concepts. User interface 680 of FIG. 12 includes a "stimulation area screen", screen 6801, shown in FIG. 12A, and a "lead configuration screen", screen 6802, shown in FIG. 12B. Screen 6801 can be configured to provide a graphical representation of the patient's anatomy (e.g. a representation of the patient's spine as shown on the left side of FIG. 12A). Using screen 6801 of user interface 680, the user can select one or more "focus locations" within the provided anatomical representation, for example a focus location (e.g. a target stimulation location into which current is steered) indicated by the solid-line box shown in FIG. 12A. Based on the user selected focus location, apparatus 10 select stimulation anodes, cathodes, and the percentage of current allocation for each selected anode to steer the stimulation to the user selected focus location. In some embodiments, apparatus 10 steers the stimulation as described immediately herebelow. FIG. 12A shows three columns of potential focus locations available between the lead representations shown (e.g. representation of leads 265, described herein).

Apparatus 10 can operate in a current steering mode, "CS Mode", based on a finite element analysis (FEA) model, such as is described hereabove in reference to FIGS. 11A-Q In some embodiments, apparatus 10 operates in an "Automatic CS Mode" in which the current is steered automatically. In some embodiments, the CS Mode operates similar to current steering techniques described in applicant's co-pending U.S. patent application Ser. No. 17/383,985, titled "Stimulation Energy Systems with Current Steering", filed Jul. 23, 2021.

When operating in the Automatic CS Mode, as determined by a user of apparatus 10, via user interface 680 the user can specify the dual lead 265 stagger and dual lead 265 separation, and then select a focus point (e.g. on stimulation area screen 6801). Apparatus 10 then configures the stimulation element 260 polarities and anode percentage values to achieve the selected current steering focus point.

In some embodiments, if a dual lead 265 configuration is specified, and a stagger distance specified by the user is within a predetermined range (e.g. no more than 49 mm), a button to activate Automatic CS Mode is enabled (e.g. provided by user interface 680 to the user for selection).

In some embodiments, if a dual lead 265 configuration is specified, and a stagger distance specified by the user is within a predetermined range (e.g. no more than 49 mm), apparatus 10 can automatically enter Automatic CS Mode.

In some embodiments, apparatus 10 is configured to provide a "Manual CS Mode" to the user. In Manual CS Mode, the user of apparatus 10 can select the anodes, cathodes, and percentage of stimulation current allocation for each selected anode and/or cathode. User interface 680 can enable the user to "draw" a geometric shape between graphical representations of stimulation elements 260 (e.g. graphical representations of electrodes) to select active anodes (e.g. a line to select two anodes, triangle to select three, or a square to select four, as shown). A point can be indicated by the user within the geometric shape to adjust the proportion of current assigned to each stimulation element 260 (e.g. the proportion of current assigned to each anode and/or cathode based on the distance between the selected point and each anode and/or cathode).

In some embodiments, when apparatus 10 switches from Manual CS Mode to Automatic CS Mode, apparatus 10 uses the most recent focus location. Alternatively, apparatus 10 can use the top left/top most focus point in the first column of available focus locations (e.g. if a focus location has not been selected).

In some embodiments, upon switching from Manual CS Mode to Automatic CS Mode, apparatus 10 sets a stimulation amplitude for the Automatic CS Mode based on: the stimulation amplitude, rate, and/or pulse width that was used in the previous Manual CS Mode; and the current focus location, such that:

$$\text{Amplitudecurrent} = \text{Amplitudeprevious} * (\text{Rate previous} * \text{PulseWidthprevious}) / (\text{Ratecurrent} * \text{PulseWidthcurrent})$$

In some embodiments, upon switching from Automatic CS Mode to Manual CS Mode, apparatus 10 sets the stimulation parameter settings (e.g. amplitude, rate, pulse width, stimulation element 260 assignments, and anode percentage values) for the Manual CS Mode to the sample levels used in the previous Automatic CS Mode.

Apparatus 10 can be configured such that if apparatus 10 is being used for spinal cord stimulation, Automatic CS Mode is selected, and the lead 265 stagger and horizontal spacing are specified, one or more of the following functions can be performed and/or otherwise enabled ("performed" herein): apparatus 10 displays focus points between the leads 265 as a "N by 3" matrix representing 1 mm vertical spacing, excluding focus points specified by an FEA model of apparatus 10; apparatus 10 enters a mode in which the user can select a focus point as a target location (reference the rectangle selected focus point of FIG. 12A); apparatus 10 stores all stimulation target locations with the most recent stimulation parameters (e.g. amplitude, pulse width, rate) for each target location, including associated patient posture per therapy program per therapy session; apparatus 10 displays (e.g. via user interface 680) the current target location (e.g. as a highlighted focus point) regardless of whether that location has received stimulation energy from apparatus 10; apparatus 10 displays previous target locations that were stimulated with a graphical highlight that differentiates the stimulation locations from non-stimulated locations (e.g. a particular color, font, hue, or other graphical differentiation); and/or apparatus 10 displays previously stored stimulation parameters associated with a prior stimulation target location.

In some embodiments, apparatus 10 can be configured such that if apparatus 10 is being used for spinal cord stimulation, Automatic CS Mode is selected, and the lead 265 stagger and horizontal spacing are specified, apparatus 10 is configured to modify an amplitude of stimulation energy delivery delivered to a current target location if pulse width and/or rate have changed for energy delivery to that current target location, such as to maintain the charge based on the closest target location or the most recent of the closest equidistant "neighboring target locations" such that:

$$\text{Amplitudetarget} = \text{Amplitudeneighbor} * (\text{Rate neighbor} * \text{PulseWidthneighbor}) / (\text{Ratetarget} * \text{PulseWidthtarget})$$

where neighboring target locations are those within a rectangular boundary which is defined considering 'furthest' edge of the closest top and bottom stimulation elements 260 electrodes starting from the left element 260 assignment. For example, horizontal spacing and vertical stagger resolution can be used in determining distance to the neighboring target locations. See FIG. 12A for an example for the boundary of neighboring target locations, as indicated by the dashed-line box shown. In some embodiments, apparatus 10 is configured to allow the user to set an amplitude upon user selection of a new target location, if that location has not been stimulated during the current therapy session, with a suggested value equal to either (a) "threshold amplitude" that was recorded for the closest neighbor or the most recent of the closest equidistant target locations, or (b) half of the most recent "working amplitude". A threshold amplitude can comprise a threshold at which the patient can feel the stimulation being delivered. In some embodiments a threshold amplitude comprises a maximum threshold above which the patient does not want the amplitude to increase. A working amplitude can comprise an amplitude at which apparatus 10 is currently and/or was most recently delivering stimulation energy. User interface 680 can provide one or more controls for the user to increase and/or decrease the working amplitude, as well as store one or more threshold and/or maximum threshold amplitude values.

Apparatus 10 can be configured to determine the current stimulation element positions (e.g. positions of elements 260 used for current steering), element 260 polarities, and/or anode percentages per the FEA model, such as using the current target stimulation location, lead 265 stagger, and lead 265 spacing as inputs. Manual stimulation element 260 selection and configuration can be disabled in Auto CS Mode.

In some embodiments, during stimulation apparatus 10 can be configured to perform one or more of the following functions: apparatus 10 dynamically updates the current target location (e.g. continuously or intermittently); and/or apparatus 10 dynamically updates stored working amplitude and stimulation element 260 configuration upon user selection of a previously stimulated target location where the pulse width and/or rate match the most recently stimulated target location. In some embodiments, during stimulation apparatus 10 dynamically updates the stored working amplitude, rate, pulse width, and/or stimulation element 260 configuration upon user selection of a previously stimulated target location where the pulse width and/or rate do not match the most recently stimulated target location, after first requiring the user to set an amplitude with a suggested value based on the previous and current target locations such that:

$$\text{Amplitudecurrent} = \text{Amplitudeprevious} * (\text{Rate previous} * \text{PulseWidthprevious})/(\text{Ratecurrent} * \text{PulseWidthcurrent})$$

In some embodiments, if the lead 265 configuration stagger or horizontal spacing is modified for the future stimulation therapy session after copy, pasting, and/or duplicating a therapy session in which current steering is performed (a "CS session" herein), or the lead 265 configuration stagger or horizontal spacing is modified for an editable CS session, apparatus 10 shall clear the stored target locations and reset the amplitude for stimulation therapy, and, upon displaying or downloading an affected CS program, notify the user that the stored target locations and amplitudes for stimulation therapy were reset.

Referring now to FIG. 13, a schematic view of a charger 61 for an external device 500 is shown, consistent with the present inventive concepts. In FIG. 13, a schematic view of a charger 61 is illustrated. Charger 61 can comprise various components, such as: coil 6101; transmit module 6102; switch 6103 (e.g. a load switch); converter 6104 (e.g. a DC to DC converter); Wi-Fi module 6105; memory module 6106 (e.g. a flash memory module, such as at least a 2 megabit module); BLE module 6107; memory module 6108 (e.g. a flash memory module for storing downloaded data, such as at least a 2 gigabit module); drive circuitry 6109; and/or user interface 6110 (e.g. a user interface comprising various user input and/or user output components), which can be connected as shown in FIG. 13. User interface 6110 can comprise one or more indicator lights 6111 (e.g. light emitting diodes, six shown). Indicator lights 6111 can comprise components configured to produce light of variable color and/or variable intensity (e.g. to differentiate provided information). Charger 61 can be configured such that coil 6101 can transmit power and/or data to one or more external devices 500 and/or other component of apparatus 10 (e.g. an implantable device 100). Alternatively or additionally, charger 61 can be configured such that coil 6101 can receive data from one or more external devices 500 and/or other components of apparatus 10 (e.g. an implantable device 100).

In FIG. 13A, a schematic view of a particular connection and communication arrangement for apparatus 10 is illustrated. Charger 61 is in communication (e.g. wireless communication) with an external device 500. Charger 61 can be connected (as shown, such as via a wired or wireless connection) to the Internet and/or any network (e.g. a wired or wireless network), network 910 shown. Network 910 can comprise a Wi-Fi based and/or cellular based wireless network. Charger 61 can comprise a Wi-Fi module, module 6105, which can include device firmware update (DFU) and analytic capability. Charger 61, via network 910, can be in communication with one or more servers or other computer devices, server 920 shown. A programmer 600 (e.g. a patient programmer 600' as described herein) can be in communication with charger 61. Each programmer 600 can comprise a set of user input and/or user output components, user interface 680 shown and as described in reference to FIG. 1 and otherwise herein.

In FIG. 13B, a schematic view of another connection and communication arrangement for apparatus 10 is illustrated. Charger 61 is in communication (e.g. wireless communication) with an external device 500. Charger 61 can be connected (as shown, such as via a wired or wireless connection) to the Internet and/or any network (e.g. a computer network), network 910 shown. Charger 61, via network 910, can be in communication with programmer 600, such as a clinician programmer 600" as described herein, such that a clinician can access and/or adjust one or more stimulation parameters and/or other apparatus 10 parameters using the programmer 600.

Network 910 and server 920 can be configured as "the cloud", such as to collect, process, and/or transmit data to and/or between one or more apparatus 10 components (e.g. a programmer 600, charger 61, and/or external device 500). In some embodiments, charger 61 is configured as a "gateway" device such that data received by charger 61 from network 910 and/or directly from another apparatus 10 component (e.g. programmer 600) can be uploaded into one or more external devices 500, as described herein. In some embodiments, charger 61 (e.g. via user interface 6110) is configured to modify the network settings of network 910. Alternatively or additionally, a programmer 600 (e.g. via user interface 680) is configured to modify the network settings of network 910. In some embodiments, one or more programmers 600 (e.g. a clinician programmer 600" as described herein) can be configured to monitor (and allow a user to view) the status of a charger 61 and/or an external device 500 operably attached to charger 61, such as monitoring that is performed via data transfer over network 910 (e.g. to allow monitoring by a clinician that is remote from the patient).

Charger 61 can be configured to charge one, two, or more external devices 500 (e.g. charge power supply 570 of the associated external device 500), as described herein. Charger 61 can be configured to perform Qi and/or WPC wireless charging of each external device 500.

In addition or as an alternative to charging, charger 61 can be configured to upload data (e.g. stimulation parameter data and/or other apparatus 10 data) from one, two or more external devices 500), and/or transmit data (e.g. commands representing changes to stimulation parameter settings and/or other apparatus/10 settings), also as described herein. Charger 61, external device 500, and/or another apparatus 10 component can be configured to transmit data wirelessly using one or more wireless communication protocols (e.g. Bluetooth communication). Downloaded data can represent data of one or more external devices 500, and/or one or more implantable devices 100 (e.g. device 100 data that has been uploaded into an external device 500), such as usage data, error data, and/or other logged data. Data transfer between charger 61 and an external device 500 can occur (e.g. simultaneously occur) while charger 61 is charging external device 500. Charger 61 can transmit the data uploaded from an external device 500 to a separate device (e.g. a programmer 600) directly, and/or via network 910, such as via a wired and/or wireless connection. In some embodiments, the data uploaded is transmitted to a secure cloud location (e.g. network 910). In some embodiments, data is downloaded and stored on charger 61 (e.g. in memory module 6108, such as storage performed if no network connection is currently available), and this data transmitted to a separate device at a later time.

In some embodiments, the programmer 600 of FIG. 13A or 13B comprises a cell phone or other consumer electronic device including a software application facilitating access and/or adjustment of one or more stimulation parameters and/or other apparatus 10 parameters using the programmer 600.

In some embodiments, user interface 6110 of charger 61 is configured to display the status of an external device 500 charging and/or status of a network connection to a user (e.g. via indicators 6111 and/or other output component of user interface 6110)

In some embodiments, configuration of charger 61 and/or an external device 500 can be modified via network 910, such as when commands entered into a programmer 600 are transferred via network 910 to a charger 61 and/or external device 500 and device parameters are changed and/or firmware of the associated device is changed (e.g. a firmware upgrade is performed via a remote device). In some embodiments, charger 61 is configured to download firmware upgrade data, via network 910, from server 920, and to store the firmware upgrade data (e.g. in memory module 6106 or 6108). When an external device 500 is operably connected to charger 61 (e.g. the device 500 is positioned on and/or otherwise proximate charger 61 such that wired or wireless transmissions can be performed), a check for a firmware upgrade can be performed (e.g. a check to determine if the device 500 is configured in the latest available firmware configuration). If not current, the firmware upgrade data can be transferred from charger 61 to the external device 500 and the associated firmware upgraded. In some embodiments, configuration (e.g. firmware configuration) of Wi-Fi module 6105 can be upgraded in this arrangement. In some embodiments, configuration (e.g. firmware configuration) of BLE module 6107 can be upgraded in this arrangement, such as via upgrade data sent using a universal asynchronous receiver-transmitter (UART) of charger 61.

In some embodiments, an external device 500 that has not been used in a patient treatment (a "new device") is configured via this remote access configuration, avoiding a nurse, clinician, and/or other healthcare worker needing to be present at the patient site to set up a new device 500 for use in treating the patient. In some embodiments, a clinician or other user remote from the patient can interact with the patient, and/or one or more components of apparatus 10 at the patient location, via network 910, such as to provide technical support, facilitate the procurement (e.g. reorder) of additional apparatus 10 components (e.g. external devices 500, patient attachment device 70, and/or other apparatus 10 component). In some embodiments, charger 61 is configured to allow transfer of data (e.g. stimulation parameter settings or other configuration data) between multiple external devices 500 (e.g. multiple external device 500 that are operably connected to charger 61 in a simultaneous and/or sequential attachment). In some embodiments, upgrading of a first external device 500 via information uploaded from a second external device 500 is only performed after a confirmation routine is successfully completed, such as a confirmation routine in which a clinician, via a programmer 600, "approves" the particular upgrade being performed. In some embodiments, data related to a particular upgrade of an external device 500 and/or charger 61 is received (e.g. via network 910 or otherwise) from a programmer 600 (e.g. a clinician programmer 600").

In some embodiments, data is transmitted between server 920 (e.g. via network 910) and multiple external devices 500 of a single apparatus 10, or between server 920 and one or more components of each of multiple systems 10 (e.g. multiple systems 10 treating multiple corresponding patients). In these embodiments, data can be uploaded to server 920 for analysis (e.g. via an algorithm 15). In this arrangement, status checks can be performed, such as to determine adequate revision of component firmware, and/or other adequacy of various apparatus 10 components. In some embodiments, adequacy of a power supply (e.g. a battery of external device 500 or other apparatus 10 component) can be confirmed, and instructions sent if a new power supply should be used (e.g. due to a revision check and/or an analysis of battery level or other usage information). In some embodiments, data uploaded by apparatus 10 can be analyzed to assess the patient use of apparatus 10, such as to potentially identify undesired use (e.g. non-use and/or declining use). In these embodiments, the patient use information can be transmitted to the patient's clinician, the patient, or both.

Figure 14A:
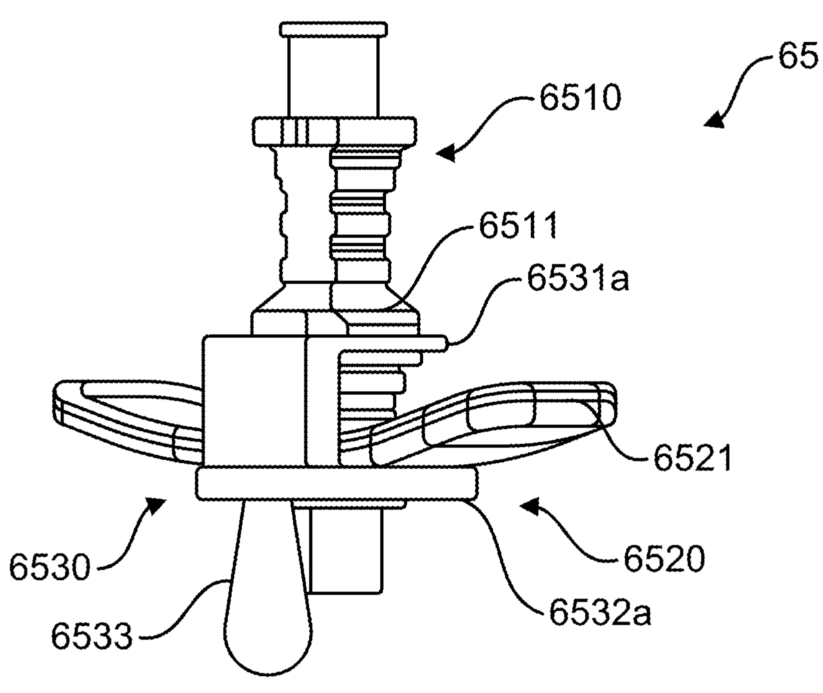
FIGS. 14A-14D illustrate various views of an implantation tool, consistent with the present inventive concepts.
Figure 14B:
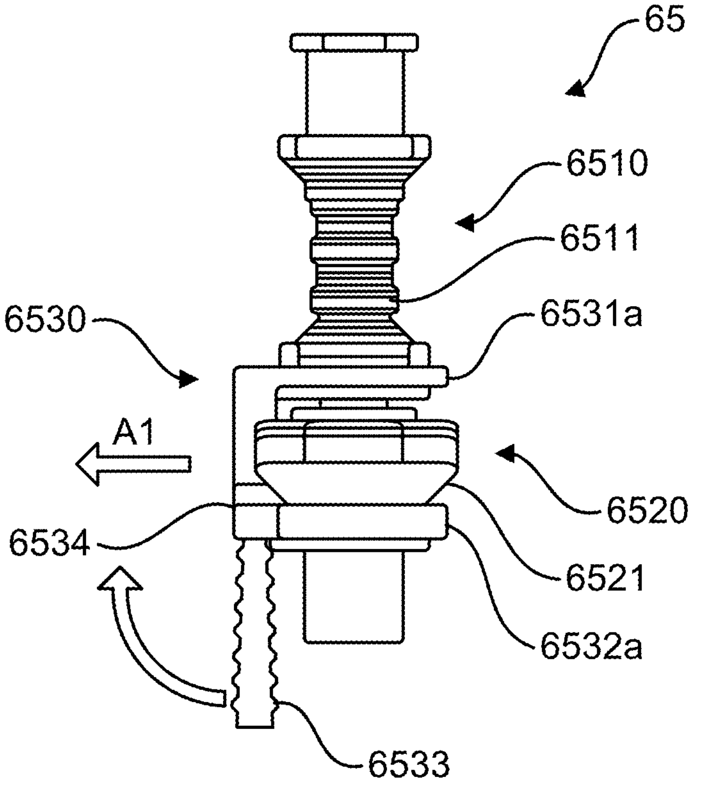
Figure 14C:
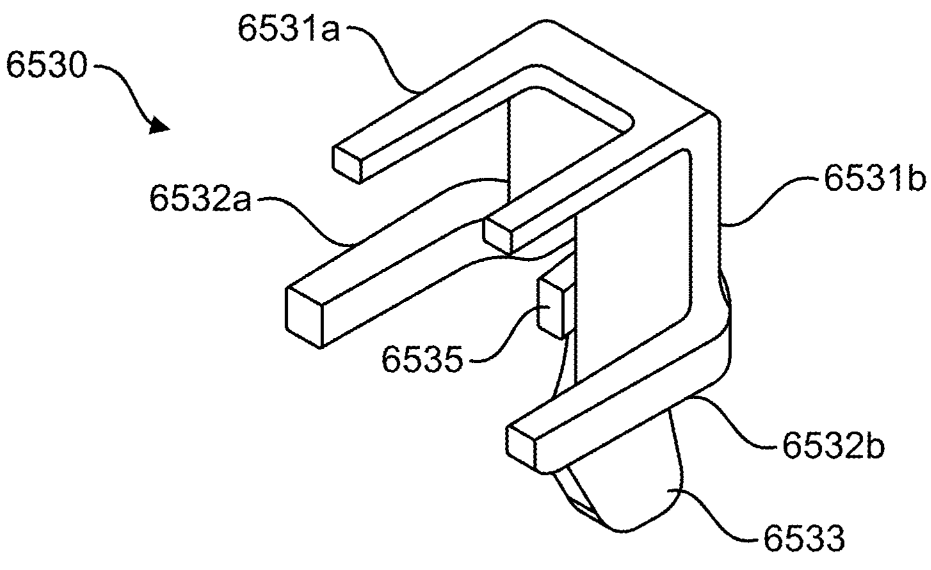
Figure 14D:
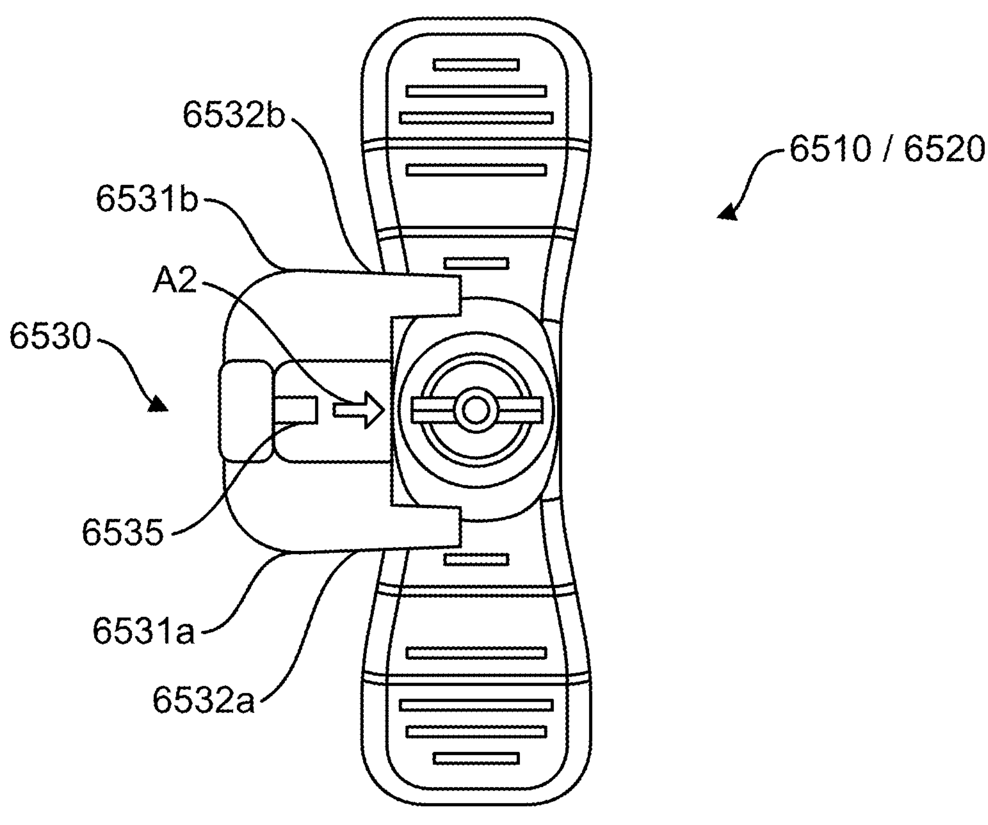

Referring now to FIGS. 14A-14C, a perspective view, a side view, and a top view, respectively, of a proximal portion of an implantation tool including a needle, a sheath, and a connecting component are illustrated, consistent with the present inventive concepts. In FIG. 14D, a perspective view of the connecting component of the tool of FIGS. 14A-14C is illustrated. Tool 65 of FIGS. 14A-14C can be of similar construction and arrangement as a tool 65 described herein in reference to FIG. 1. Tool 65 of FIGS. 14A-14C comprises a needle 6510 including a proximal portion, needle hub 6511, and a sheath 6520 including a proximal portion, sheath hub 6521. Needle 6510 is shown inserted into sheath 6520 in each of FIGS. 14A-14C. Tool 65 further comprises connector 6530, which includes a first pair of legs 6531*a* and 6531*b*, and a second pair of legs 6532*a* and 6532*b*. In FIGS. 14A-14B, connector 6530 is shown attached to needle 6510 and sheath 6520. In FIG. 14C, connector 6530 is positioned to be attached to needle 6510 and sheath 6520.

In the attached configuration shown in FIGS. 14A-14B, legs 6531*a-b* frictionally engage needle hub 6511, and legs 6532*a-b* frictionally engage sheath hub 6521. While attached, connector 6530 prevents undesired translation of needle 6510 relative to sheath 6520. In some embodiments, connector 6530 comprises projection 6535 which is configured to frictionally engage needle hub 6511 when connector 6530 is attached as shown in FIGS. 14A-14B. When connector 6530 is in this attached configuration, projection 6535 applies a force to needle hub 6511 that prevents undesired rotation of needle 6510 relative to sheath 6520.

Connector 6530 can include a user-graspable portion, tab 6533 shown, which can be gripped by an operator (e.g. an implanting clinician), such as to apply a force (e.g. a torsional force as shown in FIG. 14B) to cause connector 6530 to detach (e.g. travel in the direction of the arrow A1 shown) from needle 6510 and sheath 6520. Connector 6530 can comprise a living hinge, hinge 6534, which can accommodate rotation of tab 6533 when the force is applied. Connector 6530 can be attached (e.g. reattached) to needle 6510 and sheath 6520 by positioning connector 6530 as shown in FIG. 14D. Once positioned, connector 6530 can be advanced (e.g. advancing in the direction of arrow A2 shown) toward the assembly including needle 6510 inserted into sheath 6520, causing legs 6531*a, b* to frictionally engage needle hub 6511 and legs 6532*a, b* to frictionally engage sheath hub 6521 (e.g. into the configuration shown in FIGS. 14A-14B).

While the preferred embodiments of the devices and methods have been described in reference to the environment in which they were developed, they are merely illustrative of the principles of the present inventive concepts.

Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method for treating pain of a patient using a stimulation system, comprising:

receiving, via a user interface of the stimulation system, a target stimulation location for the patient, wherein the target stimulation location comprises a nerve bundle within a peripheral nervous system (PNS) of the patient;

configuring, via a microprocessor of the stimulation system and based on the received target stimulation location, each of a first electrode and a third electrode of a first plurality of electrodes as an anode, and a second electrode of a second plurality of electrodes as a cathode, wherein the first plurality of electrodes is on a first lead of the stimulation system and the second plurality of electrodes is on a second lead of the stimulation system;

adjusting, via the microprocessor, a proportion of stimulation current assigned to the first electrode to direct current through the nerve bundle in the target stimulation location; and delivering the stimulation current to the target stimulation location using a first current source coupled to the first electrode and a second current source coupled to the third electrode.

2. The method of claim 1, wherein each of the first and second leads is positioned adjacent to the nerve bundle.

3. The method of claim 2, wherein each of the first and second leads is positioned such that a current density along a circumference of the nerve bundle is skewed to steer the stimulation current to specific regions of the nerve bundle.

4. The method of claim 1, wherein configuring the first and second electrodes comprises receiving, via the user interface, a vertical separation and a horizontal separation between the first and second leads.

5. The method of claim 4 further comprising configuring, using the vertical and horizontal separations, a polarity and an anode percentage value for each of the first and third electrodes.

6. The method of claim 4, wherein the vertical separation received is a distance within a defined range and the method further comprises, after receiving the vertical separation, initiating an automatic current steering mode for the stimulation system.

7. The method of claim 6, wherein the defined range is 0 mm to 49 mm.

8. The method of claim 1, wherein configuring the first and third electrodes comprises receiving a configuration of the first and third electrodes via a graphical representation provided by the user interface, wherein the graphical representation comprises each electrode of the first plurality of electrodes and the second plurality of electrodes.

9. The method of claim 8, wherein the configuration comprises a geometric shape comprising the first electrode.

10. The method of claim 9, wherein the geometric shape comprises a line, a triangle, or a square.

11. The method of claim 9, wherein adjusting the proportion of stimulation current comprises:

receiving, via the user interface, a point within the geometric shape; and determining the proportion of stimulation current based on a distance between the point and the first and third electrodes.

12. The method of claim 8, wherein the graphical representation further comprises the anatomy of the patient at the target stimulation location.

13. A system for treating pain, comprising:

an implantable device configured to deliver stimulation to a patient via a first plurality of electrodes of a first lead and a second plurality of electrodes of a second lead, wherein the first and second leads are positioned adjacent to a nerve bundle; and a user interface configured to provide a graphical representation of the first and second plurality of electrodes, and to receive a target stimulation location including the nerve bundle, wherein the user interface is configured to receive a geometric shape comprising a first electrode of the first plurality of electrodes, wherein the system is configured to:

configure, via a microprocessor of the system and based on the received target stimulation location, the first electrode as an anode, and a second electrode of the second plurality of electrodes as a cathode;

adjust, via the microprocessor, a proportion of stimulation current assigned to the first electrode to direct current through the nerve bundle in the target stimulation location, wherein, to adjust the proportion of stimulation current assigned to the first electrode, the system is configured to receive, via the user interface, a point within the geometric shape, and determine the proportion of stimulation current based on a distance between the point and the first electrode; and deliver the stimulation current to the target stimulation location.

14. The system of claim 13, wherein the nerve bundle is within a peripheral nervous system (PNS) of the patient.

15. The system of claim 13, wherein the geometric shape comprises a line, a triangle, or a square.

16. The method of claim 13, wherein the graphical representation further comprises the anatomy of the patient at the target stimulation location.

* * * * *